United States Patent
Maguire et al.

(10) Patent No.: US 6,599,288 B2
(45) Date of Patent: Jul. 29, 2003

(54) APPARATUS AND METHOD INCORPORATING AN ULTRASOUND TRANSDUCER ONTO A DELIVERY MEMBER

(75) Inventors: Mark A. Maguire, San Jose, CA (US); James C. Peacock, III, San Carlos, CA (US); Alan K. Schaer, San Jose, CA (US); Veijo Suorsa, Sunnyvale, CA (US)

(73) Assignee: Atrionix, Inc., Palo Alto, CA (US)

( * ) Notice: Subject to any disclaimer, the term of this patent is extended or adjusted under 35 U.S.C. 154(b) by 0 days.

(21) Appl. No.: 09/859,083

(22) Filed: May 16, 2001

(65) Prior Publication Data
US 2002/0022833 A1 Feb. 21, 2002

Related U.S. Application Data

(60) Provisional application No. 60/204,912, filed on May 16, 2000.

(51) Int. Cl.[7] ............................................. A61B 18/18
(52) U.S. Cl. ........................ 606/27; 600/459; 600/466; 601/2
(58) Field of Search ........................... 606/27, 28, 41; 607/96; 601/2, 3; 600/439, 459, 462, 466

(56) References Cited

U.S. PATENT DOCUMENTS

| | | |
|---|---|---|
| 3,781,781 A | 12/1973 | Groves, Jr. |
| 3,938,502 A | 2/1976 | Born |
| 4,117,836 A | 10/1978 | Erickson |
| 4,316,472 A | 2/1982 | Mirowski et al. |
| 4,441,266 A | 4/1984 | Cosman |
| 4,449,528 A | 5/1984 | Auth |
| 4,522,205 A | 6/1985 | Taylor |
| 4,569,801 A | 2/1986 | Molloy |

(List continued on next page.)

FOREIGN PATENT DOCUMENTS

| | | |
|---|---|---|
| EP | 0 623 360 B1 | 3/1999 |
| WO | WO 93/16632 A1 | 9/1993 |
| WO | WO 93/20767 | 10/1993 |
| WO | WO 93/20770 A2 | 10/1993 |
| WO | WO 93/20886 A1 | 10/1993 |
| WO | WO 94/00050 A1 | 1/1994 |

(List continued on next page.)

OTHER PUBLICATIONS

Avitall et al., "Physics and Engineering of Transcatheter Tissue Ablation," Journal of American College of Cardiology, 22(3):921–932 (1993).

Cox, JL et al., "The Surgical Treatment of Atrial Fibrillation. I. Summary," Thoracic and Cariovascular Surgery 101(3), pp. 402–405 (1991).

Cox, JL, "The Surgical Treatment of Atrial Fibrillation. IV. Surgical Technique, Thoracic and Cardiovascular Surgery," 101(4), pp. 584, 592 (1991).

Fram et al., "Feasibility of RF Powered Thermal Balloon Ablation of Atrioventricular Bypass Tracts via the Coronary Sinus: In vivo Canine Studies," PACE, 18:1518–1530 (1995).

Jais et al., "A Focal Source of Atrial Fibrillation Treated by Discrete Radiofrequency Ablation," Circulation, 95:572–576 (1997).

(List continued on next page.)

Primary Examiner—Michael Peffley

(57) ABSTRACT

A medical device assembly and method provides an ultrasound transducer mounted onto a catheter shaft. The ultrasound transducer is mounted such that there is a radial separation between the transducer and the underlying catheter shaft. The transducer is mounted on support structures which do not bridge the gap between the transducer and delivery member. The location of the support structures provides for an "airbacked" transducer that is very efficient and prevents heat build-up in the materials in contact therewith.

26 Claims, 56 Drawing Sheets

U.S. PATENT DOCUMENTS

| | | | |
|---|---|---|---|
| 4,641,649 | A | 2/1987 | Walinsky |
| 4,660,571 | A | 4/1987 | Hess et al. |
| 4,662,368 | A | 5/1987 | Hussein |
| 4,669,469 | A | 6/1987 | Gifford, II et al. |
| 4,672,962 | A | 6/1987 | Hershenson |
| 4,673,563 | A | 6/1987 | Berne |
| 4,676,258 | A | 6/1987 | Inokuchi |
| 4,699,147 | A | 10/1987 | Chilson et al. |
| 4,757,820 | A | 7/1988 | Itoh |
| 4,762,129 | A | 8/1988 | Bonzel |
| 4,790,311 | A | 12/1988 | Ruiz |
| 4,807,620 | A | 2/1989 | Strul |
| 4,841,979 | A | 6/1989 | Dow |
| 4,882,777 | A | 11/1989 | Narula |
| 4,898,591 | A | 2/1990 | Jang |
| 4,917,096 | A | 4/1990 | Englehart |
| 4,924,863 | A | 5/1990 | Sterzer |
| 4,936,281 | A | 6/1990 | Stasz |
| 4,940,064 | A | 7/1990 | Desai |
| 4,945,912 | A | 8/1990 | Langberg |
| 4,951,677 | A | 8/1990 | Crowley et al. |
| 4,976,711 | A | 12/1990 | Parins et al. |
| 4,998,933 | A | 3/1991 | Eggers |
| 5,000,185 | A | 3/1991 | Yock |
| 5,002,059 | A | 3/1991 | Crowley et al. |
| 5,035,694 | A | 7/1991 | Kasprzyk |
| 5,078,717 | A | 1/1992 | Parins et al. |
| 5,078,736 | A | 1/1992 | Behl |
| 5,087,249 | A | 2/1992 | Qin et al. |
| 5,090,958 | A | 2/1992 | Sahota |
| 5,104,393 | A | 4/1992 | Isner |
| 5,131,397 | A | 7/1992 | Crowley et al. |
| 5,147,355 | A | 9/1992 | Friedman et al. |
| 5,156,157 | A | 10/1992 | Valenta, Jr. et al. |
| 5,178,618 | A | 1/1993 | Kandarpa |
| 5,186,177 | A | 2/1993 | O'Donnell et al. |
| 5,190,540 | A | 3/1993 | Lee |
| 5,195,990 | A | 3/1993 | Weldon |
| 5,209,229 | A | 5/1993 | Gilli |
| 5,222,501 | A | 6/1993 | Ideker et al. |
| 5,226,430 | A | 7/1993 | Spears |
| 5,228,442 | A | 7/1993 | Imran |
| 5,231,995 | A | 8/1993 | Desai |
| 5,255,679 | A | 10/1993 | Imran |
| 5,263,493 | A | 11/1993 | Avitall |
| 5,281,215 | A | 1/1994 | Milder |
| 5,292,321 | A | 3/1994 | Lee |
| 5,293,868 | A | 3/1994 | Nardella |
| 5,293,869 | A | 3/1994 | Edwards |
| 5,295,484 | A | 3/1994 | Marcus |
| 5,300,085 | A | 4/1994 | Yock |
| 5,313,943 | A | 5/1994 | Houser et al. |
| 5,324,255 | A | 6/1994 | Passafaro et al. |
| 5,324,284 | A | 6/1994 | Imran |
| 5,325,860 | A | 7/1994 | Seward et al. |
| 5,331,966 | A | 7/1994 | Bennett et al. |
| 5,342,292 | A | 8/1994 | Nita et al. |
| 5,344,435 | A | 9/1994 | Turner et al. |
| 5,345,936 | A | 9/1994 | Pomeranz et al. |
| 5,345,940 | A | 9/1994 | Seward et al. |
| 5,348,554 | A | 9/1994 | Imran |
| 5,368,035 | A | 11/1994 | Hamm et al. |
| 5,368,557 | A | 11/1994 | Nita et al. |
| 5,368,558 | A | 11/1994 | Nita |
| 5,370,678 | A | 12/1994 | Edwards et al. |
| 5,372,138 | A | 12/1994 | Crowley et al. |
| 5,385,148 | A | 1/1995 | Lesh et al. |
| 5,385,544 | A | 1/1995 | Edwards et al. |
| 5,391,197 | A | 2/1995 | Burdette et al. |
| 5,409,000 | A | 4/1995 | Imran |
| 5,411,524 | A | | 5/1995 | Rahul |
| 5,421,338 | A | | 6/1995 | Crowley et al. |
| 5,423,808 | A | | 6/1995 | Edwards et al. |
| 5,423,811 | A | | 6/1995 | Imran |
| 5,427,119 | A | | 6/1995 | Swartz |
| 5,433,708 | A | | 7/1995 | Nichols et al. |
| 5,437,664 | A | | 8/1995 | Cohen et al. |
| 5,447,509 | A | | 9/1995 | Mills et al. |
| 5,449,380 | A | | 9/1995 | Chin |
| 5,454,373 | A | | 10/1995 | Koger et al. |
| 5,456,682 | A | | 10/1995 | Edwards et al. |
| 5,465,716 | A | | 11/1995 | Avitall |
| 5,474,530 | A | | 12/1995 | Passafaro et al. |
| 5,484,400 | A | | 1/1996 | Edwards et al. |
| 5,487,385 | A | | 1/1996 | Avitall |
| 5,496,312 | A | | 3/1996 | Klicek |
| 5,496,346 | A | | 3/1996 | Horzewski et al. |
| 5,497,119 | A | | 3/1996 | Tedrow et al. |
| 5,497,774 | A | | 3/1996 | Swartz et al. |
| 5,501,227 | A | | 3/1996 | Yock |
| 5,505,702 | A | | 4/1996 | Arney |
| 5,505,730 | A | | 4/1996 | Edwards |
| 5,509,900 | A | | 4/1996 | Kirkman |
| 5,522,873 | A | | 6/1996 | Jackman et al. |
| 5,545,161 | A | | 8/1996 | Imran |
| 5,545,193 | A | | 8/1996 | Fleischman |
| 5,549,661 | A | | 8/1996 | Kordis |
| 5,558,672 | A | | 9/1996 | Edwards |
| 5,562,720 | A | | 10/1996 | Stern |
| 5,564,440 | A | | 10/1996 | Swartz |
| 5,569,241 | A | | 10/1996 | Edwards |
| 5,571,088 | A | | 11/1996 | Lennox et al. |
| 5,571,159 | A | | 11/1996 | Alt |
| 5,575,766 | A | | 11/1996 | Swartz |
| 5,575,772 | A | | 11/1996 | Lennox |
| 5,575,788 | A | | 11/1996 | Baker |
| 5,575,810 | A | | 11/1996 | Swanson |
| 5,582,609 | A | | 12/1996 | Swanson |
| 5,588,432 | A | | 12/1996 | Crowley |
| 5,606,974 | A | * | 3/1997 | Castellano et al. .... 128/662.06 |
| 5,607,422 | A | | 3/1997 | Smeets et al. |
| 5,617,854 | A | | 4/1997 | Munsif |
| 5,620,479 | A | * | 4/1997 | Diederich ................... 607/97 |
| 5,630,837 | A | | 5/1997 | Crowley |
| 5,642,736 | A | | 7/1997 | Avitall |
| 5,645,082 | A | | 7/1997 | Sung et al. |
| 5,658,278 | A | | 8/1997 | Imran |
| 5,673,695 | A | | 10/1997 | McGee et al. |
| 5,676,662 | A | | 10/1997 | Feischhacker et al. |
| 5,683,445 | A | | 11/1997 | Swoyer |
| 5,685,322 | A | | 11/1997 | Sung et al. |
| 5,685,839 | A | | 11/1997 | Edwards et al. |
| 5,687,723 | A | | 11/1997 | Avitall |
| 5,687,729 | A | | 11/1997 | Schaetzle |
| 5,688,267 | A | | 11/1997 | Panescu |
| 5,690,611 | A | | 11/1997 | Swartz et al. |
| 5,693,078 | A | | 12/1997 | Desai et al. |
| 5,697,925 | A | | 12/1997 | Taylor |
| 5,697,927 | A | | 12/1997 | Imran |
| 5,702,438 | A | | 12/1997 | Avitall |
| 5,715,818 | A | | 2/1998 | Swartz et al. |
| 5,716,389 | A | | 2/1998 | Walinsky et al. |
| 5,718,231 | A | | 2/1998 | Dewhurst et al. |
| 5,718,241 | A | | 2/1998 | Ben-Haim et al. |
| 5,718,701 | A | | 2/1998 | Shai et al. |
| 5,720,775 | A | | 2/1998 | Larnard |
| 5,722,401 | A | | 3/1998 | Pietroski et al. |
| 5,722,403 | A | | 3/1998 | McGee |
| 5,722,963 | A | | 3/1998 | Lurie et al. |
| 5,725,494 | A | | 3/1998 | Brisken |
| 5,725,512 | A | | 3/1998 | Swartz et al. |

| | | |
|---|---|---|
| 5,728,062 A | 3/1998 | Brisken |
| 5,730,127 A | 3/1998 | Avitall |
| 5,730,704 A | 3/1998 | Avitall |
| 5,733,315 A | 3/1998 | Burdette et al. |
| 5,735,280 A | 4/1998 | Sherman et al. |
| 5,735,811 A | 4/1998 | Brisken |
| 5,735,846 A | 4/1998 | Panescu et al. |
| 5,741,249 A | 4/1998 | Moss et al. |
| 5,741,320 A | 4/1998 | Thornton et al. |
| 5,743,870 A | 4/1998 | Edwards |
| 5,743,903 A | 4/1998 | Stern et al. |
| 5,749,880 A | 5/1998 | Banas et al. |
| 5,755,663 A | 5/1998 | Larsen et al. |
| 5,755,664 A | 5/1998 | Rubenstein |
| 5,755,715 A | 5/1998 | Stern et al. |
| 5,755,760 A | 5/1998 | Maguire et al. |
| 5,769,846 A | 6/1998 | Edwards |
| 5,782,239 A | 7/1998 | Webster, Jr. |
| RE35,880 E | 8/1998 | Waldman et al. |
| 5,797,877 A | 8/1998 | Hamilton et al. |
| 5,797,903 A | 8/1998 | Swanson et al. |
| 5,797,905 A | 8/1998 | Fleischman et al. |
| 5,800,378 A | 9/1998 | Edwards et al. |
| 5,800,379 A | 9/1998 | Edwards |
| 5,800,413 A | 9/1998 | Swartz et al. |
| 5,800,428 A | 9/1998 | Nelson et al. |
| 5,800,429 A | 9/1998 | Edwards |
| 5,807,309 A | 9/1998 | Edwards |
| 5,807,391 A | 9/1998 | Wijkamp |
| 5,807,395 A | 9/1998 | Mulier et al. |
| 5,824,046 A | 10/1998 | Smith et al. |
| 5,846,218 A | 12/1998 | Brisken |
| 5,851,232 A | 12/1998 | Lois |
| 5,928,279 A | 7/1999 | Shannon et al. |
| 5,938,660 A | 8/1999 | Swartz |
| 5,971,983 A | 10/1999 | Lesh |
| 6,012,457 A * | 1/2000 | Lesh .................. 128/898 |
| 6,023,638 A | 2/2000 | Swanson |
| 6,024,739 A | 2/2000 | Ponzi |
| 6,024,740 A | 2/2000 | Lesh |
| 6,064,902 A | 5/2000 | Haissaguerre et al. |
| 6,071,279 A | 6/2000 | Whayne et al. |
| 6,071,281 A | 6/2000 | Burnside et al. |
| 6,117,101 A | 9/2000 | Diederich |
| 6,152,920 A | 11/2000 | Thompson |
| 6,176,842 B1 | 1/2001 | Tachibana et al. |
| 6,210,356 B1 | 4/2001 | Anderson et al. |
| 6,305,378 B1 | 10/2001 | Lesh |
| 6,383,151 B1 * | 5/2002 | Diederich et al. .......... 601/2 |
| 2001/0007940 A1 * | 7/2001 | Tu et al. .................. 606/41 |

FOREIGN PATENT DOCUMENTS

| | | |
|---|---|---|
| WO | WO 94/21165 | 9/1994 |
| WO | WO 94/21167 A1 | 9/1994 |
| WO | WO 94/21168 A1 | 9/1994 |
| WO | WO 95/10318 A1 | 4/1995 |
| WO | WO 95/10319 A1 | 4/1995 |
| WO | WO 95/10321 A1 | 4/1995 |
| WO | WO 95/19738 A1 | 7/1995 |
| WO | WO 96/00036 A1 | 1/1996 |
| WO | WO 96/10961 | 4/1996 |
| WO | WO 96/26675 | 9/1996 |
| WO | WO 96/32885 A1 | 10/1996 |
| WO | WO 96/32897 | 10/1996 |
| WO | WO 97/32525 | 9/1997 |
| WO | WO 97/37607 | 10/1997 |
| WO | WO 97/45156 A1 | 12/1997 |
| WO | WO 98/02201 | 1/1998 |
| WO | WO 98/26724 A1 | 6/1998 |
| WO | WO 98/49957 | 11/1998 |
| WO | WO 99/00064 | 1/1999 |
| WO | WO 99/00064 A1 | 1/1999 |
| WO | WO 99/02096 | 1/1999 |
| WO | WO 00/07508 | 2/2000 |

OTHER PUBLICATIONS

McMath LP et al., "Percutaneous Laser Balloon Coagulation of Accessory Pathways," Diagn Ther Cardiovasc Interven 1425:165–171 (1991).

Schuger CD et al., "Long–term Effects of Percutaneous Laser Balloon Ablation from the Canine Coronary Sinus," Circulation 86:947–954 (1992).

Sueda et al., "Simple Left Atrial Procedure for Chronic Atrial Fibrillation Associated With Mitral Valve Disease," (1996).

PCT Search Report for PCT/US01/15899.

Diederich, C.J., et al., "Induction of Hyperthremia Using an Intracavitary Multielement Ultrasonic Applicator," Transactions in Biomedical Engineering, vol. 36 No. 4 1989.

Diederich, et al., The Development of Intracavitary Ultrasonic Applicators for Hyperthermia: A Design and Experimental Study. Medical Physics, Jul./Aug. 1990.

Jais et al., "Biatrial Dimensions Relevant to Catheter Ablation," NASPE 17th Annual Scientific Sessions Abstract, Dec. 1995.

* cited by examiner

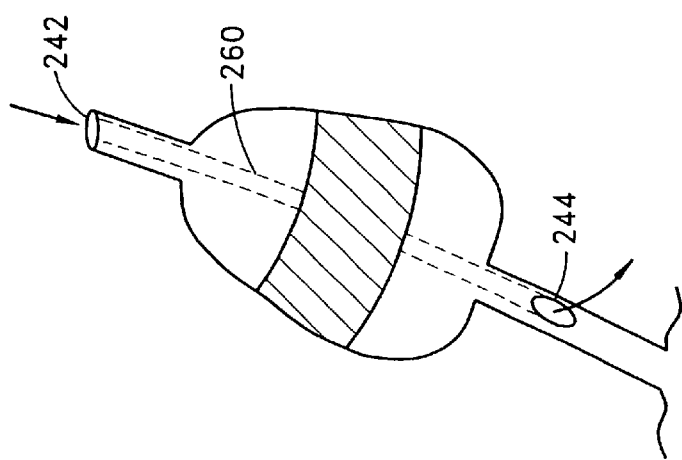
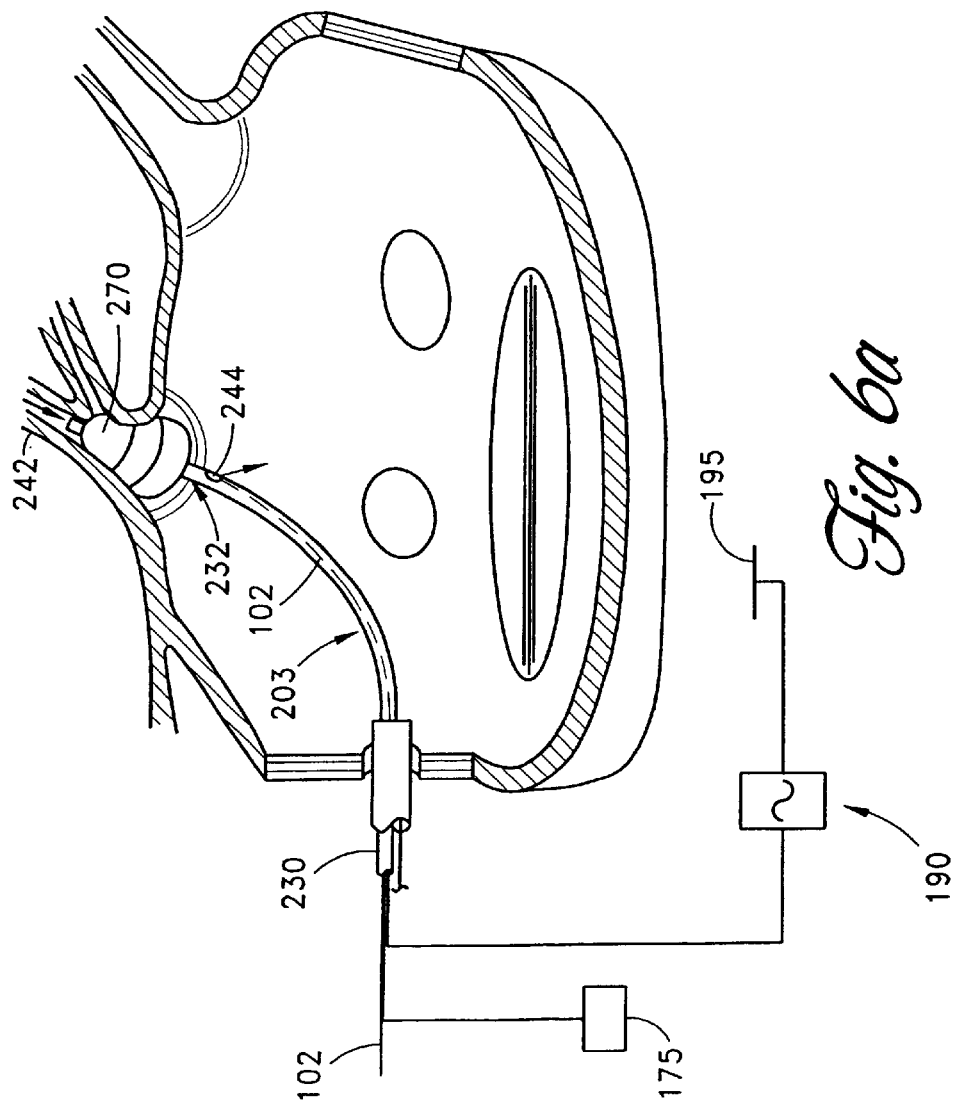
Fig. 6b
Fig. 6a

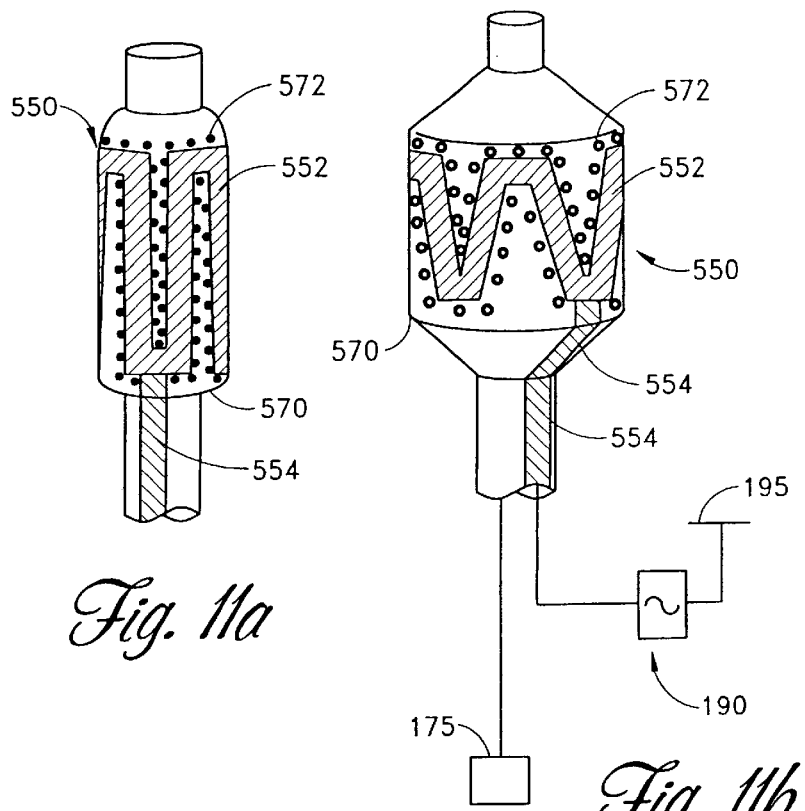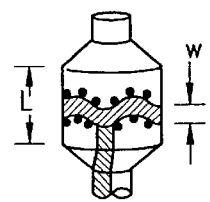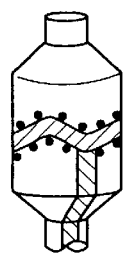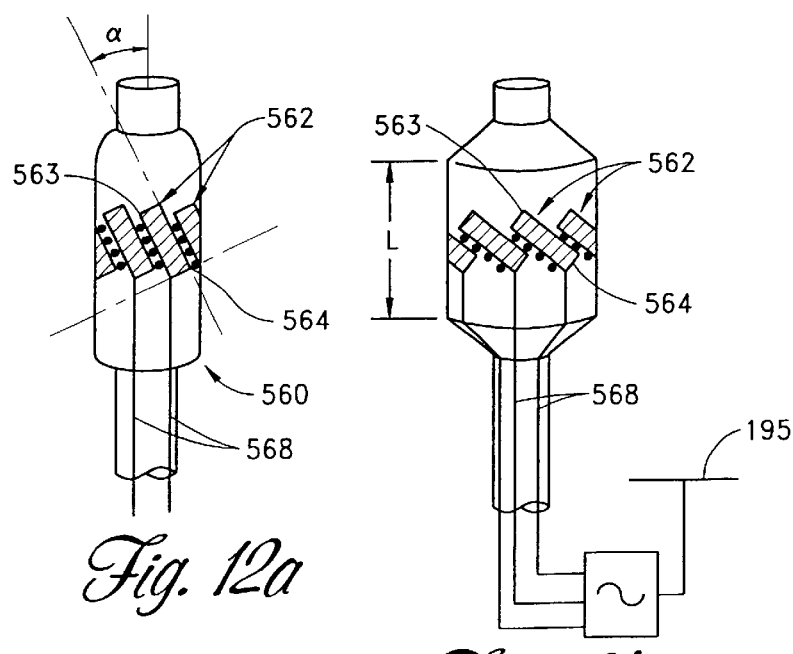

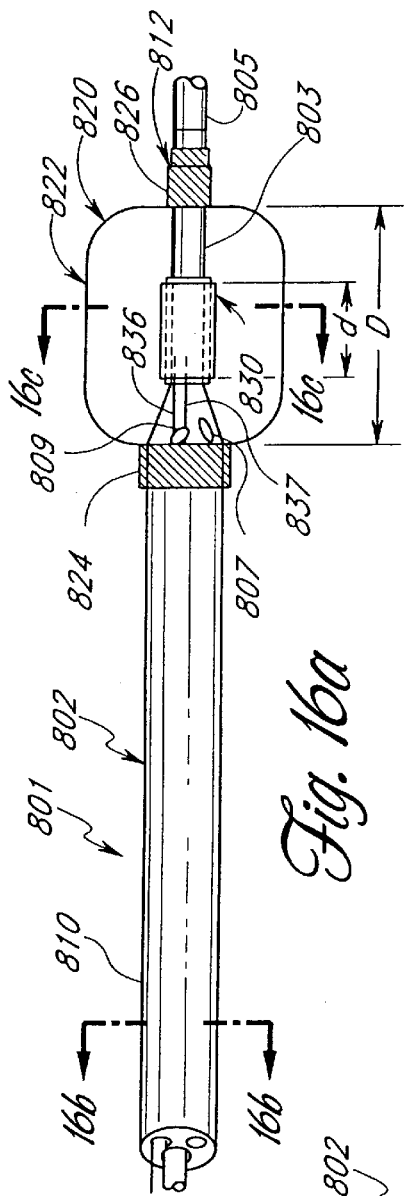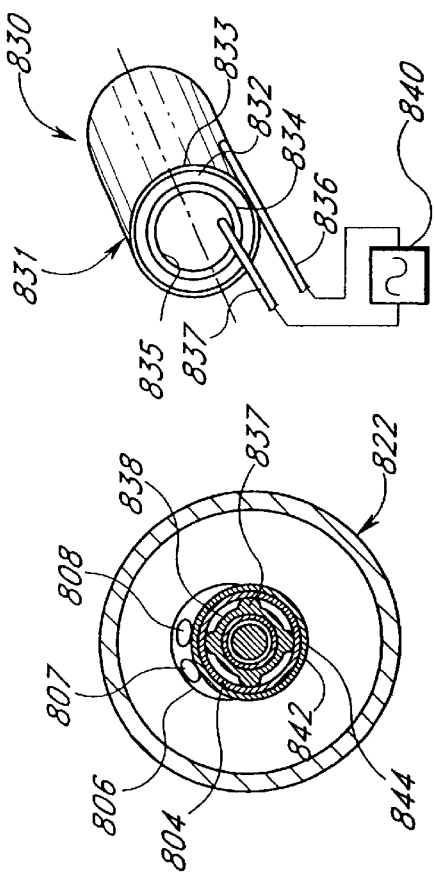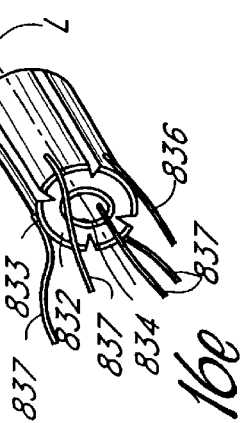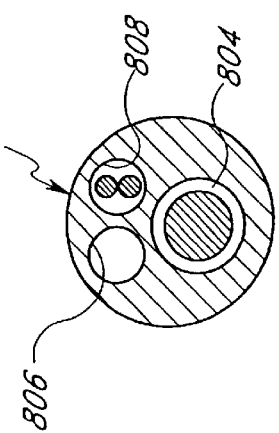

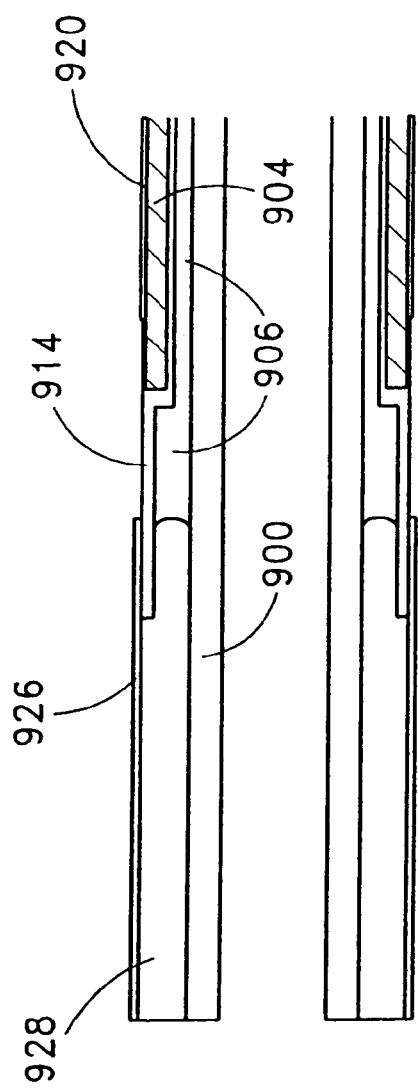

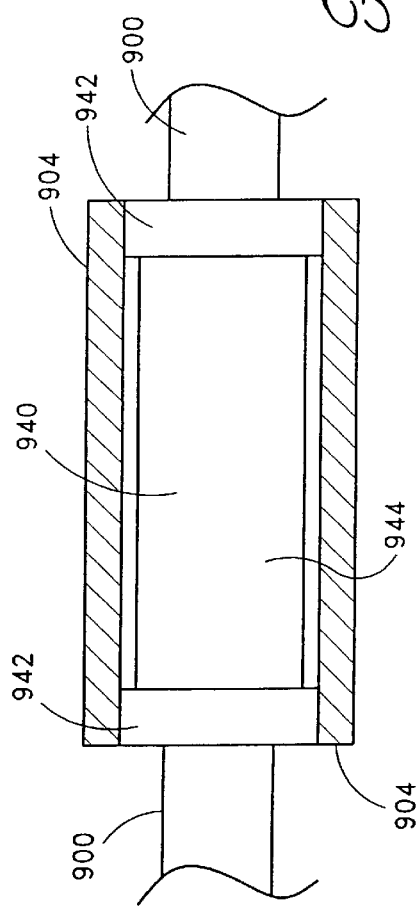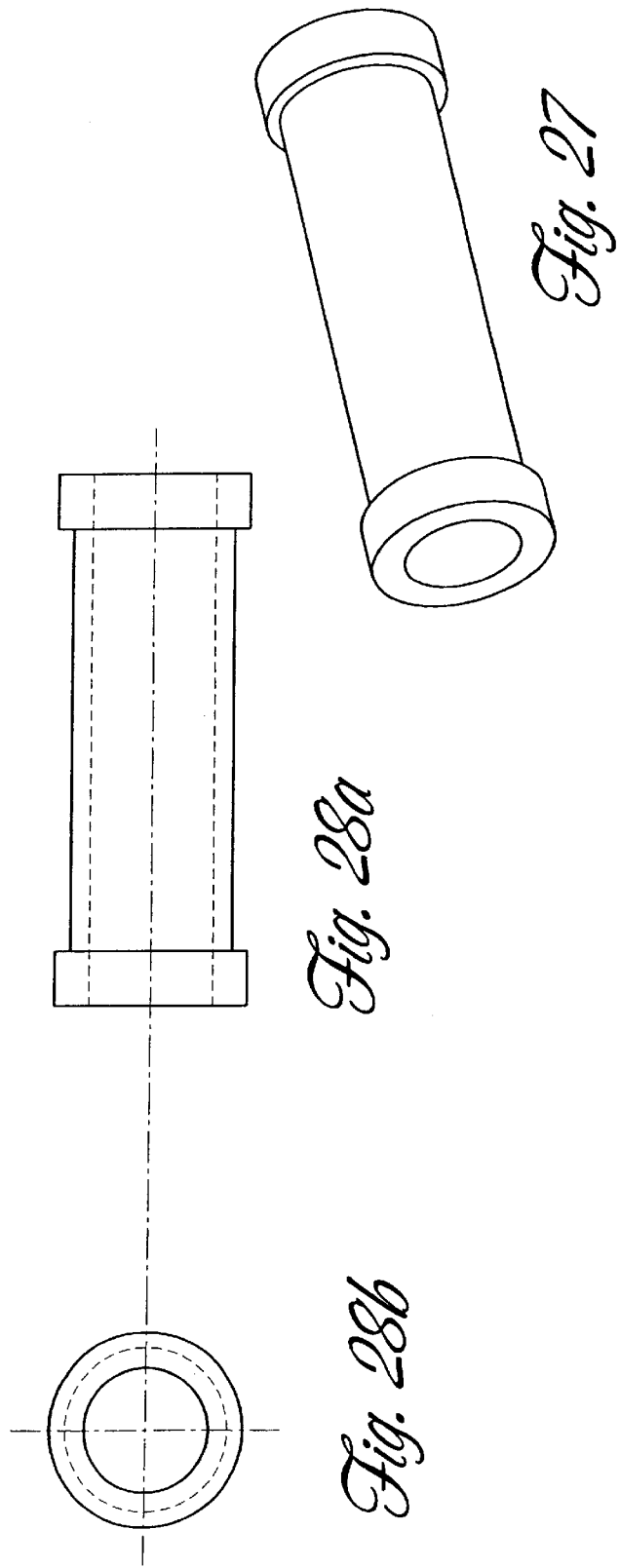

APPARATUS AND METHOD INCORPORATING AN ULTRASOUND TRANSDUCER ONTO A DELIVERY MEMBER

RELATED APPLICATIONS

The present application claims priority under 35 U.S.C. §119(e) to U.S. Provisional Application No. 60/204,912, filed May 16, 2000.

TECHNICAL FIELD

The present invention is a surgical device and method. More specifically, it is a surgical device and method which provides an ultrasound transducer assembly mounted on a catheter shaft for ultrasonically coupling to a region of tissue in a body of a patient, and still more specifically for ultrasonically coupling to a circumferential region of tissue at a location where a pulmonary vein extends from an atrium.

BACKGROUND OF THE INVENTION

The terms "body space," including derivatives thereof, is herein intended to mean any cavity or lumen within the body which is defined at least in part by a tissue wall. For example, the cardiac chambers, the uterus, the regions of the gastrointestinal tract, and the arterial or venous vessels are all considered illustrative examples of body spaces within the intended meaning.

The term "body lumen," including derivatives thereof, is herein intended to mean any body space which is circumscribed along a length by a tubular tissue wall and which terminates at each of two ends in at least one opening that communicates externally of the body space. For example, the large and small intestines, the vas deferens, the trachea, and the fallopian tubes are all illustrative examples of lumens within the intended meaning. Blood vessels are also herein considered lumens, including regions of the vascular tree between their branch points. More particularly, the pulmonary veins are lumens within the intended meaning, including the region of the pulmonary veins between the branched portions of their ostia along a left ventricle wall, although the wall tissue defining the ostia typically presents uniquely tapered lumenal shapes.

Many local energy delivery devices and methods have been developed for treating the various abnormal tissue conditions in the body, and particularly for treating abnormal tissue along the body space walls which define the various body spaces in the body. For example, various devices have been disclosed with the primary purpose of treating or recanalizing atherosclerotic vessels with localized energy delivery. Several disclosed devices and methods combine energy delivery assemblies in combination with cardiovascular stent devices in order to locally deliver energy to tissue in order to maintain patency in diseased lumens such as blood vessels. Endometriosis, another abnormal wall tissue condition which is associated with the endometrial cavity of the female and is characterized by dangerously proliferative uterine wall tissue along the surface of the endometrial cavity, has also been treated by local energy delivery devices and methods. Several other devices and methods have also been disclosed which use catheter-based heat sources for the intended purpose of inducing thrombosis and controlling hemorrhaging within certain body lumens such as vessels.

Further, more detailed examples of local energy delivery devices and related procedures such as those of the types just described above are variously disclosed in the following references: U.S. Pat. No. 4,672,962 to Hershenson; U.S. Pat. No. 4,676,258 to InoKuchi et al.; U.S. Pat. No. 4,790,311 to Ruiz; U.S. Pat. No. 4,807,620 to Strul et al.; U.S. Pat. No. 4,998,933 to Eggers et al.; U.S. Pat. No. 5,035,694 to Kasprzyk et al.; U.S. Pat. No. 5,190,540 to Lee; U.S. Pat. No. 5,226,430 to Spears et al.; and U.S. Pat. No. 5,292,321 to Lee; U.S. Pat. No. 5,449,380 to Chin; U.S. Pat. No. 5,505,730 to Edwards; U.S. Pat. No. 5,558,672 to Edwards et al.; and U.S. Pat. No. 5,562,720 to Stern et al.; U.S. Pat. No. 4,449,528 to Auth et al.; U.S. Pat. No. 4,522,205 to Taylor et al.; and U.S. Pat. No. 4,662,368 to Hussein et al.; U.S. Pat. No. 5,078,736 to Behl; and U.S. Pat. No. 5,178,618 to Kandarpa.

Other previously disclosed devices and methods electrically couple fluid to an ablation element during local energy delivery for treatment of abnormal tissues. Some such devices couple the fluid to the ablation element for the primary purpose of controlling the temperature of the element during the energy delivery. Other such devices couple the fluid more directly to the tissue-device interface either as another temperature control mechanism or in certain other known applications as an actual carrier for the localized energy delivery, itself.

More detailed examples of ablation devices which use fluid to assist in electrically coupling electrodes to tissue are disclosed in the following references: U.S. Pat. No. 5,348,554 to Imran et al.; U.S. Pat. No. 5,423,811 to Imran et al.; U.S. Pat. No. 5,505,730 to Edwards; U.S. Pat. No. 5,545,161 to Imran et al.; U.S. Pat. No. 5,558,672 to Edwards et al.; U.S. Pat. No. 5,569,241 to Edwards; U.S. Pat. No. 5,575,788 to Baker et al.; U.S. Pat. No. 5,658,278 to Imran et al.; U.S. Pat. No. 5,688,267 to Panescu et al.; U.S. Pat. No. 5,697,927 to Imran et al.; U.S. Pat. No. 5,722,403 to McGee et al.; U.S. Pat. No. 5,769,846; and PCT Patent Application Publication No. WO 97/32525 to Pomeranz et al.; and PCT Patent Application Publication No. WO 98/02201 to Pomeranz et al.

Cardiac Arrhythmias

Cardiac arrhythmias, and atrial fibrillation in particular, persist as common and dangerous medical ailments and are particularly prevalent among the aging population. A patient with cardiac arrhythmia has abnormal regions of cardiac tissue that do not follow the synchronous beating cycle associated with normally conductive tissue. Instead, the abnormal regions of cardiac tissue conduct aberrant signals to adjacent tissue, thereby disrupting the cardiac cycle and producing an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmia, may be of a multiwavelet reentrant type, characterized by multiple asynchronous loops of electrical impulses that are scattered about the atrial chamber and are often self-propagating. In the alternative or in addition to the multiwavelet reentrant type, cardiac arrhythmias may also have a focal origin, such as when an isolated region of tissue in an atrium fires autonomously in a rapid, repetitive fashion. Cardiac arrhythmias, including atrial fibrillation, may be generally detected using the global technique of an electrocardiogram (EKG). More sensitive procedures of mapping the specific conduction along the cardiac chambers have also been disclosed, such as, for example, in U.S. Pat. No. 4,641,649 to Walinsky et al. and Published PCT Patent Application No. WO 96/32897 to Desai.

A host of clinical conditions may result from the irregular cardiac function and resulting hemodynamic abnormalities associated with atrial fibrillation, including stroke, heart failure, and other thromboembolic events. In fact, atrial fibrillation is believed to be a significant cause of cerebral stroke, wherein the abnormal hemodynamics in the left atrium caused by the fibrillatory wall motion precipitate the formation of thrombus within the atrial chamber. A thromboembolism is ultimately dislodged into the left ventricle which thereafter pumps the embolism into the cerebral circulation where a stroke results. Accordingly, numerous procedures for treating atrial arrhythmias have been developed, including pharmacological, surgical, and catheter ablation procedures.

Several pharmacological approaches intended to remedy or otherwise treat atrial arrhythmias have been disclosed, such as for example according to the disclosures of the following references: U.S. Pat. No. 4,673,563 to Berne et al.; U.S. Pat. No. 4,569,801 to Molloy et al.; and also "Current Management of Arrhythmias" (1991) by Hindricks, et al. However, such pharmacological solutions are not generally believed to be entirely effective in many cases, and are even believed in some cases to result in proarrhythmia and long term inefficacy.

Several surgical approaches have also been developed with the intention of treating atrial fibrillation. One particular example is known as the "maze procedure," as is disclosed by Cox, J L et al. in "The surgical treatment of atrial fibrillation. I. Summary" *Thoracic and Cardiovascular Surgery* 101(3), pp. 402–405 (1991); and also by Cox, J L in "The surgical treatment of atrial fibrillation. IV. Surgical Technique", *Thoracic and Cardiovascular Surgery* 101(4), pp. 584–592 (1991). In general, the "maze" procedure is designed to relieve atrial arrhythmia by restoring effective atrial systole and sinus node control through a prescribed pattern of incisions about the tissue wall. In the early clinical experiences reported, the "maze" procedure included surgical incisions in both the right and the left atrial chambers. However, more recent reports predict that the surgical "maze" procedure may be substantially efficacious when performed only in the left atrium, such as is disclosed in Sueda et al., "Simple Left Atrial Procedure for Chronic Atrial Fibrillation Associated With Mitral Valve Disease" (1996).

The "maze procedure" as performed in the left atrium generally includes forming vertical incisions from the two superior pulmonary veins and terminating in the region of the mitral valve annulus, traversing the region of the inferior pulmonary veins en route. An additional horizontal line also connects the superior ends of the two vertical incisions. Thus, the atrial wall region bordered by the pulmonary vein ostia is isolated from the other atrial tissue. In this process, the mechanical sectioning of atrial tissue eliminates the arrhythmogenic conduction from the boxed region of the pulmonary veins and to the rest of the atrium by creating conduction blocks within the aberrant electrical conduction pathways. Other variations or modifications of this specific pattern just described have also been disclosed, all sharing the primary purpose of isolating known or suspected regions of arrhythmogenic origin or propagation along the atrial wall.

While the "maze" procedure and its variations as reported by Cox and others have met some success in treating patients with atrial arrhythmia, its highly invasive methodology is believed to be prohibitive in most cases. However, these procedures have provided a guiding principle that electrically isolating faulty cardiac tissue may successfully prevent atrial arrhythmia, and particularly atrial fibrillation caused by arrhythmogenic conduction arising from the region of the pulmonary veins.

Less invasive catheter-based approaches to treat atrial fibrillation have been disclosed which implement cardiac tissue ablation for terminating arrhythmogenic conduction in the atria. Examples of such catheter-based devices and treatment methods have generally targeted atrial segmentation with ablation catheter devices and methods adapted to form linear or curvilinear lesions in the wall tissue which defines the atrial chambers. Some specifically disclosed approaches provide ablation elements that are linear over a defined length and are intended to engage the tissue for creating the linear lesion. Other disclosed approaches provide shaped or steerable guiding sheaths, or sheaths within sheaths, for the intended purpose of directing tip ablation catheters toward the posterior left atrial wall such that sequential ablations along the predetermined path of tissue may create the desired lesion. In addition, various energy delivery modalities have been disclosed for forming atrial wall lesions, and include use of microwave, laser, ultrasound, thermal conduction, and more commonly, radiofrequency energies to create conduction blocks along the cardiac tissue wall.

Further more detailed examples of ablation device assemblies and methods for creating lesions along an atrial wall are disclosed in the following U.S. patent references: U.S. Pat. No. 4,898,591 to Jang et al.; U.S. Pat. No. 5,104,393 to Isner et al.; U.S. Pat. No. 5,427,119; U.S. Pat. No. 5,487,385 to Avitall; U.S. Pat. No. 5,545,193 to Fleischman et al.; U.S. Pat. No. 5,549,661 to Kordis et al.; U.S. Pat. No. 5,575,810 to Swanson et al.; U.S. Pat. No. 5,564,440 to Swartz et al.; U.S. Pat. No. 5,575,766 to Swartz et al.; U.S. Pat. No. 5,582,609 to Swanson; U.S. Pat. No. 5,617,854 to Munsif; U.S. Pat. No. 5,687,723 to Avitall; U.S. Pat. No. 5,702,438 to Avitall.

Other examples of such ablation devices and methods are disclosed in the following Published PCT Patent Applications: WO 93/20767 to Stem et al.; WO 94/21165 to Kordis et al.; WO 96/10961 to Fleischman et al.; WO 96/26675 to Klein et al.; and WO 97/37607 to Schaer.

Additional examples of such ablation devices and methods are disclosed in the following published articles: "Physics and Engineering of Transcatheter Tissue Ablation", Avitall et al., *Journal of American College of Cardiology*, Volume 22, No. 3:921–932 (1993); and "Right and Left Atrial Radiofrequency Catheter Therapy of Paroxysmal Atrial Fibrillation," Haissaguerre, et al., *Journal of Cardiovascular Electrophysiology* 7(12), pp. 1132–1144 (1996).

In addition to the known assemblies summarized above, additional tissue ablation device assemblies have also been recently developed for the specific purpose of ensuring firm contact and consistent positioning of a linear ablation element along a length of tissue. These assemblies anchor the element at one or more predetermined locations along the length of tissue, such as in order to form a "maze"-type lesion pattern in the left atrium. One example assembly includes an anchor at each of two ends of a linear ablation element. The anchors are used to secure the ends to each of two predetermined locations along a left atrial wall, such as at two adjacent pulmonary veins, so that tissue may be ablated along the length of tissue extending therebetween.

In addition to attempting atrial wall segmentation with long linear lesions for treating atrial arrhythmia, other ablation devices and methods have also been disclosed which are intended to use expandable members such as balloons to ablate cardiac tissue. Some such devices have been disclosed primarily for use in ablating tissue wall regions along the cardiac chambers. Other devices and methods have been disclosed for treating abnormal conduction of the left-sided accessory pathways, and in particular associated with "Wolff-Parkinson-White" syndrome—various such disclosures use a balloon for ablating from within a region of an associated coronary sinus adjacent to the desired cardiac tissue to ablate. Further more detailed examples of devices and methods such as of the types just described are variously disclosed in the following published references: Fram et al., in "Feasibility of RF Powered Thermal Balloon Ablation of Atrioventricular Bypass Tracts via the Coronary Sinus: In vivo Canine Studies," *PACE*, Vol. 18, p 1518–1530 (1995); "Long-term effects of percutaneous laser balloon ablation from the canine coronary sinus", Schuger C D et al., *Circulation* (1992) 86:947–954; and "Percutaneous laser balloon coagulation of accessory pathways", McMath L P et al., Diagn Ther Cardiovasc Interven 1991; 1425:165–171.

Cardiac Arrhythmias Originating from Foci in Pulmonary Veins

As discussed above, some modes of atrial fibrillation are focal in nature, caused by the rapid and repetitive firing of an isolated center within cardiac muscle tissue associated with the atrium. Such foci may act as either a trigger of atrial fibrillatory paroxysmal or may even sustain the fibrillation. Various disclosures have suggested that focal atrial arrhythmia often originates from at least one tissue region along one or more of the pulmonary veins of the left atrium, and even more particularly in the superior pulmonary veins.

Less-invasive percutaneous catheter ablation techniques have been disclosed which use end-electrode catheter designs with the intention of ablating and thereby treating focal arrhythmias in the pulmonary veins. These ablation procedures are typically characterized by the incremental application of electrical energy to the tissue to form focal lesions designed to terminate the inappropriate arrhythmogenic conduction.

One example of a focal ablation method intended to treat focal arrhythmia originating from a pulmonary vein is disclosed by Haissaguerre, et al. in "Right and Left Atrial Radiofrequency Catheter Therapy of Paroxysmal Atrial Fibrillation" in *Journal of Cardiovascular Electrophysiology* 7(12), pp. 1132–1144 (1996). Haissaguerre, et al. discloses radiofrequency catheter ablation of drug-refractory paroxysmal atrial fibrillation using linear atrial lesions complemented by focal ablation targeted at arrhythmogenic foci in a screened patient population. The site of the arrhythmogenic foci were generally located just inside the superior pulmonary vein, and the focal ablations were generally performed using a standard 4 mm tip single ablation electrode.

Another focal ablation method of treating atrial arrhythmias is disclosed in Jais et al., "A focal source of atrial fibrillation treated by discrete radiofrequency ablation," *Circulation* 95:572–576 (1997). Jais et al. discloses treating patients with paroxysmal arrhythmias originating from a focal source by ablating that source. At the site of arrhythmogenic tissue, in both right and left atria, several pulses of a discrete source of radiofrequency energy were applied in order to eliminate the fibrillatory process.

Other assemblies and methods have been disclosed addressing focal sources of arrhythmia in pulmonary veins by ablating circumferential regions of tissue either along the pulmonary vein, at the ostium of the vein along the atrial wall, or encircling the ostium and along the atrial wall. More detailed examples of device assemblies and methods for treating focal arrhythmia as just described are disclosed the following references: U.S. Pat. No. 6,117,101 to Diederich et al.; U.S. Pat. No. 6,024,740 to Lesh et al.; U.S. Pat. No. 6,012,457 to Lesh; U.S. Pat. No. 6,305,378 to Lesh; and U.S. Ser. Nos. 09/642,251 entitled "Device and Method for Forming a Circumferential Conduction Block in a Pulmonary Vein" to Michael D. Lesh. The disclosures of these references are herein incorporated in their entirety by reference thereto.

Another specific device assembly and method which is intended to treat focal atrial fibrillation by ablating a circumferential region of tissue between two seals in order to form a conduction block to isolate an arrhythmogenic focus within a pulmonary vein is disclosed in U.S. Pat. No. 5,938,660 to Swartz et al. and a related Published PCT Patent Application No. WO 99/00064.

In particular, certain tissue ablation device assemblies that incorporate ultrasound energy sources have been observed to be highly efficient and effective for ablating circumferential regions of tissue where pulmonary veins extend from atria. However, the efficiency of ultrasonic output from such a source has been observed to be directly related to the structural coupling of the transducer to the underlying delivery member or catheter shaft. The transducer output is damped whenever it is in contact with any sort of mounting means between the back or inner side of the transducer and the catheter shaft, even according to known modes using elastomeric mounting structures sandwiched between the transducer and the shaft. Several known ultrasound transducer mounting examples provide support structures that extend between the transducer and the underlying support member, such that for example the transducer rests on the support member which rests on the delivery member. Further more detailed examples of such ultrasound transducer support structures are disclosed in the following references: U.S. Pat. No. 5,606,974 to Castellano; and U.S. Pat. No. 5,620,479 to Diederich. Further examples of structural support designs for ultrasound transducers on catheter shafts are disclosed in published PCT Patent Application PCT/US98/09554 (WO98/49957) to Diederich et al.

Further to the previously disclosed ultrasound transducer mounting structures and arrangements, it is desirable for the mounting structure to provide sufficient support and positioning for the transducer. It is also desirable that such a mounting structure provides for air backing between the transducer and the underlying delivery shaft in order to isolate ultrasound transmission radially away from the catheter shaft and toward tissue surrounding the shaft. It has been observed that such air backing helps prevent heat build-up in the region, as the vibrational ultrasound energy has been observed to superheat other materials in contact therewith which absorb the energy (airbacking actually reflects the energy radially outwardly as desired). Therefore, such air backing is particularly desirable for high operational powers associated with therapeutic ultrasound ablation transmission. It is also desirable that such a mounting structure adequately supports the transducer while minimizing the vibrational damping of the transducer during operation. The present invention addresses these desires.

SUMMARY OF THE INVENTION

The present invention provides various improved catheter constructions and associated methods of manufacture for mounting an ultrasound transducer onto a catheter shaft while minimizing the damping of the transducer associated with the structural coupling. In several of the construction variations, the transducer is suspended about an inner member (e.g., the catheter body) absent any support structure between the catheter and the transducer along the length of the transducer. That is, transducer mounting is accomplished without the use of internal mounting members and/or elastic member in the space between the inner member and the transducer. Such mounting arrangements support the transducer and are attached to the inner member (or to an assembly of members) at points proximal and distal of the ultrasound transducer.

In one mode of the present invention, an ultrasound ablation apparatus is provided with reduced transducer damping. The apparatus comprises an elongate catheter body having proximal and distal end portions, an outer wall and an outer diameter; a cylindrical ultrasound transducer coaxially disposed over the catheter body, the ultrasound transducer having proximal and distal end portions, an inner wall and an inner diameter which is greater than the outer diameter of the catheter body. Consequently, an air gap is provided in a radial separation between the inner wall of the ultrasound transducer and the catheter body. The apparatus also includes a support structure for suspending the ultrasound transducer in a substantially fixed coaxial position relative to the catheter body. The support structure contacts the outer wall of the catheter body at locations proximal and distal to the proximal and distal end portions of the ultrasound transducer, respectively. Accordingly, the support structure holds the ultrasound transducer without contacting the inner wall of the ultrasound transducer, thereby maintaining the radial separation while reducing transducer damping.

In one preferred mode of the ultrasound ablation apparatus, the ultrasound transducer is shaped to ablate a circumferential region of tissue. The transducer may include at least one transmissive panel.

In another aspect of the ultrasound ablation apparatus, at least a substantial portion of the radial separation is sealed by the support structure to prevent external fluids from entering the radial separation. A gas may be sealed within the radial separation. Alternatively, a liquid maybe sealed within the radial separation.

The ultrasound ablation apparatus of the present invention may include first and second flanges extending axially from the proximal and distal end portions of the ultrasound transducer, respectively, the support structure being coupled to the first and second flanges. The support structure may comprise first and second elastomeric O-rings disposed on the catheter body such that the first and second O-rings engage the first and second flanges. In a variation of this mode, the support structure may comprises first and second sleeves disposed on the catheter body and fitted over the first and second flanges, to secure the ultrasound transducer relative to the catheter body. In another variation, the support structure may comprise first and second splines disposed on the catheter body such that the first and second splines engage the first and second flanges. Alternatively, the support structure may comprise first and second annular members disposed along the catheter body such that the first and second annular members engage the first and second flanges.

In another aspect of the present invention, the support structure may comprise first and second annular members disposed on the catheter body, wherein the first and second annular members frictionally engage the proximal and distal end portions of the ultrasound transducer. The support structure could also comprise a shrink-wrap cover layer disposed around the ultrasound transducer.

In one preferred embodiment, the ultrasound ablation apparatus of the present invention may include an expandable member adapted to engage a circumferential region of tissue. In this mode, the ultrasound transducer is located inside the expandable member and acoustically coupled to the expandable member. The expandable member may be an inflatable balloon.

In a variation to the expandable member embodiment, the ultrasound ablation apparatus may also have a cooling chamber between the ultrasound transducer and the expandable member. The cooling chamber is adapted to allow a cooling fluid to flow over said ultrasound transducer. Further, this mode may include a source of pressurized cooling fluid and a cooling fluid lumen in the catheter body. The lumen may have a distal port opening into the cooling chamber. The ultrasound ablation apparatus may also incorporate a thermocouple for monitoring temperature along at least a portion of the circumferential region of tissue engaged by the expandable member.

The ultrasound ablation apparatus of the present invention may also include at least one electrical lead coupled to the ultrasound transducer.

In a variation of the mounting structure, the apparatus may comprise fillets located proximal and distal to proximal and distal end portions of the ultrasound transducer for sealing the radial separation from entry of external fluids and providing a smooth surface for insertion of said ultrasound ablation apparatus into a body structure.

In another variation, the ultrasound ablation apparatus may include a guidewire lumen extending through at least a portion of the catheter body for slidably engaging a guidewire.

In another variation to the present invention, the appartus may comprise an elongate catheter body; and an cylindrical ultrasound transducer having first and second ends and inner and outer surfaces. The ultrasound transducer is mounted coaxially on the catheter body such that a radial separation is provided between the ultrasound transducer and the catheter body for mechanically isolating the ultrasound transducer from the catheter body. In this mode, the support structure is coupled to the ultrasound transducer and the catheter body to maintain at least a region of the radial separation for reducing acoustic damping caused by the support structure.

In variations to this mode, annular end members may be provided with a metallic exterior surface adapted to engage the inner surface of the ablation element. This mounting mode may also include an annular intermediate portion, located between the first and second annular members and the catheter body.

In another variation, the support structure may comprise a substantially tubular member disposed over the catheter body. The tubular member has proximal and distal end regions and an intermediate region. The proximal and distal end regions are formed with a larger diameter than the intermediate region. The ultrasound transducer is disposed over the intermediate region such that it is axially contained by the proximal and distal end regions.

In another variation, the support structure may comprise at least one mandrel extending axially along the catheter body The at least one mandrel engages the catheter body and the inner surface of the ultrasound ablation element. The at least one mandrel may be a polyimide tube. More preferably, the at least one mandrel comprises a plurality of polyimide tubes positioned substantially uniformly around the catheter body within the radial separation.

In another variation, the support structure may comprise a braided metal tubular member disposed around the catheter body such that the radial separation is maintained therebetween. The ultrasound transducer is mounted coaxially over the braided tubular member. Alternatively, the support structure may include two braided metal tubular members disposed around the catheter body with an axial gap therebetween. The ultrasound transducer may be mounted to the braided tubular members thereby bridging the axial gap.

In another aspect of the invention, the support structure may comprise two truncated conical members, each having a first end with a large diameter and a second end with a small diameter. The conical members are disposed over the catheter body such that the first ends face inward and the second ends face outward. The inner surface of the ultrasound transducer is engaged by the first ends of the conical members.

In accordance with another mode of the invention, the support structure may comprise an expandable member disposed over the catheter body and having an outer surface. The inner surface of the ultrasound transducer may then be coaxially engaged by the outer surface of the expandable member.

The modes of the invention are generally adapted to capture air, or another gas as would be apparent to one of ordinary skill, within the mounting structures in order to "air back" the transducer. That is, these modes of suspension maintain an air gap between the transducer and the catheter shaft in order to maximize radially outward propagation of the ultrasound waves, as introduced above. In addition, the air space desirably is sealed to prevent fluid infiltration, be it blood or another fluid.

According to further beneficial modes, the ultrasound transducer apparatus and method modes just summarized are applied in a circumferential ablation device assembly which is adapted to couple to and ablate a circumferential region of tissue at a location where a pulmonary vein extends from an atrium. Moreover, the modes described for use with a circumferential ultrasound transducer may also be adapted for use with non-circumferential types of transducers, such as incorporating panel transducers that also benefit by being air backed without mounting members physically located and extending between such transducers and an underlying catheter shaft.

For purposes of summarizing the invention and the advantages achieved over the prior art, certain objects and advantages of the invention have been described above and are described below. Of course, it is to be understood that not necessarily all such objects or advantages may be achieved in accordance with any particular mode of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed. In addition, further aspects, advantages and features of the invention will become apparent from the following descriptions of the preferred modes of incorporating an ultrasound transducer onto a delivery element.

BRIEF DESCRIPTION OF THE DRAWINGS

FIG. 6A shows a similar perspective view as shown in FIG. 5, although showing a further circumferential ablation catheter variation which is adapted to allow for blood perfusion from the pulmonary vein and into the atrium while performing the circumferential ablation method shown diagrammatically in FIG. 3.

FIG. 6B is an enlarged partial view of the circumferential ablation catheter shown in FIG. 6A, with a perfusion lumen shown in phantom.

FIGS. 8A–B show perspective views of another circumferential ablation catheter variation during use in a left atrium according to the method of FIG. 3, wherein FIG. 8A shows a radially compliant expandable member with a working length adjusted to a radially expanded position while in the left atrium, and FIG. 8B shows the expandable member after advancing it into and engaging a pulmonary vein ostium while in the radially expanded position.

FIGS. 11A–B show perspective views of another circumferential ablation member variation for use in a circumferential ablation device assembly for pulmonary vein isolation, showing a circumferential ablation electrode circumscribing the working length of an expandable member with a secondary shape along the longitudinal axis of the working length which is a modified step shape, the expandable member being shown in a radially collapsed position and also in a radially expanded position, respectively.

FIGS. 11C–D show perspective views of two circumferential ablation electrodes which form equatorial or otherwise circumferentially placed bands that circumscribe the working length of an expandable member and that have serpentine and sawtooth secondary shapes, respectively, relative to the longitudinal axis of the expandable member when adjusted to a radially expanded position.

FIGS. 12A–B show perspective views of another circumferential ablation element which includes a plurality of individual ablation electrodes that are spaced circumferentially to form an equatorial band which circumscribes the working length of an expandable member either in an equatorial location or an otherwise circumferential location that is bounded both proximally and distally by the working length, and which are adapted to form a continuous circumferential lesion while the working length is adjusted to a radially expanded position.

FIG. 16A shows a longitudinal cross-sectional view of another circumferential ablation catheter, and shows the ablation element to include a single cylindrical ultrasound transducer which is positioned along an inner member within an expandable balloon which is further shown in a radially expanded condition.

FIG. 16B shows a transverse cross-sectional view of the circumferential ablation catheter shown in FIG. 16A taken along line 16B—16B shown in FIG. 16A.

FIG. 16C shows a transverse cross-sectional view of the circumferential ablation catheter shown in FIG. 16A taken along line 16C—16C shown in FIG. 16A.

FIG. 16D shows a perspective view of the ultrasonic transducer of FIG. 16A in isolation.

FIG. 16E shows a modified version of the ultrasonic transducer of FIG. 16D with individually driven sectors.

FIG. 21B shows the transducer in a molded shell in transverse section along plane B—B of FIG. 21A.

FIG. 22 shows another variation of the mounting design having a support sleeve and shrink-wrap cover.

FIG. 26 is a partial cross-sectional view of a transducer supported on a support member that is mounted on a tracking member of a catheter assembly.

FIG. 27 is a perspective view of the support illustrated in FIG. 26.

FIG. 28A is a side view of the support of FIG. 27.

FIG. 28B is a end view of the support of FIG. 27.

DETAILED DESCRIPTION OF THE PREFERRED EMBODIMENTS

Figure 1:
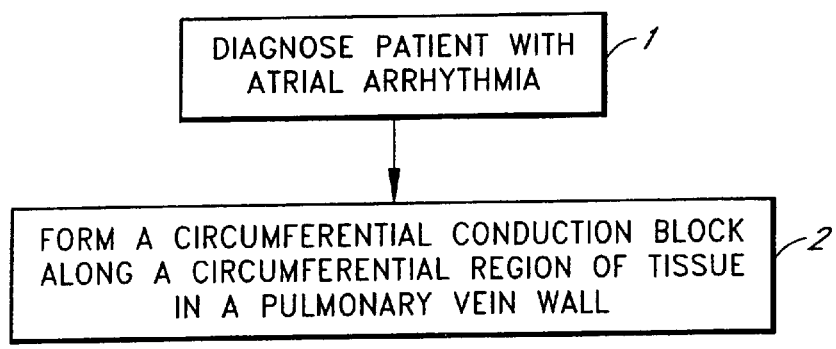
FIG. 1 diagrammatically shows sequential, general steps for treating atrial arrhythmia.

As will be described with reference to the detailed embodiments below, the modes for mounting a circumferential ultrasound ablation element to a catheter shaft according to the present invention are believed to be well-suited for use in a circumferential ablation device assembly. This device is particularly well-suited for treating patients with atrial arrhythmia by ablating a circumferential region of tissue at a location where a pulmonary vein extends from an atrium. Specifically, this device can be advantageously used to treat atrial arrhythmia by ablating a circumferential region of tissue at a location (a) where cardiac tissue extends up into the vein, (b) along the vein's ostium along the atrial wall, or (c) along the atrial wall and surrounding the vein's ostium. By ablating such a circumferential region of tissue, a circumferential conduction block is formed which either isolates the atrium from an arrhythmogenic focus upstream of the conduction block relative to the vein, or ablates the focus.

This circumferential pulmonary vein ablation aspect of the invention is therefore also well-suited for use in combination or aggregation with, or where appropriate in substitution for, the various features and embodiments disclosed in the following references that also address circumferential ablation at a location where a pulmonary vein extends from an atrium: U.S. Pat. No. 6,024,740 to Lesh et al.; U.S. Pat. No. 6,012,457 to Lesh; U.S. Pat. No. 6,117,101 to Diederich; U.S. Pat. No. 6,305,378 to Lesh; and U.S. Ser. Nos. 09/642,251 entitled "DEVICE AND METHOD FOR FORMING A CIRCUMFERENTIAL CONDUCTION BLOCK IN A PULMONARY VEIN" to Lesh. The disclosures of these references are herein incorporated in their entirety by reference thereto. For the purpose of further illustration, particular embodiments for pulmonary vein isolation that are known in the art are shown and described by reference to FIGS. 1–19B, with the related method of treatment broadly illustrated in diagrammatical form in the flow diagram of FIG. 1.

The terms "circumference" or "circumferential", including derivatives thereof, are herein intended to mean a continuous path or line which forms an outer border or perimeter that surrounds and thereby defines an enclosed region of space. Such a continuous path starts at one location along the outer border or perimeter, and translates along the outer border or perimeter until it is completed at the original starting location to enclose the defined region of space. The related term "circumscribe," including derivatives thereof, is herein intended to mean to enclose, surround, or encompass a defined region of space. Therefore, according to these defined terms, a continuous line which is traced around a region of space and which starts and ends at the same location "circumscribes" the region of space and has a "circumference" which is defined by the distance the line travels as it translates along the path circumscribing the space.

Still further, a circumferential path or element may include one or more of several shapes, and may be, for example, circular, oblong, ovular, elliptical, or otherwise planar enclosures. A circumferential path may also be three dimensional, such as, for example, two opposite-facing semi-circular paths in two different parallel or off-axis planes which are connected at their ends by line segments bridging between the planes.

Figure 2A:
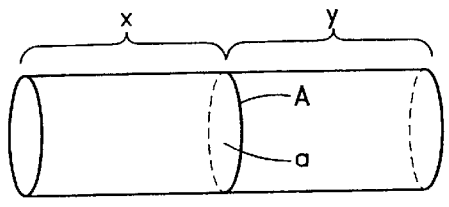
FIGS. 2A–E show schematic, perspective views of various exemplifying circumferential conduction blocks formed in pulmonary vein wall tissue with a circumferential ablation device assembly.
Figure 2B:
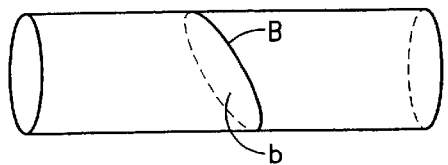
Figure 2C:
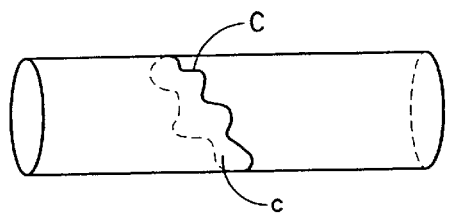
Figure 2D:
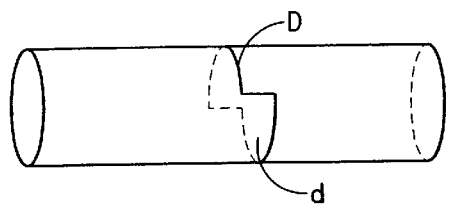
Figure 2E:
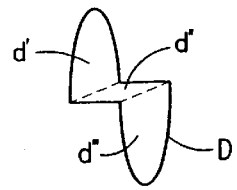

For purpose of further illustration, FIGS. 2A–D therefore show various circumferential paths A, B, C, and D, respectively, each translating along a portion of a pulmonary vein wall and circumscribing a defined region of space, shown at a, b, c, and d also respectively, each circumscribed region of space being a portion of a pulmonary vein lumen. For still further illustration of the three-dimensional circumferential case shown in FIG. 2D, FIG. 2E shows an exploded perspective view of circumferential path D as it circumscribes multiplanar portions of the pulmonary vein lumen shown at d', d", and d'", which together make up region d as shown in FIG. 2D.

The term "transect", including derivatives thereof, is also herein intended to mean to divide or separate a region of space into isolated regions. Thus, each of the regions circumscribed by the circumferential paths shown in FIGS. 2A–D transects the respective pulmonary vein, including its lumen and its wall, to the extent that the respective pulmonary vein is divided into a first longitudinal region located on one side of the transecting region, shown, for example, at region "X" in FIG. 2A, and a second longitudinal region on the other side of the transecting plane, shown, for example, at region "Y" also in FIG. 2A.

Therefore, a "circumferential conduction block" according to the present invention is formed along a region of tissue which follows a circumferential path along the pulmonary vein wall, circumscribing the pulmonary vein lumen and transecting the pulmonary vein relative to electrical conduction along its longitudinal axis. The transecting circumferential conduction block therefore isolates electrical conduction between opposite longitudinal portions of the pulmonary wall relative to the conduction block and along the longitudinal axis.

The terms "ablate" or "ablation," including derivatives thereof, are hereafter intended to mean the substantial altering of the mechanical, electrical, chemical, or other structural nature of tissue. In the context of intracardiac ablation applications shown and described with reference to the variations of the illustrative embodiment below, "ablation" is intended to mean sufficient altering of tissue properties to substantially block conduction of electrical signals from or through the ablated cardiac tissue.

The term "element" within the context of "ablation element" is herein intended to mean a discrete element, such as an electrode, or a plurality of discrete elements, such as a plurality of spaced electrodes, which are positioned so as to collectively ablate a region of tissue.

Therefore, an "ablation element" according to the defined terms may include a variety of specific structures adapted to ablate a defined region of tissue. For example, one suitable ablation element for use in the present invention may be formed, according to the teachings of the embodiments below, from an "energy emitting" type which is adapted to emit energy sufficient to ablate tissue when coupled to and energized by an energy source. Suitable "energy emitting" ablation elements for use in the present invention may therefore include, for example: an electrode element adapted to couple to a direct current ("DC") or alternating current ("AC") current source, such as a radiofrequency ("RF") current source; an antenna element which is energized by a microwave energy source; a heating element, such as a metallic element or other thermal conductor which is energized to emit heat such as by convective or conductive heat transfer, by resistive heating due to current flow, or by optical heating with light; a light emitting element, such as a fiber optic element which transmits light sufficient to ablate tissue when coupled to a light source; or an ultrasonic element such as an ultrasound crystal element which is adapted to emit ultrasonic sound waves sufficient to ablate tissue when coupled to a suitable excitation source.

In addition, other elements for altering the nature of tissue may be suitable as "ablation elements" under the present invention when adapted according to the detailed description of the invention below. For example, a cryoablation element adapted to sufficiently cool tissue to substantially alter the structure thereof may be suitable if adapted according to the teachings of the current invention. Furthermore, a fluid delivery element, such as a discrete port or a plurality of ports which are fluidly coupled to a fluid delivery source, may be adapted to infuse an ablating fluid, such as a fluid containing alcohol, into the tissue adjacent to the port or ports to substantially alter the nature of that tissue.

The term "diagnose", including derivatives thereof, is intended to include patients suspected or predicted to have atrial arrhythmia, in addition to those having specific symptoms or mapped electrical conduction indicative of atrial arrhythmia.

Returning to the inventive method as shown in FIG. 1, a patient diagnosed with atrial arrhythmia according to diagnosing step (1) is treated with a circumferential conduction block according to treatment step (2). In one aspect, a patient diagnosed according to diagnosis step (1) with multiple wavelet arrhythmia originating from multiple regions along the atrial wall may also be treated in part by forming the circumferential conduction block according to treatment step (2), although as an adjunct to forming long linear regions of conduction block between adjacent pulmonary vein ostia in a less-invasive "maze"-type catheter ablation procedure. More detail regarding this particular aspect of the inventive method is provided below with reference to a combination circumferential-long linear lesion ablation device which is described below with reference to FIGS. 9A–F.

In another aspect of the method of FIG. 1, a patient diagnosed with focal arrhythmia originating from an arrhythmogenic origin or focus in a pulmonary vein is treated according to this method when the circumferential conduction block is formed along a circumferential path of wall tissue that either includes the arrhythmogenic origin or is between the origin and the left atrium. In the former case, the arrhythmogenic tissue at the origin is destroyed by the conduction block as it is formed through that focus. In the latter case, the arrhythmogenic focus may still conduct abnormally, although such aberrant conduction is prevented from entering and affecting the atrial wall tissue due to the intervening circumferential conduction block.

In still a further aspect of the method shown in FIG. 1, the circumferential conduction block may be formed in one of several ways according to treatment step (2). In one example not shown, the circumferential conduction block may be formed by a surgical incision or other method to mechanically transect the pulmonary vein, followed by suturing the transected vein back together. As the circumferential injury is naturally repaired, such as through a physiologic scarring response common to the "maze" procedure, electrical conduction will generally not be restored across the injury site. In another example not shown, a circumferential conduction block of one or more pulmonary veins may be performed in an epicardial ablation procedure, wherein an ablation element is either placed around the target pulmonary vein or is translated circumferentially around it while being energized to ablate the adjacent tissue in an "outside-in" approach. This alternative method may be performed during an open chest-type procedure, or may be done using other known epicardial access techniques.

Figure 3:
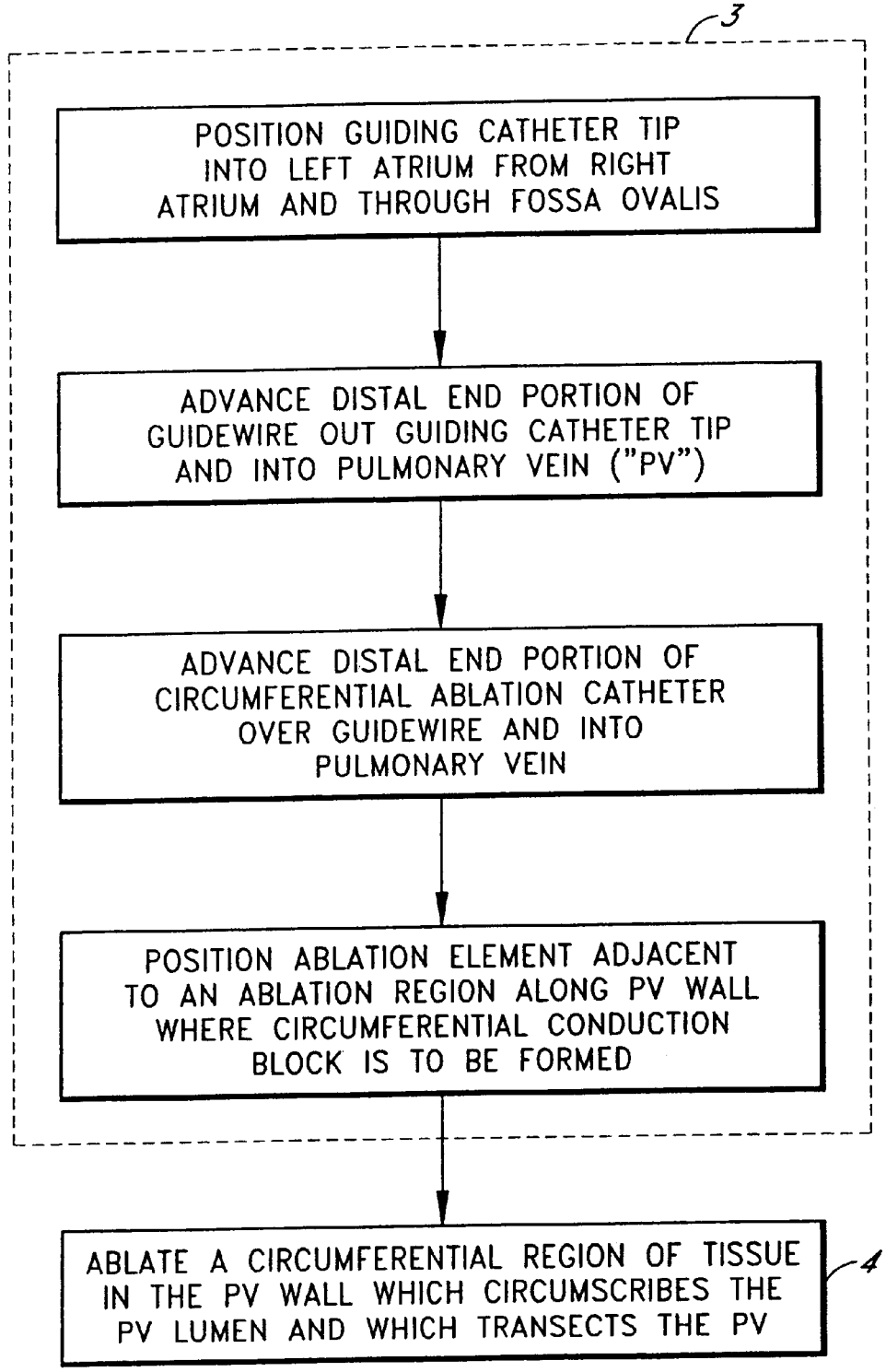
FIG. 3 shows a flow diagram of a method for using a circumferential ablation device assembly.

FIG. 3 diagrammatically shows the sequential steps of a method for using a circumferential ablation device assembly to form a circumferential conduction block in a pulmonary vein. The circumferential ablation method according to FIG. 3 includes: positioning a circumferential ablation element at an ablation region along the pulmonary vein according to a series of detailed steps shown collectively in FIG. 3 as positioning step (3); and thereafter ablating a continuous circumferential region of tissue in the PV wall at the ablation region according to ablation step (4).

Further to positioning step (3) according to the method of FIG. 3, a distal tip of a guiding catheter is first positioned within the left atrium according to a transeptal access method, which is further described in more detail as follows. The right venous system is first accessed using the "Seldinger" technique, wherein a peripheral vein (such as a femoral vein) is punctured with a needle, the puncture wound is dilated with a dilator to a size sufficient to accommodate an introducer sheath, and an introducer sheath with at least one hemostatic valve is seated within the dilated puncture wound while maintaining relative hemostasis. With the introducer sheath in place, the guiding catheter or sheath is introduced through the hemostatic valve of the introducer sheath and is advanced along the peripheral vein, into the region of the vena cavae, and into the right atrium.

Once in the right atrium, the distal tip of the guiding catheter is positioned against the fossa ovalis in the intraatrial septal wall. A "Brockenbrough" needle or trocar is then advanced distally through the guide catheter until it punctures the fossa ovalis. A separate dilator may also be advanced with the needle through the fossa ovalis to prepare an access port through the septum for seating the guiding catheter. The guiding catheter thereafter replaces the needle across the septum and is seated in the left atrium through the fossa ovalis, thereby providing access for object devices through its own inner lumen and into the left atrium.

It is however further contemplated that other left atrial access methods may be suitable substitutes for using a circumferential ablation device assembly for pulmonary vein isolation. In one alternative variation not shown, a "retrograde" approach may be used, wherein the guiding catheter is advanced into the left atrium from the arterial system. In this variation, the Seldinger technique is employed to gain vascular access into the arterial system, rather than the venous, for example, at a femoral artery. The guiding catheter is advanced retrogradedly through the aorta, around the aortic arch, into the ventricle, and then into the left atrium through the mitral valve.

Subsequent to gaining transeptal access to the left atrium as just described, positioning step (3) according to FIG. 3 next includes advancing a guidewire into a pulmonary vein, which is done generally through the guiding catheter seated in the fossa ovalis. In addition to the left atrial access guiding catheter, the guidewire according to this variation may also be advanced into the pulmonary vein by directing it into the vein with a second sub-selective delivery catheter (not shown) which is coaxial within the guiding catheter, such as, for example, by using one of the directional catheters disclosed in U.S. Pat. No. 5,575,766 to Swartz. Or, the guidewire may have sufficient stiffness and maneuverability in the left atrial cavity to unitarily subselect the desired pulmonary vein distally of the guiding catheter seated at the fossa ovalis.

Suitable guidewire designs for use in the overall circumferential ablation device assembly described may be selected from previously known designs, while generally any suitable choice should include a shaped, radiopaque distal end portion with a relatively stiff, torquable proximal portion adapted to steer the shaped tip under X-ray visualization. Guidewires having an outer diameter ranging from 0.010" to 0.035" may be suitable. In cases where the guidewire is used to bridge the atrium from the guiding catheter at the fossa ovalis, and where no other sub-selective guiding catheters are used, guidewires having an outer diameter ranging from 0.018" to 0.035" may be required. It is believed that guidewires within this size range may be required to provide sufficient stiffness and maneuverability in order to allow for guidewire control and to prevent undesirable guidewire prolapsing within the relatively open atrial cavity.

Subsequent to gaining pulmonary vein access, positioning step (3) of FIG. 3 next includes tracking the distal end portion of a circumferential ablation device assembly over the guidewire and into the pulmonary vein, followed by positioning a circumferential ablation element at an ablation region of the pulmonary vein where the circumferential conduction block is to be desirably formed.

Figure 4:
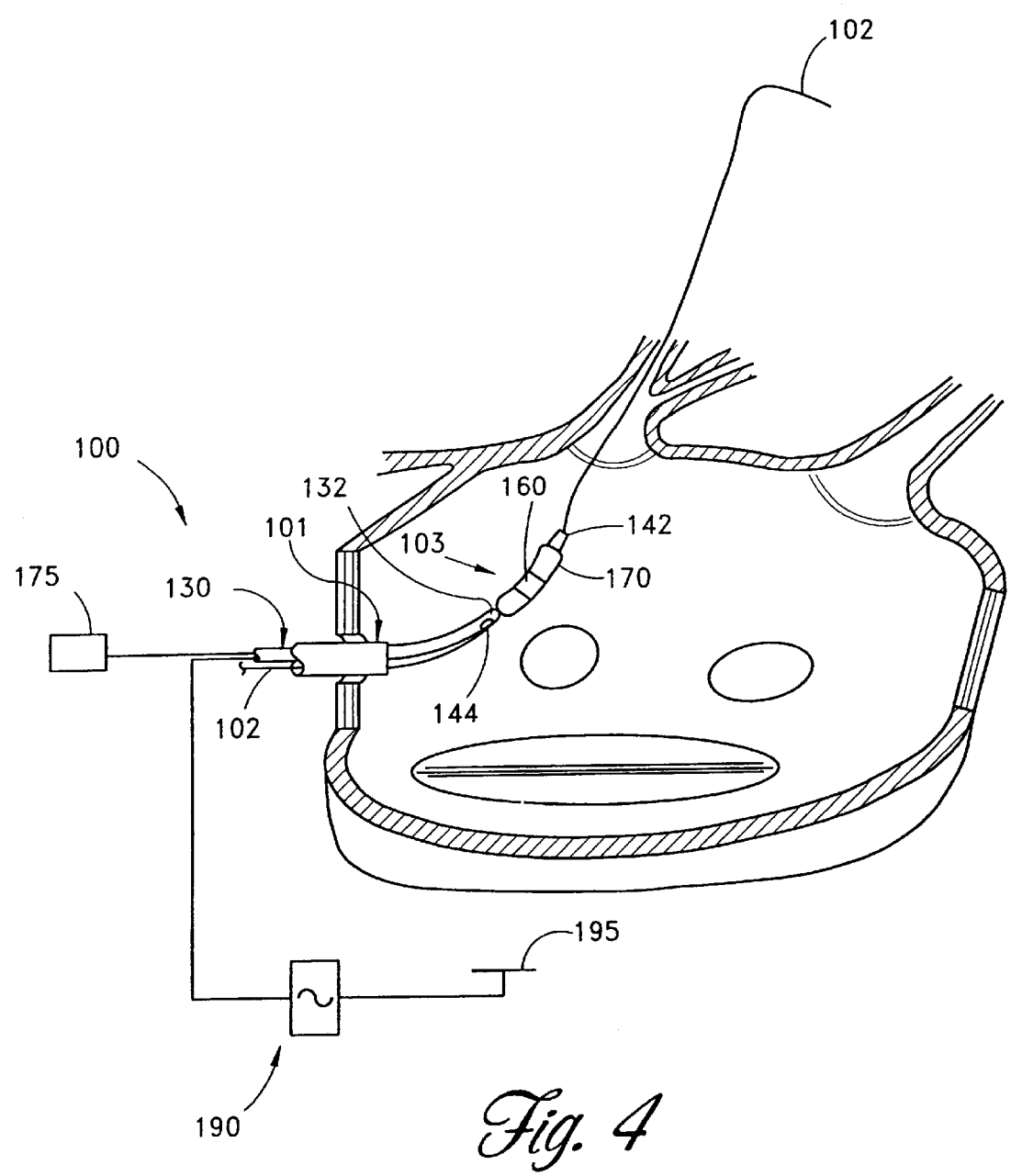
FIG. 4 shows a perspective view of a circumferential ablation device assembly during use in a left atrium subsequent to performing transeptal access and guidewire positioning steps according to the method of FIG. 3.
Figure 5:
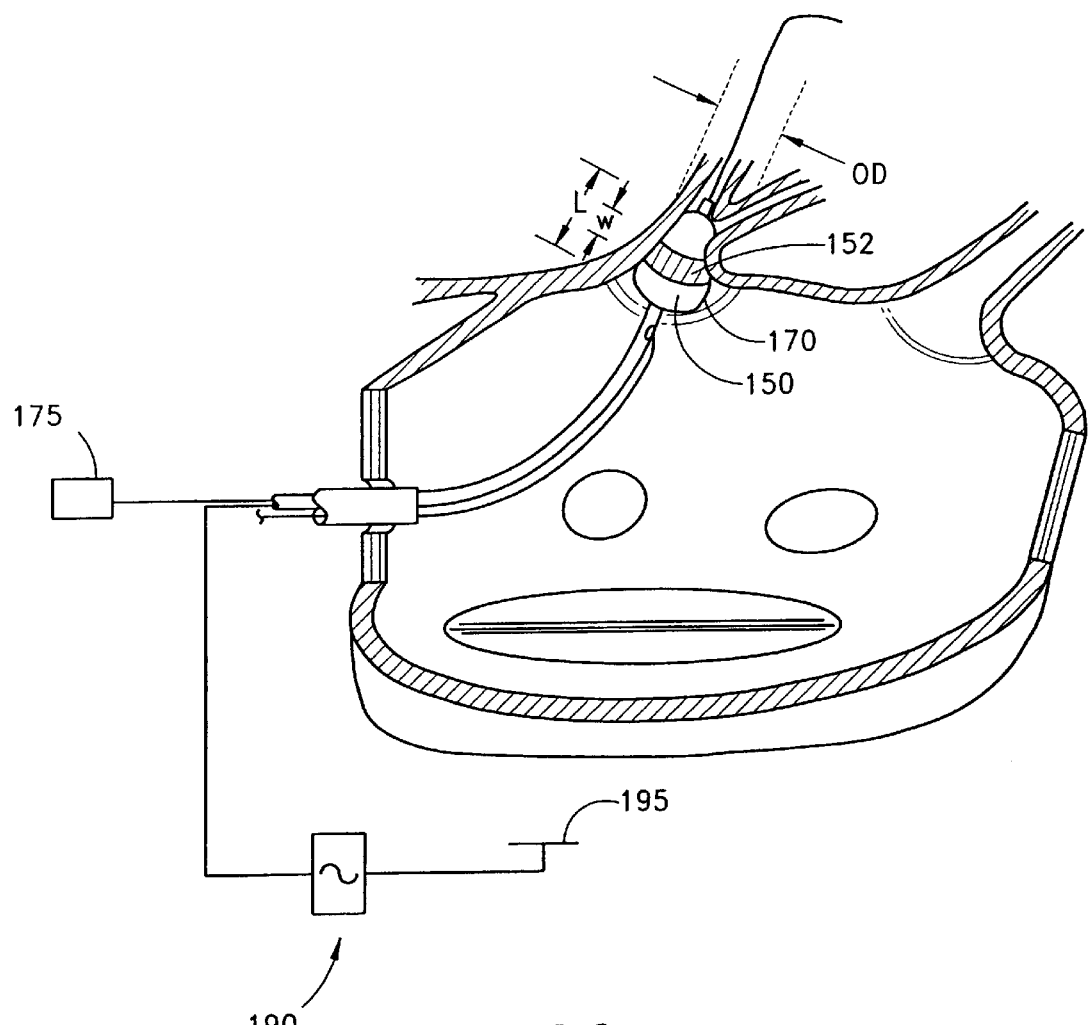
FIG. 5 shows a similar perspective view of the circumferential ablation device assembly shown in FIG. 4, and further shows a circumferential ablation catheter during use in ablating a circumferential region of tissue along a pulmonary vein wall to form a circumferential conduction block in the pulmonary vein according to the method of FIG. 3.

FIGS. 4–5 further show a circumferential ablation device assembly (100) during use in performing positioning step (3) and ablation step (4) just described with reference to FIG. 3. Included in the circumferential ablation device assembly (100) are guiding catheter (101), guidewire (102), and circumferential ablation catheter (103).

More specifically, FIG. 4 shows guiding catheter (101) subsequent to performing a transeptal access method according to FIG. 3, and also shows guidewire (102) subsequent to advancement and positioning within a pulmonary vein, also according to step (3) of FIG. 3. FIG. 4 shows circumferential ablation catheter (103) as it tracks coaxially over guidewire (102) with a distal guidewire tracking member, which is specifically shown only in part at first and second distal guidewire ports (142,144) located on the distal end portion (132) of an elongate catheter body (130). A guidewire lumen (not shown) extends between the first and second distal guidewire ports (142,144) and is adapted to slidably receive and track over the guidewire. In the particular variation of FIG. 4, the second distal guidewire port (142) is located on a distal end portion (132) of the elongate catheter body (130), although proximally of first distal guidewire port (142).

As would be apparent to one of ordinary skill, the distal guidewire tracking member shown in FIG. 4 and just described may be slidably coupled to the guidewire externally of the body in a "backloading" technique after the guidewire is first positioned in the pulmonary vein. Furthermore, there is no need in this guidewire tracking variation for a guidewire lumen in the proximal portions of the elongate catheter body (130), which allows for a reduction in the outer diameter of the catheter shaft in that region. Nevertheless, it is further contemplated that a design which places the second distal guidewire port on the proximal end portion of the elongate catheter body would also be acceptable, as is described below, for example, with reference to the perfusion embodiment of FIGS. 6A–B.

In addition, the inclusion of a guidewire lumen extending within the elongate body between first and second ports, as provided in FIG. 4, should not limit the scope of acceptable guidewire tracking members. Other guidewire tracking members which form a bore adapted to slidably receive and track over a guidewire are also considered acceptable, such as, for example, the structure adapted to engage a guidewire as described in U.S. Pat. No. 5,505,702 to Arney.

While the assemblies and methods shown variously throughout the Figures include a guidewire coupled to a guidewire tracking member on the circumferential ablation catheter, other detailed variations may also be suitable for positioning the circumferential ablation element at the ablation region in order to form a circumferential conduction block there. For example, an alternative circumferential ablation catheter not shown may include a "fixedwire"-type of design wherein a guidewire is integrated into the ablation catheter as one unit. In another alternative assembly, the same type of sub-selective sheaths described above with reference to U.S. Pat. No. 5,575,766 to Swartz for advancing a guidewire into a pulmonary vein may also be used for advancing a circumferential ablation catheter device across the atrium and into a pulmonary vein.

FIG. 4 also shows circumferential ablation catheter (103) with a circumferential ablation element (160) formed on an expandable member (170). The expandable member (170) is shown in FIG. 4 in a radially collapsed position adapted for percutaneous translumenal delivery into the pulmonary vein according to positioning step (3) of FIG. 3. However, expandable member (170) is also adjustable to a radially expanded position when actuated by an expansion actuator (175), as shown in FIG. 5. Expansion actuator (175) may include, but is not limited to, a pressurizeable fluid source. According to the expanded state shown in FIG. 5, expandable member (170) includes a working length L relative to the longitudinal axis of the elongate catheter body which has a larger expanded outer diameter OD than when in the radially collapsed position. Furthermore, the expanded outer diameter OD is sufficient to circumferentially engage the ablation region of the pulmonary vein. Therefore, the terms "working length" are herein intended to mean the length of an expandable member which, when in a radially expanded position, has an expanded outer diameter that is: (a) greater than the outer diameter of the expandable member when in a radially collapsed position; and (b) sufficient to engage a body space wall or adjacent ablation region surrounding the expandable member, at least on two opposing internal sides of the body space wall or adjacent ablation region, with sufficient surface area to anchor the expandable member.

Circumferential ablation element (160) also includes a circumferential band (152) on the outer surface of working length L which is coupled to an ablation actuator (190) at a proximal end portion of the elongate catheter body (shown schematically). After expandable member (170) is adjusted to the radially expanded position and at least a portion of working length L circumferentially engages the pulmonary vein wall in the ablation region, the circumferential band (152) of the circumferential ablation element (160) is actuated by ablation actuator (190) to ablate the surrounding circumferential path of tissue in the pulmonary vein wall, thereby forming a circumferential lesion that circumscribes the pulmonary vein lumen and transects the electrical conductivity of the pulmonary vein to block conduction in a direction along its longitudinal axis.

FIG. 6A shows another circumferential ablation catheter (203) during use also according to the method of FIG. 3, wherein a perfusion lumen (260) (shown in phantom in FIG. 6B) is formed within the distal end portion (232) of elongate catheter body (230). The perfusion lumen (260) in this example is formed between a distal perfusion port, which in this example is the first distal guidewire port (242), and proximal perfusion port (244). Proximal perfusion port (244) is formed through the wall of the elongate catheter body (230) and communicates with the guidewire lumen (not shown) which also forms the perfusion lumen between the distal and proximal perfusion ports. In the particular design shown, after the guidewire has provided for the placement of the ablation element into the pulmonary vein, the guidewire is withdrawn proximally of the proximal perfusion port (244) (shown schematically in shadow) so that the lumen between the ports is clear for antegrade blood flow into the distal perfusion port (242), proximally along the perfusion lumen, out the proximal perfusion port (244) and into the atrium (perfusion flow shown schematically with arrows).

Further to the perfusion design shown in FIGS. 6A–B, guidewire (102) is positioned in a guidewire lumen which extends the entire length of the elongate catheter body (230) in an "over-the-wire"-type of design, which facilitates the proximal withdrawal of the guidewire to allow for perfusion while maintaining the ability to subsequently re-advance the guidewire distally through the first distal guidewire port (242) for catheter repositioning. In one alternative variation not shown, the guidewire is simply withdrawn and disengaged from the second distal guidewire port (244), in which case the circumferential ablation catheter must generally be withdrawn from the body in order to re-couple the distal guidewire tracking member with the guidewire.

In another alternative perfusion variation not shown which is a modification of the embodiment of FIG. 6A, a proximal perfusion port is provided as a separate and distinct port positioned between the second distal guidewire port (244) and the expandable member (270), which allows for proximal withdrawal of the guidewire to clear the guidewire lumen and thereby form a perfusion lumen between the first distal guidewire port and the proximal perfusion port. The guidewire of this alternative variation, however, remains engaged within the guidewire lumen between the second distal guidewire port and the proximal perfusion port.

Passive perfusion during expansion of the expandable member is believed to minimize stasis and allow the target pulmonary vein to continue in its atrial filling function during the atrial arrhythmia treatment procedure. Without this perfusion feature, the expandable member when in the radially expanded position during ablation blocks the flow from the vein into the atrium, which flow stasis may result in undesirable thrombogenesis in the pulmonary vein distally to the expandable member. In addition, in cases where the ablation element is adapted to ablate tissue with heat conduction at the ablation region, as described by reference to more detailed embodiments below, the perfusion feature according to the variation of FIGS. 6A–B may also provide a cooling function in the surrounding region, including in the blood adjacent to the expandable member.

Moreover, in addition to the specific perfusion structure shown and described by reference to FIGS. 6A–B, it is to be further understood that other structural variants which allow for perfusion flow during expansion of the expandable element may provide suitable substitutes according to one of ordinary skill.

Figure 7:
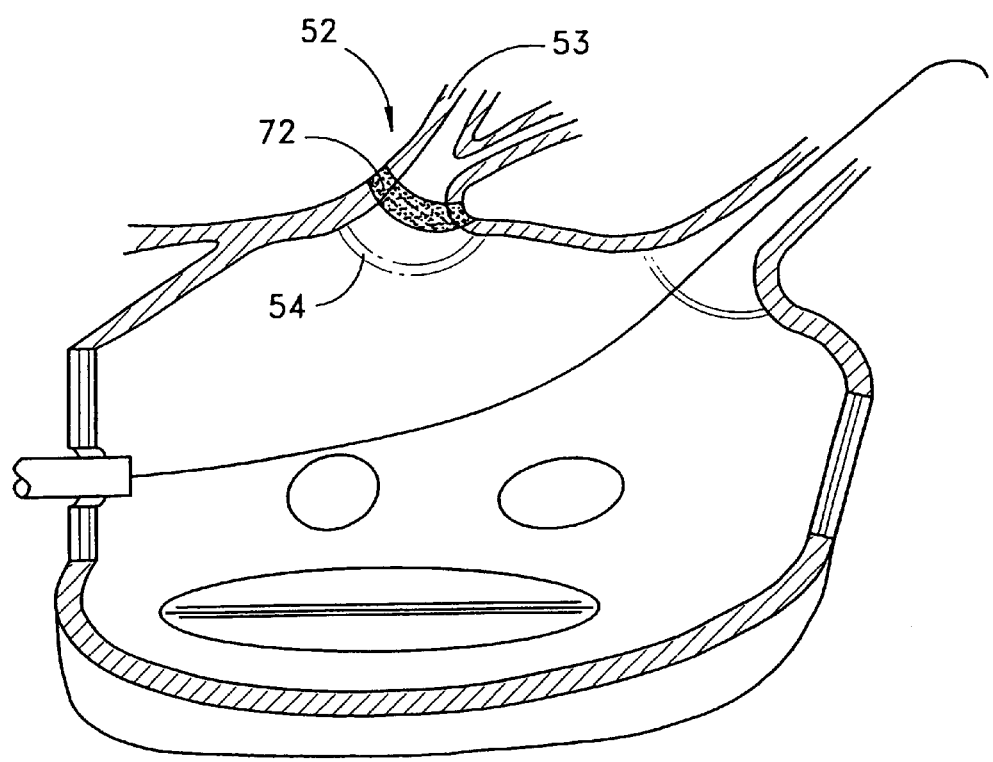
FIG. 7 shows a similar perspective view of the left atrium as that shown in FIGS. 3–5, although showing a cross-sectional view of a circumferential lesion after being formed by circumferential catheter ablation according to the method of FIG. 3.

FIG. 7 shows pulmonary vein (52) after removing the circumferential ablation device assembly subsequent to forming a circumferential lesion (70) around the ablation region of the pulmonary vein wall (53) according to the use of the circumferential ablation device assembly shown in stepwise fashion in FIGS. 3–6. Circumferential lesion (70) is shown located along the pulmonary vein adjacent to the pulmonary vein ostium (54), and is shown to also be "transmural," which is herein intended to mean extending completely through the wall, from one side to the other. Also, the circumferential lesion (70) is shown in FIG. 7 to form a "continuous" circumferential band, which is herein intended to mean without gaps around the pulmonary vein wall circumference, thereby circumscribing the pulmonary vein lumen.

It is believed, however, that circumferential catheter ablation with a circumferential ablation element according to various uses of the ultrasound ablation element structures of the present invention may leave some tissue, either transmurally or along the circumference of the lesion, which is not actually ablated, but which is not substantial enough to allow for the passage of conductive signals. Therefore, the terms "transmural" and "continuous" as just defined are intended to have functional limitations, wherein some tissue in the ablation region may be unabated but there are no functional gaps which allow for symptomatically arrhythmogenic signals to conduct through the conduction block and into the atrium from the pulmonary vein.

Moreover, it is believed that the functionally transmural and continuous lesion qualities just described are characteristic of a completed circumferential conduction block in the pulmonary vein. Such a circumferential conduction block thereby transects the vein, isolating conduction between the portion of the vein on one longitudinal side of the lesion and the portion on the other side. Therefore, any foci of originating arrhythmogenic conduction which is opposite the conduction block from the atrium is prevented by the conduction block from conducting down into the atrium and atrial arrhythmic affects are therefore nullified.

Figure 8A:
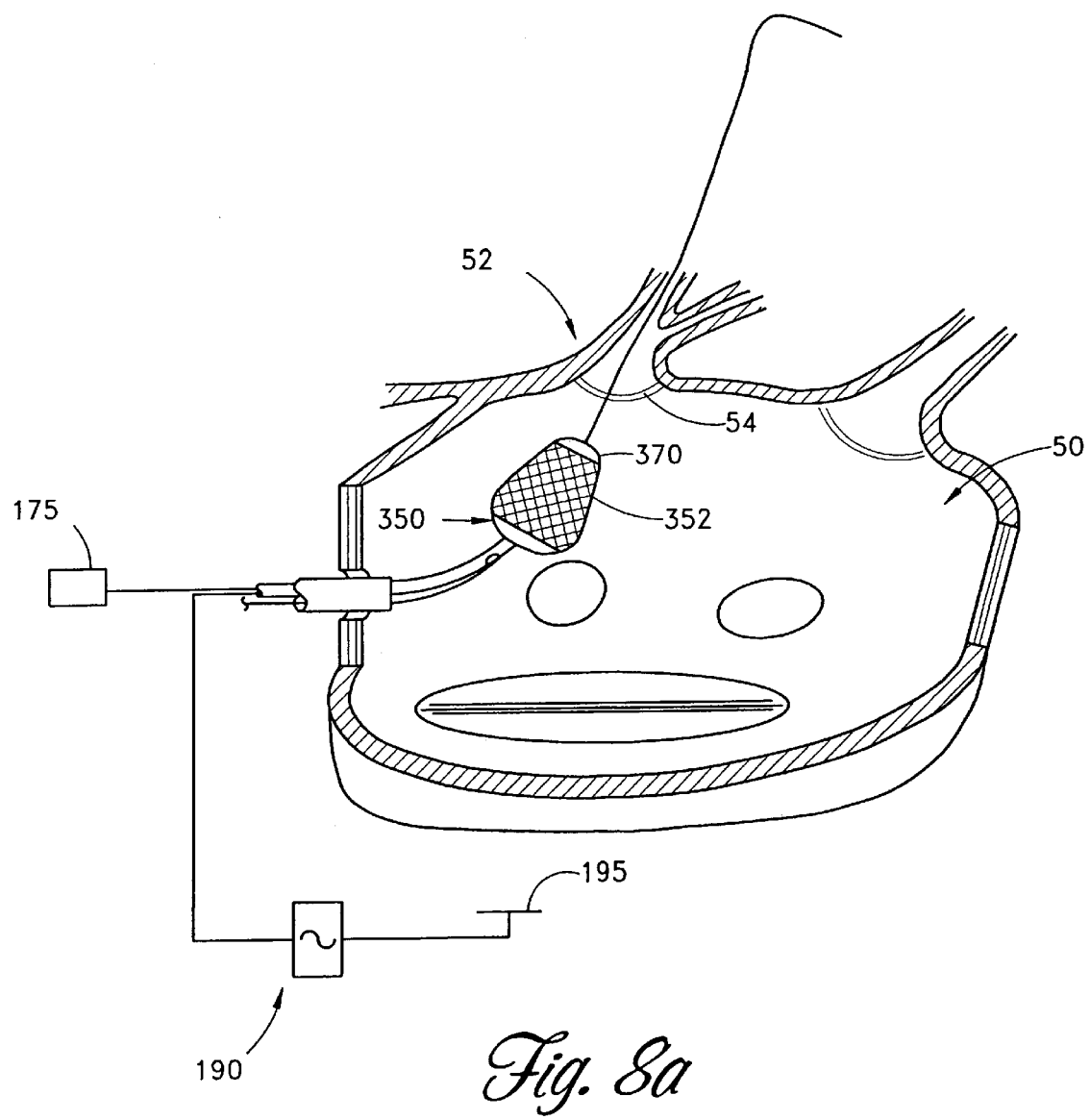
Figure 8B:
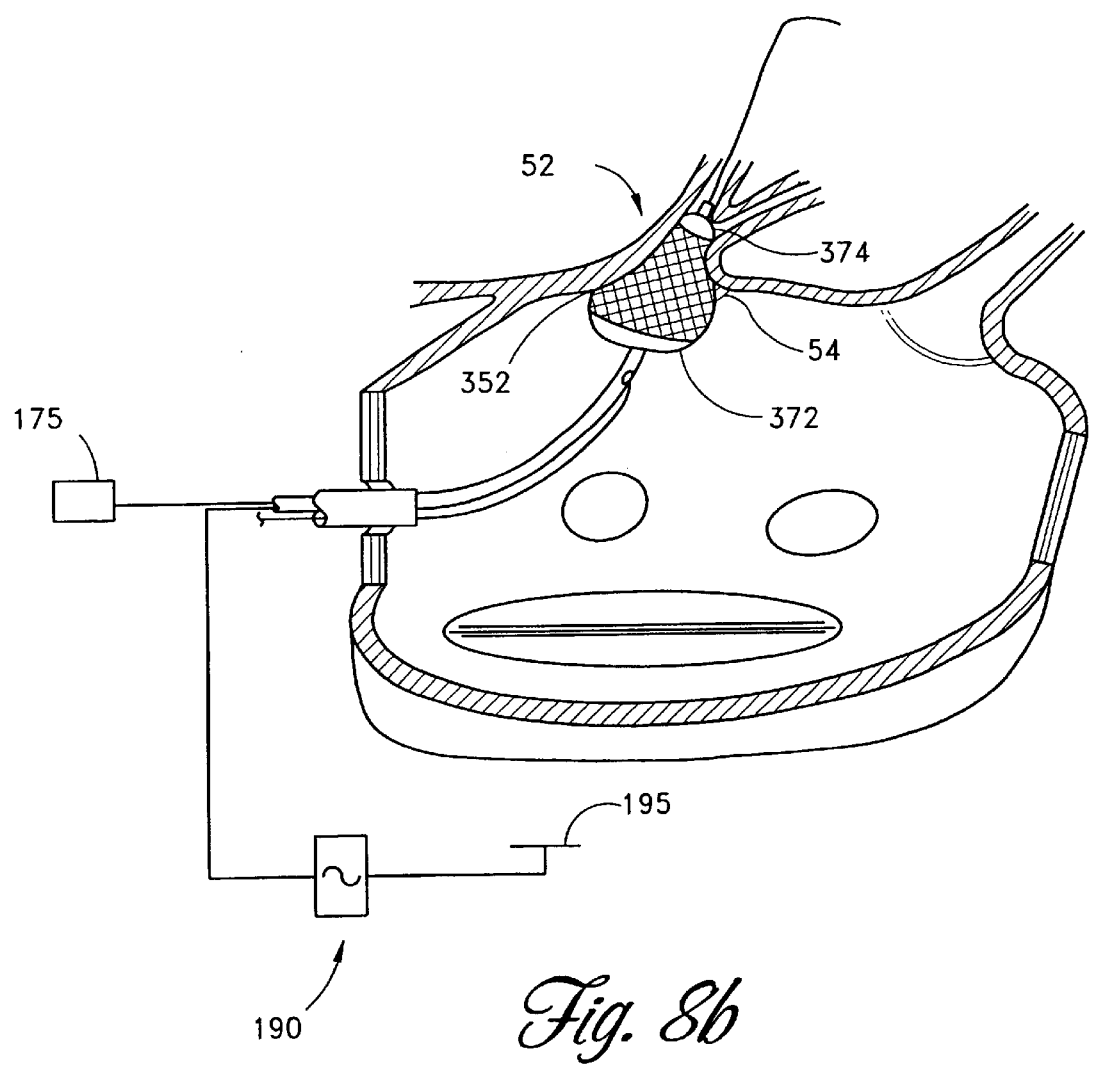
Figure 8C:
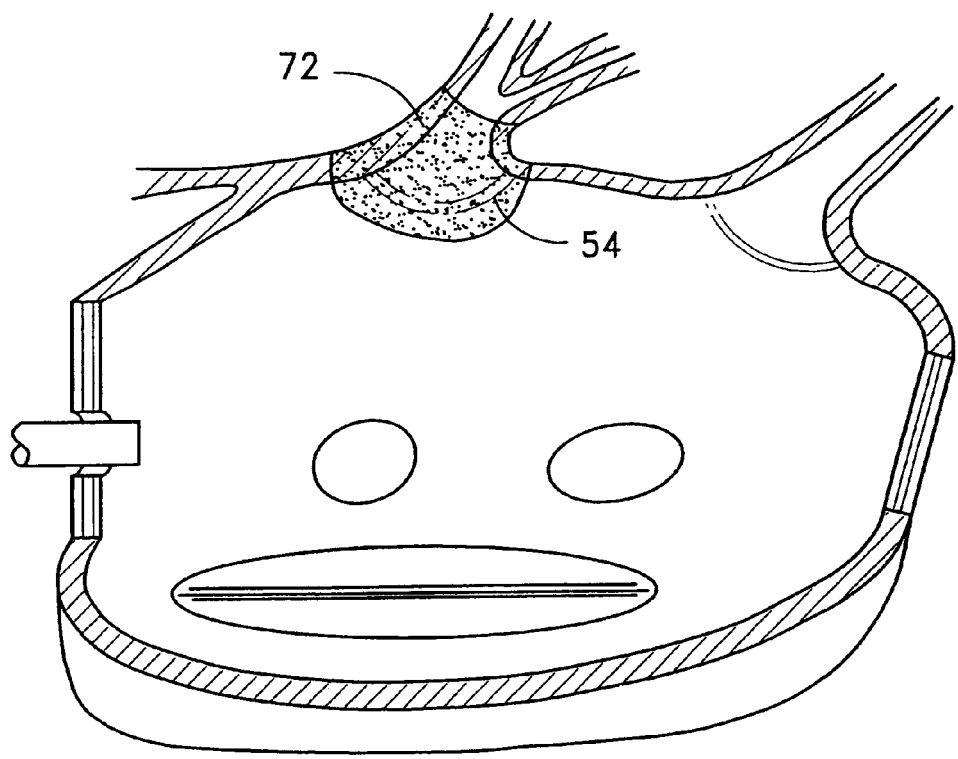
FIG. 8C shows the same perspective view of the left atrium shown in FIGS. 8A–B, although shown after forming a circumferential conduction block according to the circumferential ablation procedure of FIG. 3 and also after removing the circumferential ablation device assembly from the left atrium.

FIGS. 8A–B show a further circumferential ablation member (350) that includes a radially compliant expandable member (370) which is adapted to conform to a pulmonary vein ostium (54) at least in part by adjusting it to a radially expanded position while in the left atrium and then advancing it into the ostium. FIG. 8A shows expandable member (370) after being adjusted to a radially expanded position while located in the left atrium (50). FIG. 8B further shows expandable member (370) after being advanced into the pulmonary vein (52) until at least a portion of the expanded working length L of circumferential ablation member (350), which includes a circumferential band (352), engages the pulmonary vein ostium (54). FIG. 8C shows a portion of a circumferential lesion (72) which forms a circumferential conduction block in the region of the pulmonary vein ostium (54) subsequent to actuating the circumferential ablation element to form the circumferential lesion.

In addition to conforming to the pulmonary vein ostium, expandable member (370) is also shown in FIG. 8B to engage a circumferential path of tissue along the left posterior atrial wall which surrounds ostium (54). Moreover, circumferential bank (352) of the circumferential ablation member is also thereby adapted to engage that atrial wall tissue. Therefore, the circumferential conduction block formed according to the method shown and just described in sequential steps by reference to FIGS. 8A–B, as shown in-part in FIG. 8C, includes ablating the circumferential path of atrial wall tissue which surrounds ostium (54). Accordingly, the entire pulmonary vein, including the ostium, is thereby electrically isolated from at least a substantial portion of the left atrial wall which includes the other of the pulmonary vein ostia, as would be apparent to one of ordinary skill according to the sequential method steps shown in FIGS. 8A–B and by further reference to the resulting circumferential lesion (72) shown in FIG. 8C.

Figure 8E:
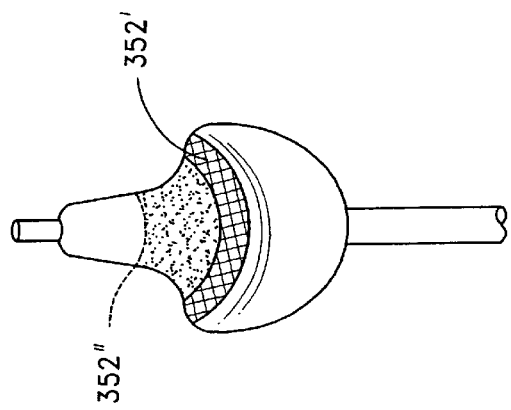
FIG. 8E shows one particular expandable member and circumferential ablation element which is adapted for use according to the mode of use shown in FIG. 8D.
Figure 8D:
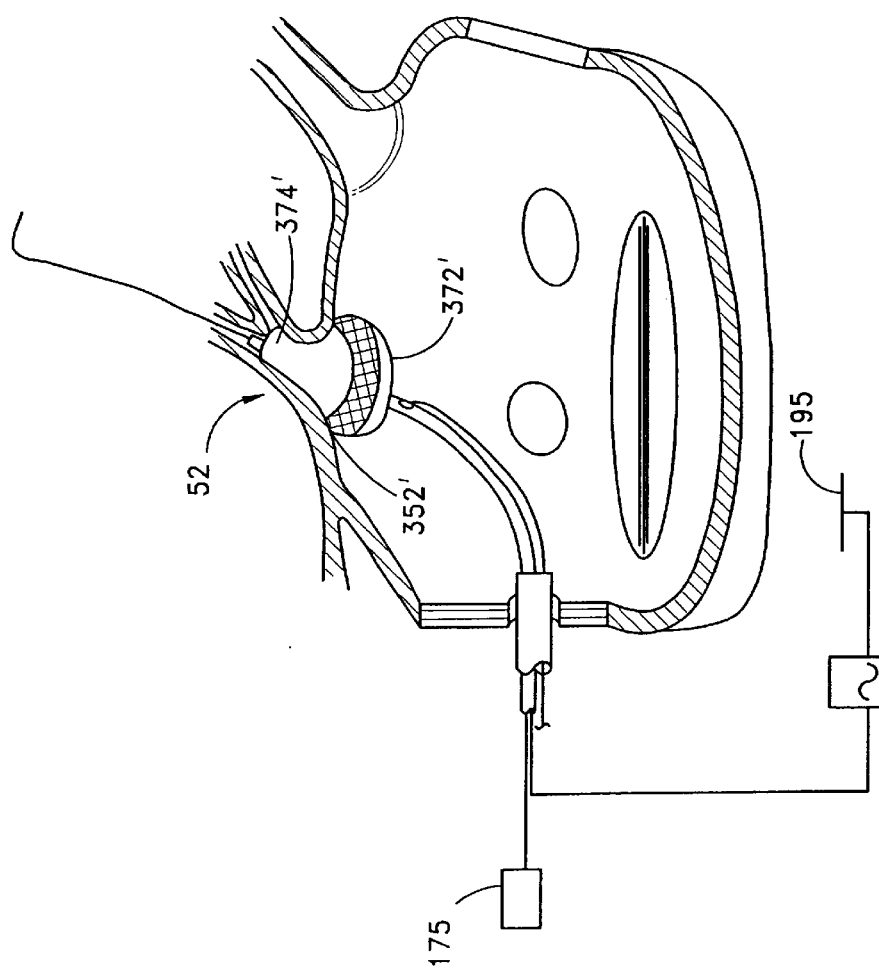
FIG. 8D shows another circumferential ablation catheter during use in a left atrium, and shows an expandable member in a radially expanded position which is engaged within a pulmonary vein ostium such that a circumferential band of a circumferential ablation element circumscribing the expandable member is also engaged to a circumferential path of tissue along the left posterior atrial wall which surrounds the pulmonary vein ostium.

FIGS. 8D–E show another highly beneficial circumferential ablation device embodiment and use thereof for electrically isolating pulmonary vein and ostium from a substantial portion of the left posterior atrial wall. However, unlike the embodiment previously shown and described by reference to FIGS. 8A–C, the FIGS. 8D–E embodiment isolates the pulmonary vein without also ablating tissue along the lumen or lining of the pulmonary vein or ostium, as is apparent by reference to the resulting circumferential conduction block shown in FIG. 8F.

In more detail, FIG. 8D shows a similar device assembly as that shown in FIGS. 8A–B, except that circumferential band (352') has a geometry (primarily width) and position along expandable member (370') such that it is adapted to engage only a circumferential path of tissue along the left posterior atrial wall which surrounds the pulmonary vein ostium. In one aspect of this embodiment, the compliant nature of the expandable member may be self-conforming to the region of the ostium such that the circumferential band is placed against this atrial wall tissue merely by way of conformability.

In another variation, a "pear"-shaped expandable member or balloon that includes a contoured taper may be suitable for use according to the FIG. 8D embodiment, as is shown by way of example in FIG. 8E. Such a pear shape may be preformed into the expandable member or balloon, or the member may be adapted to form this shape by way of controlled compliance as it expands, such as for example by the use of composite structures within the balloon construction. In any case, according to the "pear"-shaped variation, the circumferential band (352') of the ablation member is preferably placed along the surface of the contoured taper which is adapted to face the left posterior atrial wall during use according to the method illustrated by FIG. 8D. It is further contemplated that the ablation element may be further extended or alternatively positioned along other portions of the taper, such as is shown by example in shadow at extended band (352") in FIG. 8E. Accordingly, the variation shown in FIG. 8E to include extended band (352") may also adapt this particular device embodiment for use in forming circumferential conduction blocks also along tissue within the pulmonary vein and ostium, such as according to the previously described method shown in FIGS. 8A–C.

Figure 8F:
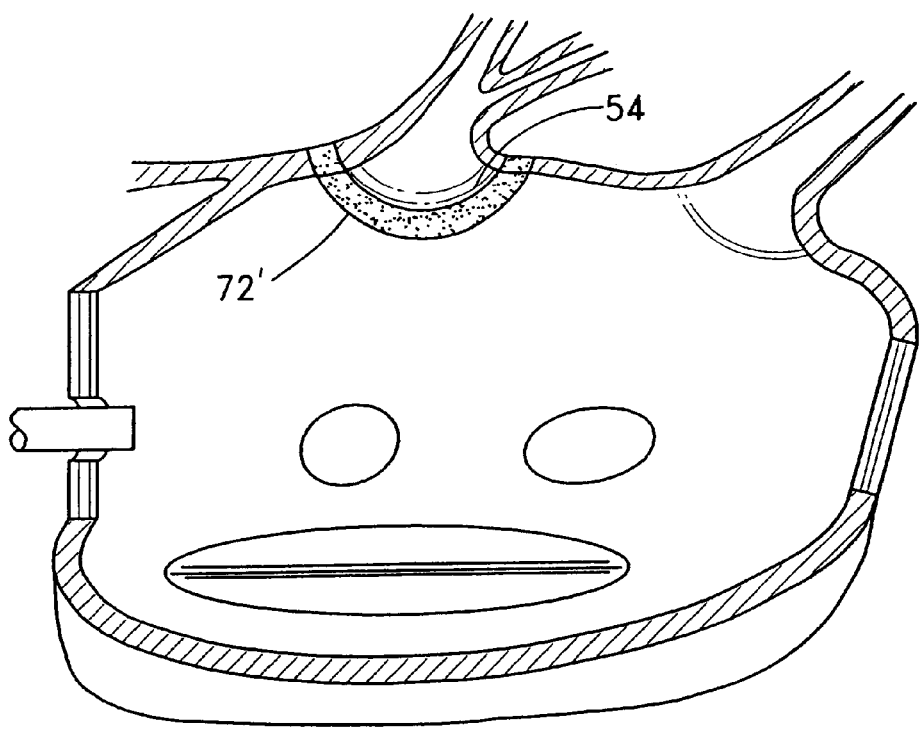
FIG. 8F shows a resulting circumferential conduction block or lesion which may be formed with the assemblies shown in FIGS. 8D–E and according to the method of use shown in FIG. 8D.

The method of forming a circumferential conduction block along a circumferential path of tissue along a left posterior atrial wall and which surrounds a pulmonary vein ostium without ablating the tissue of the vein or ostium should not be limited to the particular device embodiments just illustrated by reference to FIGS. 8D–F. Other device variations may be acceptable substitute for use according to this method. In one particular example which is believed to be suitable, a "looped" ablation member such as the embodiment illustrated below by reference to FIG. 15 may be adapted to form a "looped" ablation element within the left atrium and then be advanced against the left posterior atrial wall such that the loop engages the circumferential path of tissue along the atrial wall and which surrounds a vein ostium. Thereafter, the looped ablation element may be actuated to ablate the engaged tissue, such as for further illustration like a branding iron forming the predetermined pattern around the pulmonary vein os. In addition, other device or method variations may also be suitable substitutes according to one of ordinary skill.

FIGS. 9A–D collectively show a circumferential ablation device assembly as it is used to form a circumferential conduction block adjunctively to the formation of long linear lesions in a less-invasive "maze"-type procedure, as introduced above for the treatment of multiwavelet reentrant type fibrillation along the left atrial wall.

Figure 9A:
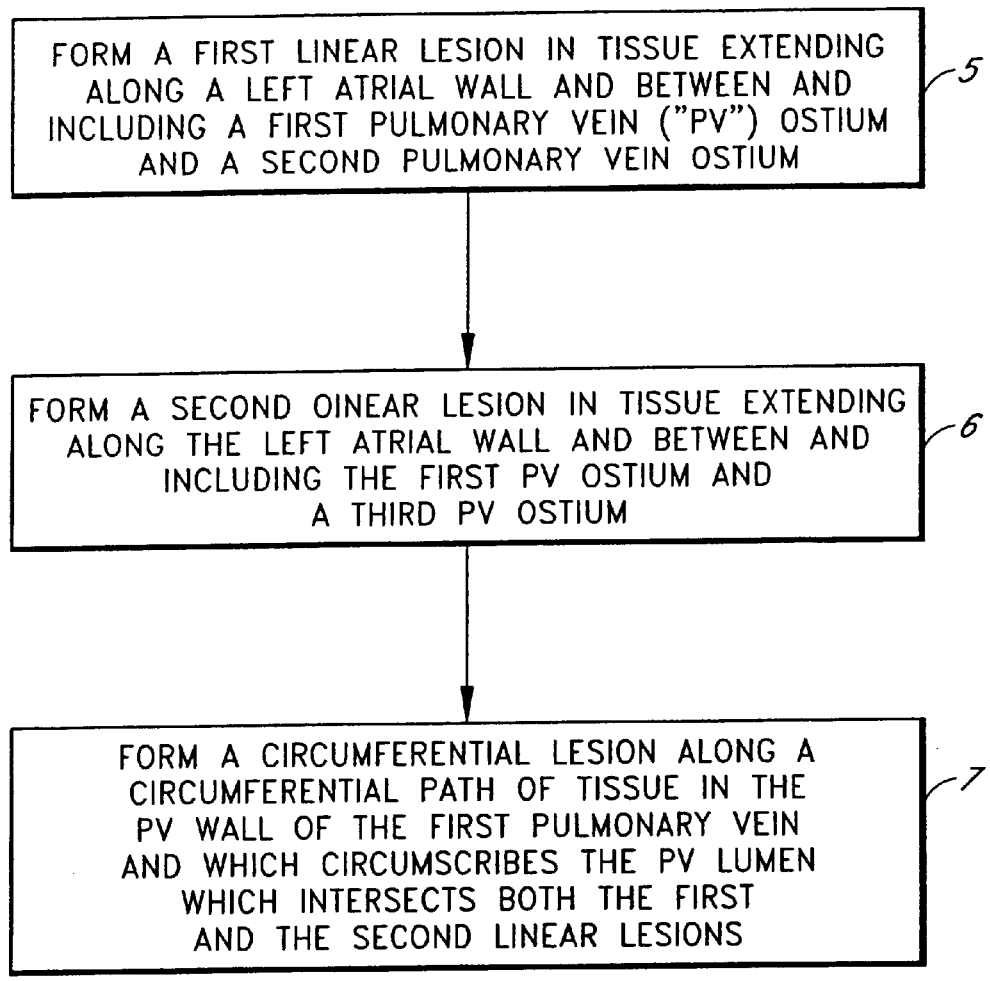
FIG. 9A diagrammatically shows a method for using a circumferential ablation device assembly to form a circumferential conduction block in a pulmonary vein in combination with a method for forming long linear lesions between pulmonary vein ostia in a less-invasive "maze"-type procedure.

More specifically, FIG. 9A diagrammatically shows a summary of steps for performing a "maze"-type procedure by forming circumferential conduction blocks that intersect with long linear conduction blocks formed between the pulmonary veins. As disclosed in copending patent application (Application Number not yet assigned) entitled "Tissue Ablation Device and Method of Use" filed by Michael Lesh, M.D. on May 9, 1997, which is herein incorporated in its entirety by reference thereto, a box-like conduction block surrounding an arrhythmogenic atrial wall region bounded by the pulmonary veins may be created by forming long linear lesions between anchors in all pairs of adjacent pulmonary vein ostia, such as is shown in part in steps (5) and (6) of FIG. 9A. However, it is further believed that, in some particular applications, such linear lesions may be made sufficiently narrow with respect to the surface area of the pulmonary vein ostia that they may not intersect, thereby leaving gaps between them which may present proarrhythmic pathways for abnormal conduction into and from the box, such as is shown between linear lesions (57,58) in FIG. 9B. Therefore, by forming the circumferential conduction block according to step (7) of FIG. 9A, and as shown by use of circumferential ablation member (450) in FIG. 9C, the linear lesions are thereby bridged and the gaps are closed.

Figure 9B:
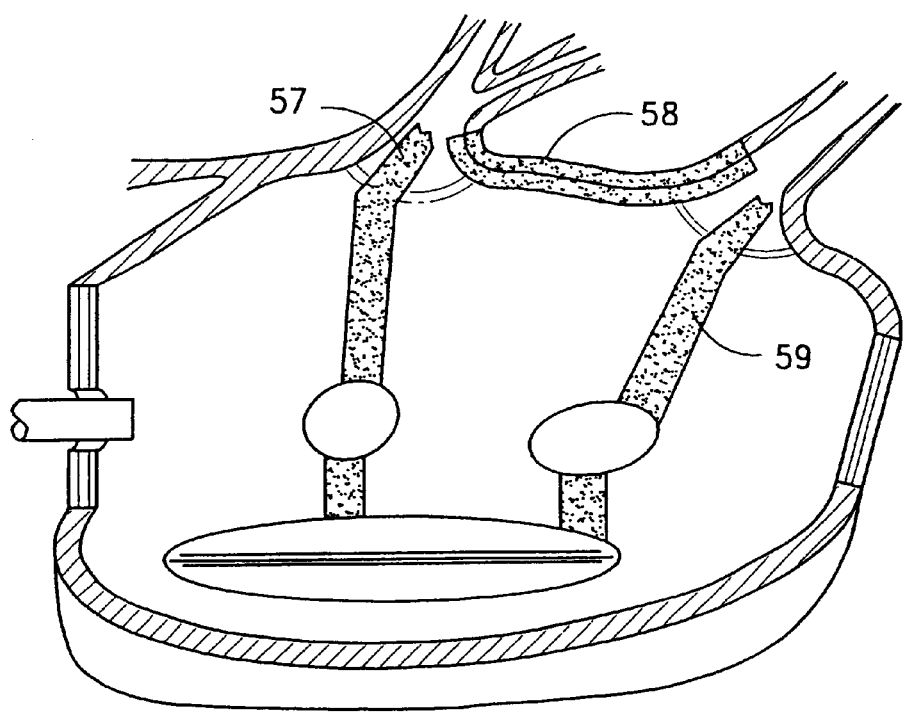
FIG. 9B shows a perspective view of a segmented left atrium after forming several long linear lesions between adjacent pairs of pulmonary vein ostia according to the method of FIG. 9A.
Figure 9C:
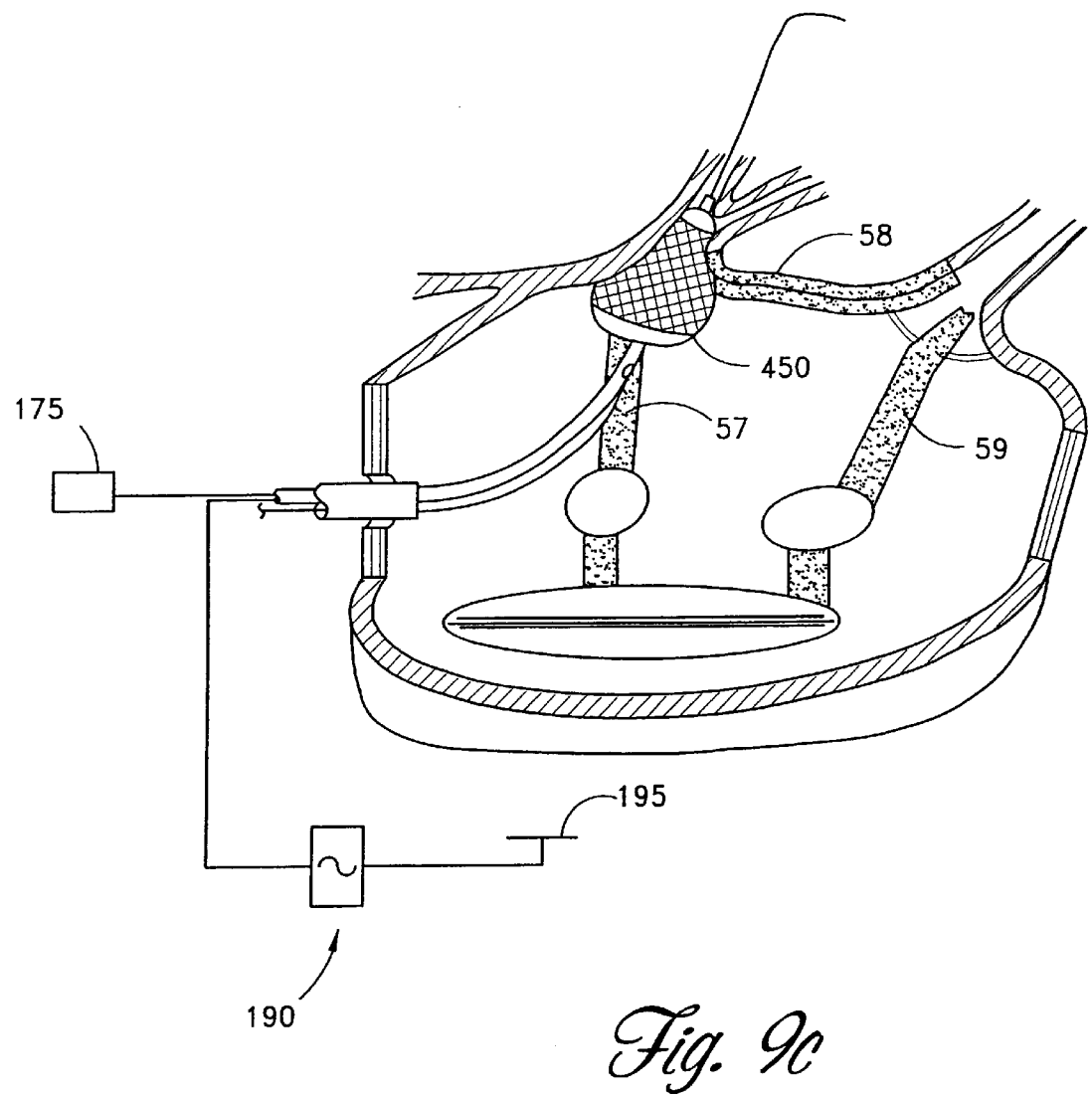
FIG. 9C shows a similar perspective view as that shown in FIG. 9B, although showing a circumferential ablation device assembly during use in forming a circumferential lesion in a pulmonary vein which intersects with two linear lesions that extend into the pulmonary vein, according to the method of FIG. 9A.
Figure 9D:
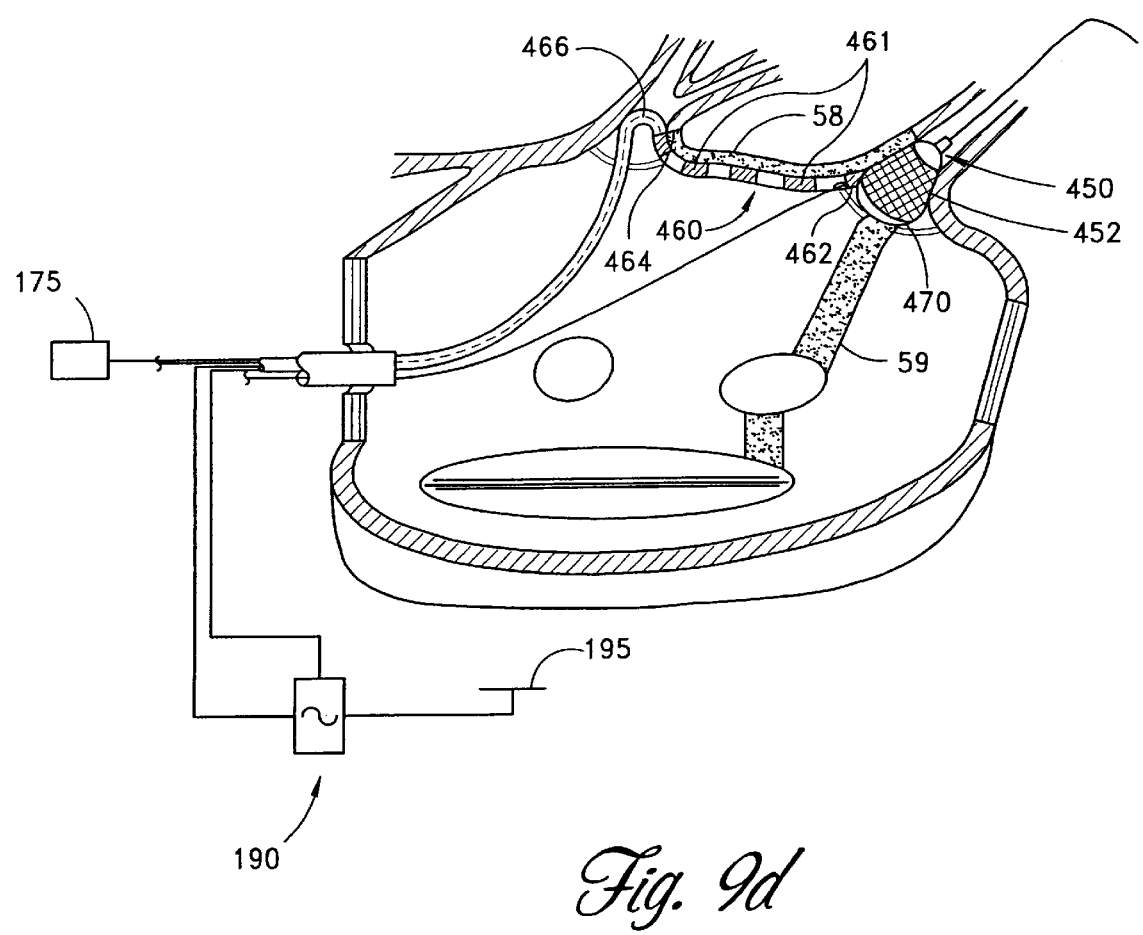
FIG. 9D shows a perspective view of another ablation catheter which combines a linear ablation member extending between two anchors with a circumferential ablation member for use in forming a circumferential lesion which intersects with at least one linear lesion according to the method of FIG. 9A.

In a further variation to the specific embodiments shown in FIGS. 9B–C, FIG. 9D shows another circumferential ablation device assembly which includes both circumferential and linear ablation elements (452,461), respectively. Circumferential ablation member (450) is shown to include an expandable member (470) which is adjusted to a radially expanded position that is asymmetric to the underlying catheter shaft. Linear ablation member (460) extends along the elongate body proximally from the circumferential ablation member (450). When expanded sufficiently to engage the pulmonary vein wall, expandable member (470) provides at least a portion of an anchor for a first end (462) of linear ablation member (460).

Figure 9E:
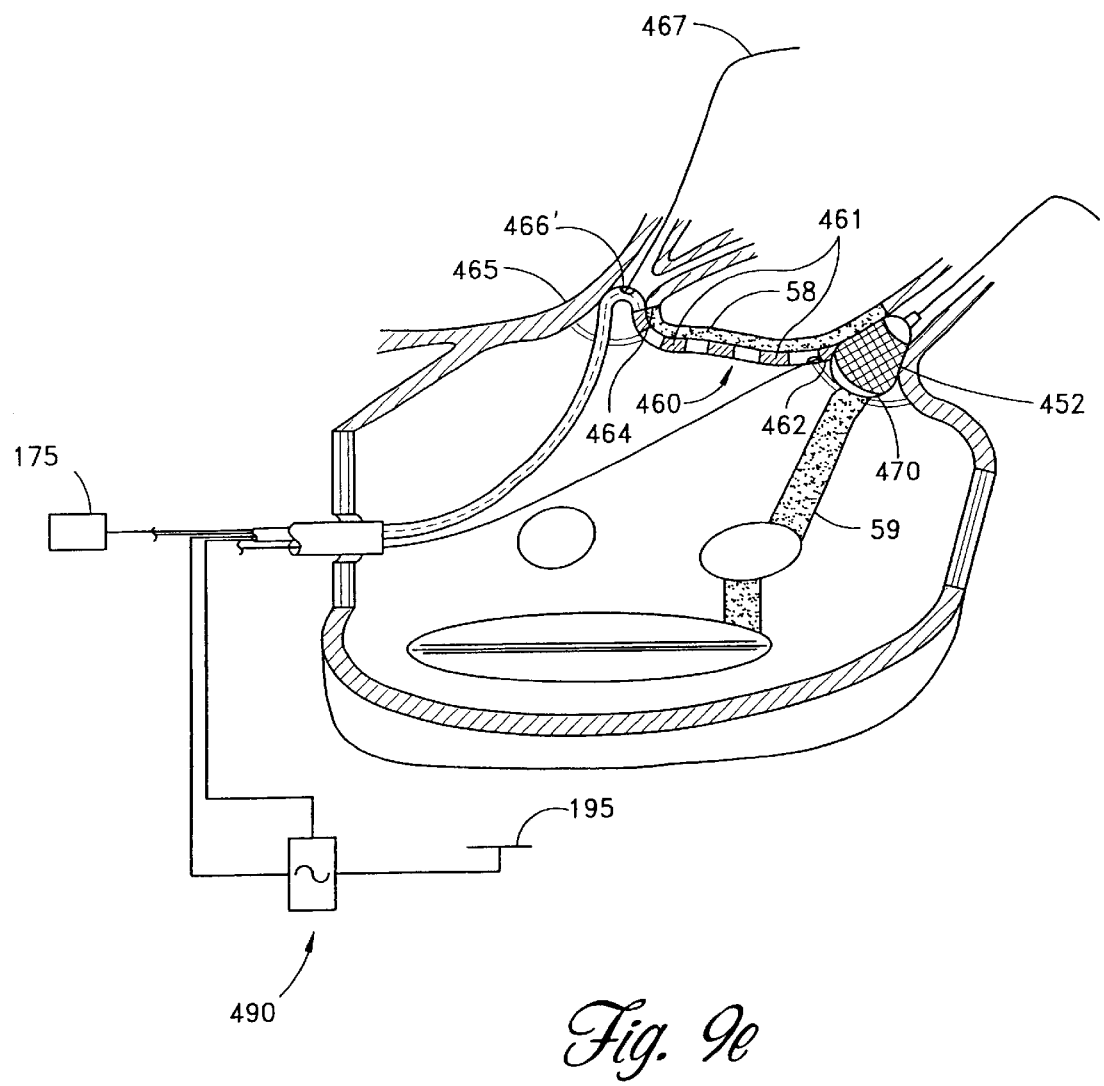
FIG. 9E shows a perspective view of another circumferential ablation catheter for use in forming a circumferential lesion that intersects with at least one linear lesion according to the method of FIG. 9A.

A shaped stylet (466) is shown in shadow in FIG. 9D within the elongate catheter body in the region of the second end (464) of the linear ablation member (460). Shaped stylet (466) is adapted to push the second end (464) into an adjacent pulmonary vein ostium such that the linear ablation member (460) is adapted to substantially contact the left atrial wall between the adjacent vein ostia to form the linear ablation according to the method of FIG. 9A. In addition to the use of shaped stylet (466), it is further contemplated that a second anchor may be used adjacent to second end (464), such as for example an intermediate guidewire tracking member adapted to track over a guidewire engaged to the pulmonary vein, as shown in FIG. 9E at intermediate guidewire tracking member (466') which is engaged over guidewire (469).

Moreover, the method shown schematically in FIG. 9A and also in various detail by reference to FIGS. 9B–C provides a specific sequence of steps for the purpose of illustration. According to this illustrative sequence, the linear lesions are formed first and then are connected thereafter with the circumferential conduction block. However, a circumferential conduction block may be formed prior to the formation of the linear lesions or conduction blocks, or in any other combination or sub-combination of sequential steps, so long as the resulting combination of lesions allows for the circumferential block to intersect with and connect with the linear lesions. In addition, the circumferential conduction block which connects the linear lesions may also include a circumferential path of tissue which surrounds and electrically isolates the pulmonary vein ostium from the rest of the left posterior atrial wall, such as for example by considering the embodiments just shown and described by reference to FIGS. 9A–E in view of the embodiment previously shown and described in relation to FIG. 8C above.

Figure 9F:
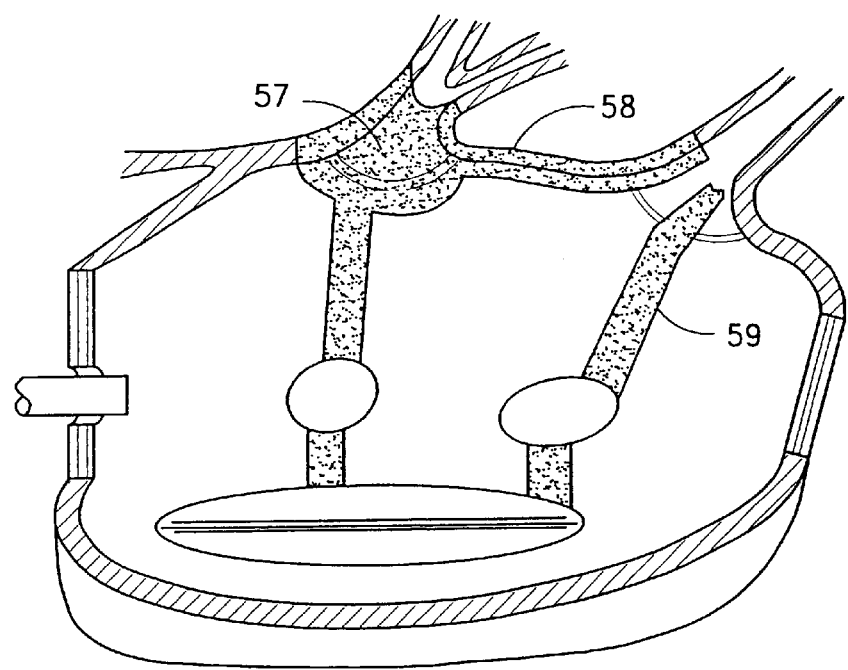
FIG. 9F shows a perspective view of a segmented left posterior atrial wall with a lesion pattern which results from combining the formation of two linear lesions according to FIG. 9B with the formation of a circumferential conduction block according to the methods and devices shown in FIGS. 8A–C.
Figure 9G:
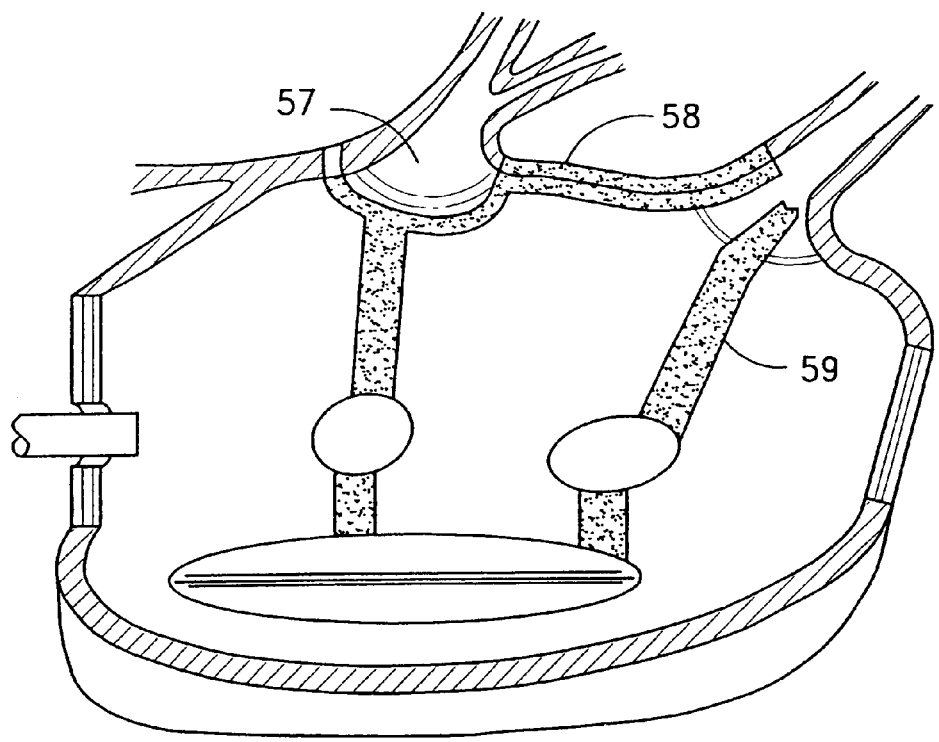
FIG. 9G shows a perspective view of a segmented left posterior atrial wall with a lesion pattern which results from combining the formation of two linear lesions according to FIG. 9B with the formation of a circumferential conduction block according to the methods and devices shown in FIGS. 8D–F.

In addition to the particular embodiments just shown and described by reference to FIGS. 9A–E, other methods are also contemplated for combining circumferential and linear conduction blocks device assemblies and uses in order to perform a less-invasive "maze"-type procedure. For example, FIG. 9F shows one particular lesion pattern which results by combining a circumferential conduction block, formed according to the previous embodiments of FIGS. 8A–C, with a pair of linear lesions which are formed according to the method illustrated by FIG. 9B. In a further example shown in FIG. 9G, another lesion pattern is formed by combining the pair of linear lesions of FIG. 9B with a circumferential conduction block formed according to the embodiments which are previously illustrated above by reference to FIGS. 9D–F. While the resulting lesion patterns of FIGS. 9F and 9G differ slightly as regards the particular geometry and position of the circumferential conduction block formed, the two variations are also similar in that the circumferential conduction block includes a circumferential path of atrial wall tissue. When such circumferential conduction blocks are formed between adjacent pulmonary vein ostia, shorter linear lesions are therefore sufficient to bridge the circumferential lesions during the overall "maze"-type procedure.

To this end, according to one contemplated less-invasive "maze"-type procedure (not shown) wherein multiple circumferential conduction blocks are formed in atrial wall tissue such that each pulmonary vein ostium is surrounded by and is electrically isolated with one circumferential conduction block. A series of four linear lesions may be formed between the various pairs of adjacent ostia and with just sufficient length to intersect with and bridge the corresponding adjacent circumferential blocks. A box-like conduction block is thereby formed by the four circumferential conduction blocks and the four bridging linear lesions. A fifth linear lesion may be also formed between at least a portion of the box-like conduction block and another predetermined location, such as for example the mitral value annulus.

Figure 9H:
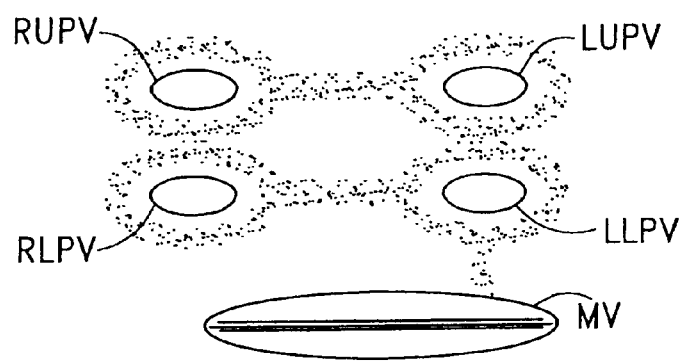
FIG. 9H shows a schematic perspective view of a left posterior atrial wall with one complete lesion pattern in a variation of a less-invasive "maze"-type procedure wherein circumferential conduction blocks are formed along circumferential paths of tissue along a left posterior atrial wall such that each circumferential conduction block surrounds a pulmonary vein ostium, each pair of vertically adjacent circumferential conduction blocks intersects, and each pair of horizontally adjacent circumferential conduction blocks are connected with one of two linear lesions extending between the respective pair of horizontally adjacent pulmonary vein ostia.

FIG. 9H shows yet a further variation for forming circumferential conduction blocks along atrial wall tissue around the pulmonary vein ostia during a less invasive "maze"-type procedure. According to this further variation, the circumferential conduction block patterns formed around each of two adjacent superior and inferior pulmonary vein ostia are shown in FIG. 9H to intersect, thereby alleviating the need for a linear lesion in order to form a conduction block between the ostia. Furthermore, the distances between the inferior and superior ostia, both on the right and left side of the posterior atrial wall, are believed to be significantly shorter than the distances between the two adjacent superior or inferior ostia. Therefore, FIG. 9H only shows the overlapping circumferential conduction blocks as just described to be positioned vertically between the inferior-superior pairs of adjacent ostia, and further shows linear lesions which are used to connect the right and left sided ostia of the superior and inferior pairs. In some instances these linear lesions will not be required to cure, treat or prevent a particular atrial arrhythmia condition. However, other combinations of these patterns are further contemplated, such as for example using only overlapping circumferential conduction blocks between all adjacent pairs of ostia in order to form the entire "maze"-type left atrial pattern.

Figure 10:
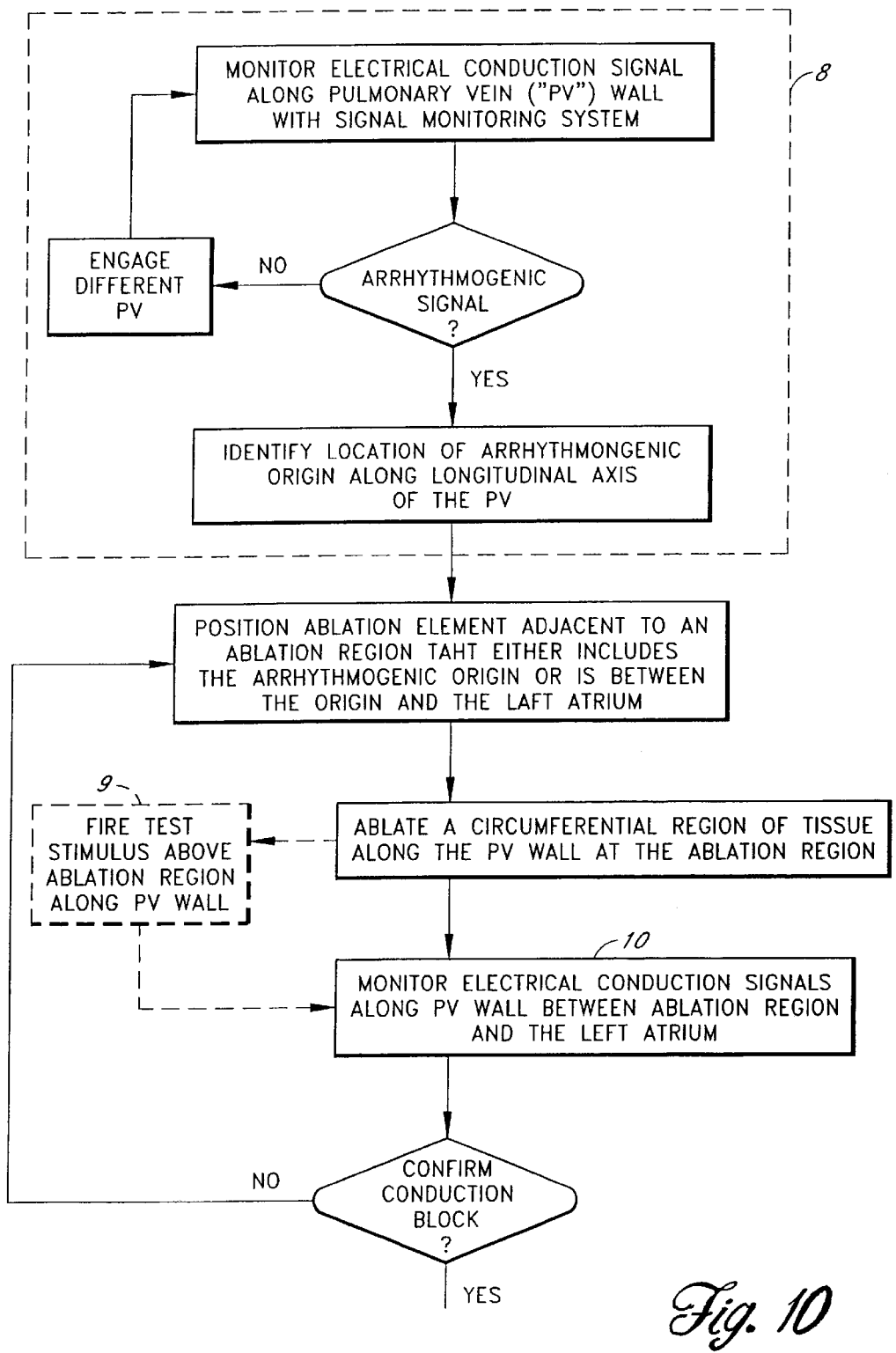
FIG. 10 diagrammatically shows a further method for using the circumferential ablation device assembly of the present invention to form a circumferential conduction block in a pulmonary vein wall, wherein signal monitoring and "post-ablation" test elements are used to locate an arrhythmogenic origin along the pulmonary vein wall and to test the efficacy of a circumferential conduction block in the wall, respectively.

FIG. 10 diagrammatically shows a further method for using a circumferential ablation device assembly wherein electrical signals along the pulmonary vein are monitored with a sensing element before and after ablation according to steps (8) and (9), respectively. Signals within the pulmonary vein are monitored prior to forming a conduction block, as indicated in step (8) in FIG. 10, in order to confirm that the pulmonary vein chosen contains an arrhythmogenic origin for atrial arrhythmia. Failure to confirm an arrhythmogenic origin in the pulmonary vein, particularly in the case of a patient diagnosed with focal arrhythmia, may dictate the need to monitor signals in another pulmonary vein in order to direct treatment to the proper location in the heart. In addition, monitoring the pre-ablation signals may be used to indicate the location of the arrhythmogenic origin of the atrial arrhythmia, which information helps determine the best location to form the conduction block. As such, the conduction block may be positioned to include and therefore ablate the actual focal origin of the arrhythmia, or may be positioned between the focus and the atrium in order to block aberrant conduction from the focal origin and into the atrial wall.

In addition or in the alternative to monitoring electrical conduction signals in the pulmonary vein prior to ablation, electrical signals along the pulmonary vein wall may also be monitored by the sensing element subsequent to circumferential ablation, according to step (9) of the method of FIG. 10. This monitoring method aids in testing the efficacy of the ablation in forming a complete conduction block against arrhythmogenic conduction. Arrhythmogenic firing from the identified focus will not be observed during signal monitoring along the pulmonary vein wall when taken below a continuous circumferential and transmural lesion formation, and thus would characterize a successful circumferential conduction block. In contrast, observation of such arrhythmogenic signals between the lesion and the atrial wall characterizes a functionally incomplete or discontinuous circumference (gaps) or depth (transmurality) which would potentially identify the need for a subsequent follow-up procedure, such as a second circumferential lesioning procedure in the ablation region.

A test electrode may also be used in a "post ablation" signal monitoring method according to step (10) of FIG. 10. In one particular embodiment not shown, the test electrode is positioned on the distal end portion of an elongate catheter body and is electrically coupled to a current source for firing a test signal into the tissue surrounding the test electrode when it is placed distally or "upstream" of the circumferential lesion in an attempt to simulate a focal arrhythmia. This test signal generally challenges the robustness of the circumferential lesion in preventing atrial arrhythmia from any such future physiologically generated aberrant activity along the suspect vein.

Further to the signal monitoring and test stimulus methods just described, such methods may be performed with a separate electrode or electrode pair located on the catheter distal end portion adjacent to the region of the circumferential ablation element, or may be performed using one or more electrodes which form the circumferential ablation element itself, as will be further developed below.

Circumferential Ablation Members

The designs for an expandable member and circumferential ablation element for use in a circumferential ablation device assembly have been described generically with reference to the embodiments shown in the previous Figures. Examples of more specific expandable member and ablation element embodiments which are adapted for use in such ablation device assemblies are further provided as follows.

Notwithstanding their somewhat schematic detail, the circumferential ablation members shown in the previous figures do illustrate one particular embodiment wherein a circumferential electrode element circumscribes an outer surface of an expandable member. The expandable member of the embodiments shown may take one of several different forms, although the expandable member is generally herein shown as an inflatable balloon that is coupled to an expansion actuator (175) which is a pressurizeable fluid source. The balloon is preferably made of a polymeric material and forms a fluid chamber which communicates with a fluid passageway (not shown in the figures) that extends proximally along the elongate catheter body and terminates proximally in a proximal fluid port that is adapted to couple to the pressurizeable fluid source.

In one expandable balloon variation, the balloon is constructed of a relatively inelastic plastics (e.g., polymers or monomers) such as a polyethylene ("PE"; preferably linear low density or high density or blends thereof), polyolefin copolymer ("POC"), polyethylene terepthalate ("PET"), polyimide, or a nylon material. In this construction, the balloon has a low radial yield or compliance over a working range of pressures and may be folded into a predetermined configuration when deflated in order to facilitate introduction of the balloon into the desired ablation location via known percutaneous catheterization techniques. In this variation, one balloon size may not suitably engage all pulmonary vein walls for performing the circumferential ablation methods herein described on all needy patients. Therefore, it is further contemplated that a kit of multiple ablation catheters, with each balloon working length having a unique predetermined expanded diameter, may be provided from which a treating physician may choose a particular device to meet a particular patient's pulmonary vein anatomy.

In an alternative expandable balloon variation, the balloon is constructed of a relatively compliant, elastomeric material, such as, for example (but not limited to), a silicone, latex, polyurethane, or mylar elastomer. In this construction, the balloon takes the form of a tubular member in the deflated, non-expanded state. When the elastic tubular balloon is pressurized with fluid such as in the previous, relatively non-compliant example, the material forming the wall of the tubular member elastically deforms and stretches radially to a predetermined diameter for a given inflation pressure. It is further contemplated that the compliant balloon may be constructed as a composite, such as, for example, a latex or silicone balloon skin which includes fibers, such as metal, Kevlar, or nylon fibers, which are embedded into the skin. Such fibers, when provided in a predetermined pattern such as a mesh or braid, may provide a controlled compliance along a preferred axis, preferably limiting longitudinal compliance of the expandable member while allowing for radial compliance.

It is believed that, among other features, the relatively compliant variation may provide a wide range of working diameters, which may allow for a wide variety of patients, or of vessels within a single patient, to be treated with just one or a few devices. Furthermore, this range of diameters is achievable over a relatively low range of pressures, which is believed to diminish a potentially traumatic vessel response that may otherwise be presented concomitant with higher pressure inflations, particularly when the inflated balloon is oversized to the vessel. In addition, the low-pressure inflation feature of this variation is suitable because the functional requirement of the expandable balloon is merely to engage the ablation element against a circumferential path along the inner lining of the pulmonary vein wall.

Moreover, a circumferential ablation member is adapted to conform to the geometry of the pulmonary vein ostium, at least in part by providing substantial compliance to the expandable member, as was shown and described previously by reference to FIGS. 8A–B. Further to this conformability to pulmonary vein ostium as provided in the specific design of FIGS. 8A–B, the working length L of expandable member (370) is also shown to include a taper which has a distally reducing outer diameter from a proximal end (372) to a distal end (374). In either a compliant or the non-compliant balloon, such a distally reducing tapered geometry adapts the circumferential ablation element to conform to the funneling geometry of the pulmonary veins in the region of their ostia in order to facilitate the formation of a circumferential conduction block there.

Further to the circumferential electrode element embodiment as shown variously throughout the previous illustrative Figures, the circumferential electrode element is coupled to an ablation actuator (190). Ablation actuator (190) generally includes a radio-frequency ("RF") current source (not shown) that is coupled to both the RF electrode element and also a ground patch (195) which is in skin contact with the patient to complete an RF circuit. In addition, ablation actuator (190) preferably includes a monitoring circuit (not shown) and a control circuit (not shown) which together use either the electrical parameters of the RF circuit or tissue parameters such as temperature in a feedback control loop to drive current through the electrode element during ablation. Also, where a plurality of ablation elements or electrodes in one ablation element are used, a switching means may be used to multiplex the RF current source between the various elements or electrodes.

FIGS. 11A–D show various patterns of electrically conductive, circumferential electrode bands as electrode ablation elements, each circumscribing an outer surface of the working length of an expandable member. FIGS. 11A–B show circumferential ablation member (550) to include a continuous circumferential electrode band (552) that circumscribes an outer surface of an expandable member (570). FIG. 11B more specifically shows expandable member (570) as a balloon which is fluidly coupled to a pressurizeable fluid source (175), and further shows electrode band (circumferential ablation element) (552) electrically coupled via electrically conductive lead (554) to ablation actuator (190). In addition, a plurality of apertures (572) are shown in the balloon skin wall of expandable member (570) adjacent to electrode band (552). The purpose of these apertures (572) is to provide a positive flow of fluid such as saline or ringers lactate fluid into the tissue surrounding the electrode band (552). Such fluid flow is believed to reduce the temperature rise in the tissue surrounding the electrode element during RF ablation.

The shapes shown collectively in FIGS. 11A–D allow for a continuous electrode band to circumscribe an expandable member's working length over a range of expanded diameters, a feature which is believed to be particularly useful with a relatively compliant balloon as the expandable member. In the particular embodiments of FIGS. 11A–D, this feature is provided primarily by a secondary shape given to the electrode band relative to the longitudinal axis of the working length of the expandable member. Electrode band (552) is thus shown in FIGS. 11A–B to take the specific secondary shape of a modified step curve. Other shapes than a modified step curve are also suitable, such as the serpentine or sawtooth secondary shapes shown respectively in FIGS. 11C–D. Other shapes in addition to those shown in FIGS. 11A–D and which meet the defined functional requirements are further contemplated.

In addition, the electrode band provided by the circumferential ablation elements shown in FIGS. 11C–D and also shown schematically in FIGS. 3–6B has a functional band width w relative to the longitudinal axis of the working length which is only required to be sufficiently wide to form a complete conduction block against conduction along the walls of the pulmonary vein in directions parallel to the longitudinal axis. In contrast, the working length L of the respective expandable element is adapted to securely anchor the distal end portion in place such that the ablation element is firmly positioned at a selected region of the pulmonary vein for ablation. Accordingly, the band width w is relatively narrow compared to the working length L of the expandable element, and the electrode band may thus form a relatively narrow equatorial band which has a band width that is less than two-thirds or even one-half of the working length of the expandable element. Additionally, it is to be noted here and elsewhere throughout the specification, that a narrow band may be placed at locations other than the equator of the expandable element, preferably as long as the band is bordered on both sides by a portion of the working length L.

In another aspect of the narrow equatorial band variation for the circumferential ablation element, the circumferential lesion formed may also be relatively narrow when compared to its own circumference, and may be less than two-thirds or even one-half its own circumference on the expandable element when expanded. In one arrangement which is believed to be suitable for ablating circumferential lesions in the pulmonary veins as conduction blocks, the band width w is less than 1 cm with a circumference on the working length when expanded that is greater than 1.5 cm.

FIGS. 12A–B show a further variation of a circumferential ablation element which is adapted to maintain a continuous circumferential lesion pattern over a range of expanded diameters and which includes electrode elements that form a relatively narrow equatorial band around the working length of an expandable balloon member. In this variation, a plurality of individual electrode/ablation elements (562) are included in the circumferential ablation element and are positioned in spaced arrangement along an equatorial band which circumscribes an outer surface of the expandable member's working length L.

The size and spacing between these individual electrode elements (562), when the balloon is expanded, is adapted to form a substantially continuous circumferential lesion in pulmonary vein wall tissue when in intimal contact adjacent thereto, and is further adapted to form such a lesion over a range of band diameters as the working length is adjusted between a variety of radially expanded positions. Each individual electrode element (562) has two opposite ends (563,564), respectively, along a long axis LA and also has a short axis SA, and is positioned such that the long axis LA is at an acute angle relative to the longitudinal axis LA of the elongate catheter body and expandable member (560). At least one of the ends (563,564) along the long axis LA overlaps with an end of another adjacent individual electrode element, such that there is a region of overlap along their circumferential aspect, i.e., there is a region of overlap along the circumferential coordinates. The terms "region of overlap along their circumferential coordinate" are herein intended to mean that the two adjacent ends each are positioned along the working length with a circumferential and also a longitudinal coordinate, wherein they share a common circumferential coordinate. In this arrangement, the circumferential compliance along the working length which accompanies radial expansion of the expandable member also moves the individual electrode elements apart along the circumferential axis. However, the spaced, overlapping arrangement described allows the individual ablation elements to maintain a certain degree of their circumferential overlap, or at least remain close enough together, such that a continuous lesion may be formed without gaps between the elements.

The construction for suitable circumferential electrode elements in the RF variations herein described, such as the various electrode embodiments described with reference to FIGS. 11A–12B, may comprise a metallic material deposited on the outer surface of the working length using conventional techniques, such as by plasma depositing, sputter coating, chemical vapor deposition, other known techniques which are equivalent for this purpose, or otherwise affixing a metallic shaped member onto the outer surface of the expandable member such as through known adhesive bonding techniques. Other RF electrode arrangements are also considered, so long as they form a circumferential conduction block as previously described. For example, a balloon skin may itself be metallized, such as by mixing conductive metal, including but not limited to gold, platinum, or silver, with a plastic (e.g., polymer) to form a compounded, conductive matrix as the balloon skin.

Still further to the RF electrode embodiments, another circumferential ablation member variation (not shown) may also include an expandable member, such as an inflatable balloon, that includes a porous skin that is adapted to allow fluid, such as hypertonic saline solution, to pass from an internal chamber defined by the skin and outwardly into surrounding tissues. Such a porous skin may be constructed according to several different methods, such as by forming holes in an otherwise contiguous plastic (e.g., polymeric) material, including mechanically drilling or using laser energy, or the porous skin may simply be an inherently porous membrane. In any case, by electrically coupling the fluid within the porous balloon skin to an RF current source (preferably monopolar), the porous region of the expandable member serves as an RF electrode wherein RF current flows outwardly through the pores via the conductive fluid. In addition, it is further contemplated that a porous outer skin may be provided externally of another, separate expandable member, such as a separate expandable balloon, wherein the conductive fluid is contained in a region between the porous outer skin and the expandable member contained therein. Various other "fluid electrode" designs than those specifically herein described may also be suitable according to one of ordinary skill upon review of this disclosure.

In the alternative, or in addition to the RF electrode variations just described, the circumferential ablation element may also include other ablative energy sources or sinks, and particularly may include a thermal conductor that circumscribes the outer circumference of the working length of an expandable member. Examples of suitable thermal conductor arrangements include a metallic element which may, for example, be constructed as previously described for the more detailed RF embodiments above. However, in the thermal conductor embodiment such a metallic element would be generally either resistively heated in a closed loop circuit internal to the catheter, or conductively heated by a heat source coupled to the thermal conductor. In the latter case of conductive heating of the thermal conductor with a heat source, the expandable member may be, for example, a plastic (e.g., polymeric) balloon skin which is inflated with a fluid that is heated either by a resistive coil or by bipolar RF current. In any case, it is believed that a thermal conductor on the outer surface of the expandable member is suitable when it is adapted to heat tissue adjacent thereto to a temperature between 40° and 80° Celsius.

Further to the thermal conduction variation for the circumferential ablation element, the perfusion balloon embodiment as shown in FIGS. 6A–B may be particularly useful in such a design. It is believed that ablation through increased temperatures, as provided by example above may also enhance coagulation of blood in the pulmonary vein adjacent to the expandable member, which blood would otherwise remain stagnant without such a perfusion feature.

Figure 13:
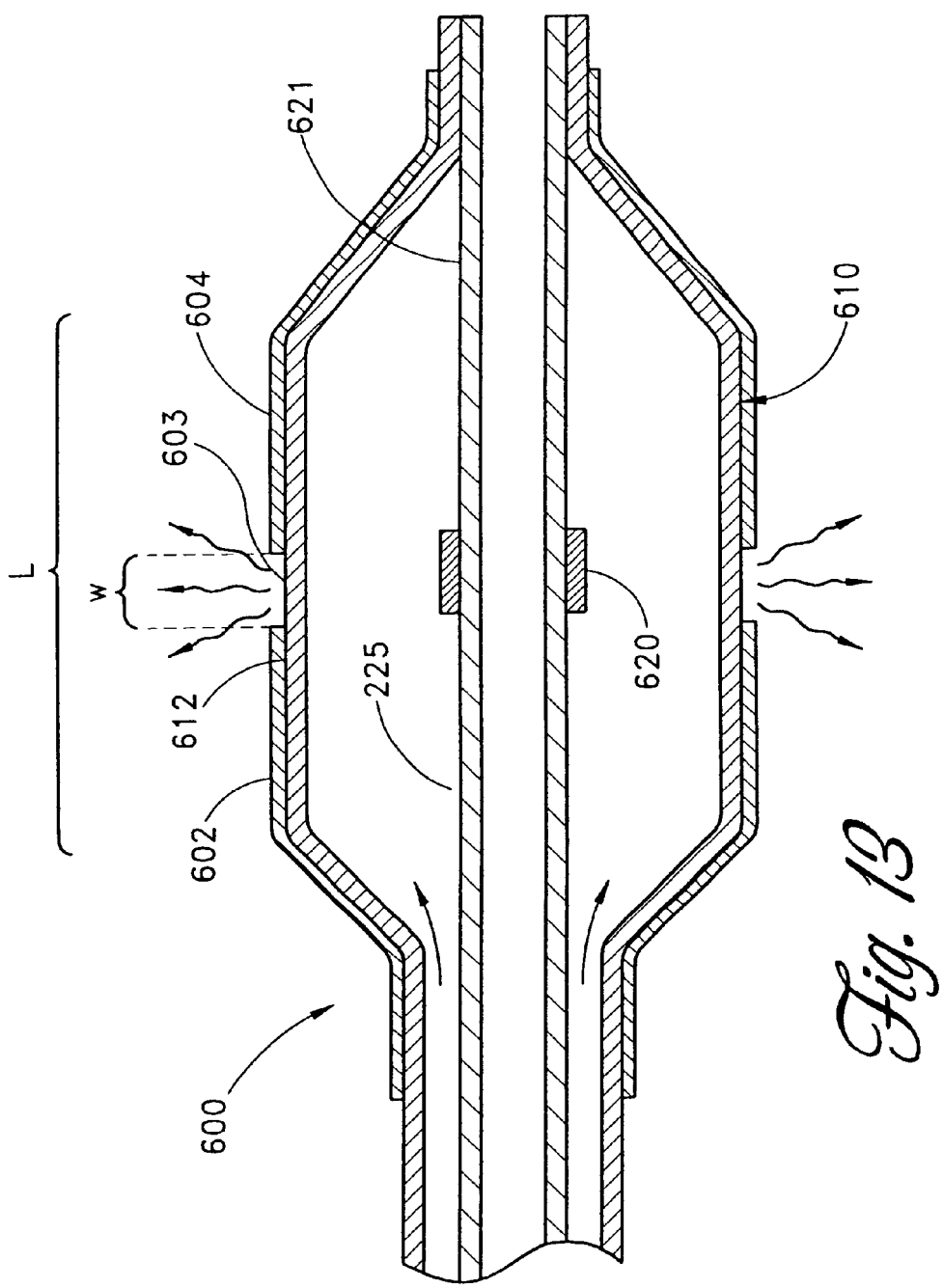
FIG. 13 shows a cross-sectional view of another circumferential ablation member for use in a circumferential ablation device assembly for pulmonary vein isolation, wherein the circumferential ablation element circumscribes an outer surface of an expandable member substantially along its working length and is insulated at both the proximal and the distal ends of the working length to thereby form an uninsulated equatorial band in a middle region of the working length or otherwise circumferential region of the working length which is bounded both proximally and distally by end portions of the working length, which member is adapted to ablate a circumferential path of tissue engaged by the equatorial band.

One further circumferential ablation element design which is believed to be highly useful in performing the ablation methods herein described is shown in FIG. 13 to include a circumferential ablation member (600) with two insulators (602,604) that encapsulate the proximal and distal ends, respectively, of the working length L of an expandable member (610). In the particular embodiment shown, the insulators (602,604) are thermal insulators, such as a thermal insulator comprising a Teflon material. Expandable member (610) is an inflatable balloon which has a balloon skin (612) that is thermally conductive to surrounding tissue when inflated with a heated fluid which may contain a radiopaque agent, saline fluid, ringers lactate, combinations thereof, other known biocompatible fluids having acceptable heat transfer properties for these purposes, further to the thermal conductor embodiments previously described. By providing these spaced insulators, a circumferential ablation element is formed as an equatorial band (603) of uninsulated balloon skin is located between the opposite insulators. In this configuration, the circumferential ablation element is able to conduct heat externally of the balloon skin much more efficiently at the uninsulated equatorial band (603) than at the insulated portions, and thereby is adapted to ablate only a circumferential region of tissue in a pulmonary vein wall which is adjacent to the equatorial band. It is further noted that this embodiment is not limited to an "equatorial" placement of the ablation element. Rather, a circumferential band may be formed anywhere along the working length of the expandable member and circumscribing the longitudinal axis of the expandable member as previously described.

FIG. 13 further shows use of a radiopaque marker (620) to identify the location of the equatorial band (603) in order to facilitate placement of that band at a selected ablation region of a pulmonary vein via X-ray visualization. Radiopaque marker (620) is opaque under X-ray, and may be constructed, for example, of a radiopaque metal such as gold, platinum, or tungsten, or may comprise a radiopaque plastic (e.g., polymer) such as a metal loaded polymer. FIG. 13 shows radiopaque marker (620) positioned coaxially over an inner tubular member (621) which is included in a coaxial catheter design as would be apparent to one of ordinary skill. Such a radiopaque marker may also be combined with the other embodiments herein shown and described. To note, when the circumferential ablation member which forms an equatorial band includes a metallic electrode element, such electrode may itself be radiopaque and may not require use of a separate marker as just described.

The thermal insulator embodiment just described by reference to FIG. 13 is illustrative of a broader embodiment, wherein a circumferential ablation member has an ablating surface along the entire working length of an expandable member, but is shielded from releasing ablative energy into surrounding tissues except for along an unshielded or uninsulated equatorial band. As such, the insulator embodiment contemplates other ablation elements, such as the RF embodiments previously described above, which are provided along the entire working length of an expandable member and which are insulated at their ends to selectively ablate tissue only about an uninsulated equatorial band.

In a further example using the insulator embodiment in combination with a circumferential RF electrode embodiment, a metallized balloon which includes a conductive balloon skin may have an electrical insulator, such as a plastic (e.g., polymeric) coating, at each end of the working length and thereby selectively ablate tissue with electricity flowing through the uninsulated equatorial band. In this and other insulator embodiments, it is further contemplated that the insulators described may be only partial and still provide the equatorial band result. For instance, in the conductive RF electrode balloon case, a partial electrical insulator will allow a substantial component of current to flow through the uninsulated portion due to a "shorting" response to the lower resistance in that region.

In still a further example of an insulator combined with an RF ablation electrode, a porous membrane comprises the entire balloon skin of an expandable member. By insulating the proximal and distal end portions of the working length of the expandable member, only the pores in the unexposed equatorial band region are allowed to effuse the electrolyte which carries an ablative RF current.

Further to the expandable member design for use in a circumferential ablation member as herein described, other expandable members than a balloon are also considered suitable. For example, in one expandable cage embodiment shown in FIG. 14, cage (650) comprises coordinating wires (651) and is expandable to engage a desired ablation region in a pulmonary vein.

The radial expansion of cage (650) is accomplished as follows. Sheath (652) is secured around the wires proximally of cage (650). However, core (653), which may be a metallic mandrel such as stainless steel, extends through sheath (652) and distally within cage (650) wherein it terminates in a distal tip (656). Wires (651) are secured to distal tip (656), for example, by soldering, welding, adhesive bonding, heat shrinking a plastic (e.g., polymeric) member over the wires, or any combination of these methods. Core (653) is slidable within sheath (652), and may, for example, be housed within a tubular lumen (not shown) within sheath (652), the wires being housed between a coaxial space between the tubular lumen and sheath (652). By moving the sheath (652) relative to core (653) and distal tip (656) (shown by arrows in FIG. 14), the cage (650) is collapsible along its longitudinal axis in order to force an outward radial bias (also shown with arrows in FIG. 14) to wires (651) in an organized fashion to formed a working length of cage (650) which is expanded (not shown).

Figure 14:
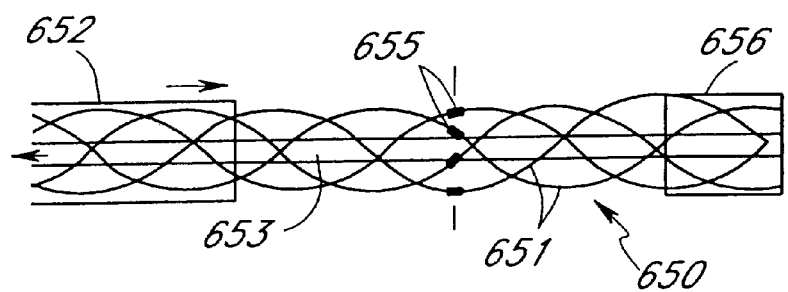
FIG. 14 shows a perspective view of another circumferential ablation member which is adapted for use in a circumferential ablation device assembly for pulmonary vein isolation, wherein the expandable member is shown to be a cage of coordinating wires which are adapted to be adjusted from a radially collapsed position to a radially expanded position in order to engage electrode elements on the wires about a circumferential pattern of tissue to be ablated.

Further to the particular expandable cage embodiment shown in FIG. 14, a plurality of ablation electrodes (655) is shown, each being positioned on one of wires (651) and being similarly located along the longitudinal axis of the cage (650). The radial bias given to wires (651) during expansion, together with the location of the ablation electrodes (655), serves to position the plurality of ablation electrodes/elements (655) along a circumferential, equatorial band along the expanded working length of cage (650). The wires forming a cage according to this embodiment may also have another predetermined shape when in the radially expanded position. For example, a taper similar to that shown for expandable member (370) in FIGS. 8A–B may be formed by expanding cage (650), wherein the ablation element formed by ablation electrodes (655) may be positioned between the proximal end and the distal end of the taper.

Further to the construction of the embodiment shown in FIG. 14, wires (651) are preferably metal, and may comprise stainless steel or a superelastic metal alloy, such as an alloy of nickel and titanium, or a combination of both. Regarding the case of nickel and titanium construction for wires (655), a separate electrical conductor may be required in order to actuate ablation electrodes (655) to efficiently emit ablative current into surrounding tissues. In the case where wires (651) are constructed of stainless steel, they may also serve as electrical conductors for ablation electrodes (655). Further to the stainless steel design, the wires (651) may be coated with an electrical insulator to isolate the electrical flow into surrounding tissues at the site of the ablation electrodes (655). Moreover, the ablation electrodes (655) in the stainless steel wire variation may be formed simply by removing electrical insulation in an isolated region to allow for current to flow into tissue only from that exposed region.

In a further cage embodiment (not shown) to that shown in FIG. 14, a circumferential strip of electrodes may also be secured to the cage (650) such that the strip circumscribes the cage at a predetermined location along the cage's longitudinal axis. By expanding cage (650) as previously described, the strip of electrodes are adapted to take a circumferential shape according to the shape of the expanded cage (650). Such an electrode strip is preferably flexible, such that it may be easily reconfigured when the cage is adjusted between the radially collapsed and expanded positions and such that the strip may be easily advanced and withdrawn with the cage within the delivery sheath. Furthermore, the electrode strip may be a continuous circumferential electrode such as a conductive spring coil, or may be a flexible strip which includes several separate electrodes along its circumferential length. In the latter case, the flexible strip may electrically couple all of the electrodes to a conductive lead that interfaces with a drive circuit, or each electrode may be separately coupled to one or more such conductive leads.

Figure 15:
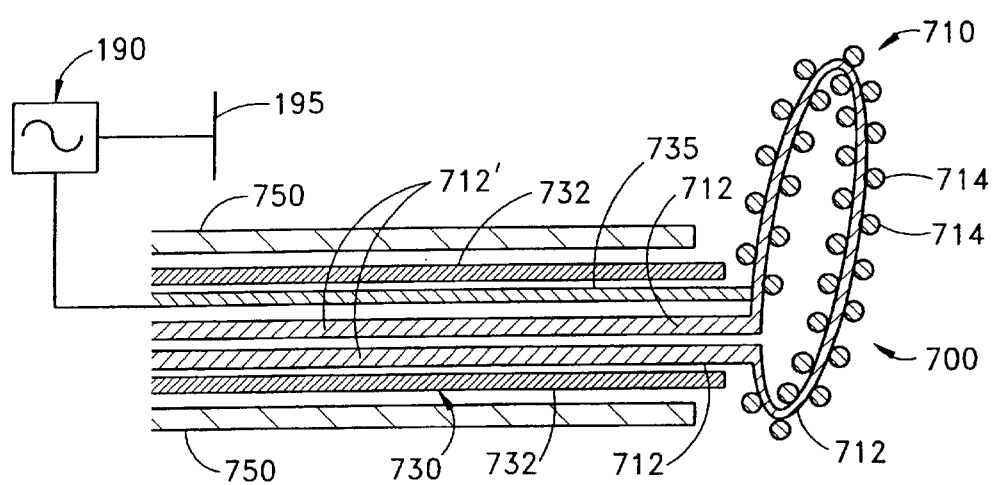
FIG. 15 shows a cross-sectional view of another circumferential ablation element which is adapted for use in a circumferential ablation device assembly for pulmonary vein isolation. A superelastic, looped electrode element is shown at the distal end of a pusher and is adapted to circumferentially engage pulmonary vein wall tissue to form a circumferential lesion as a conduction block that circumscribes the pulmonary vein lumen.

Another circumferential ablation element adapted for use in a circumferential conduction block assembly of the type herein described is shown in FIG. 15, wherein circumferential ablation member (700) includes a looped member (710) attached, preferably by heat shrinking, to a distal end of a pusher (730). Looped member (710) and pusher (730) are slidably engaged within delivery sheath (750) such that looped member (710) is in a first collapsed position when positioned and radially confined within delivery sheath (750), and expands to a second expanded position when advanced distally from delivery sheath (750).

Looped member (710) is shown in more detail in FIG. 15 to include a core (712) which is constructed of a superelastic metal alloy such as a nickel-titanium alloy and which has a looped portion with shape memory in the looped configuration. This looped configuration is shown in FIG. 15 to be in a plane which is off-axis, preferably perpendicular, to the longitudinal axis of the pusher (730). This off-axis orientation of the loop is adapted to engage a circumferential path of tissue along a pulmonary vein wall which circumscribes the pulmonary vein lumen when the looped member (710) is delivered from the delivery sheath (750) when the delivery sheath is positioned within the vein lumen parallel to its longitudinal axis. An ablation electrode (714) is also shown in FIG. 15 as a metallic coil which is wrapped around core (712) in its looped portion.

Pusher (730) is further shown in FIG. 15 to include a tubular pusher member (732) which is heat shrunk over two ends (712') of core (712) which extend proximally of looped member (710) through pusher (730) in the particular variation shown. While in this embodiment core (712) extends through the pusher in order to provide stiffness to the composite design for the pusher, it is further contemplated that the superelastic metal of the core may be replaced or augmented in the pusher region with another different mandrel or pusher core (not shown), such as a stiffer stainless steel mandrel. Also shown within pusher (730) is an electrically conductive lead (735) which is coupled to the ablation electrode (714) and which is also adapted in a proximal region of the pusher (not shown) to couple to an ablation actuator (190) such as an RF current source (shown schematically).

Ultrasonic Energy Source

FIGS. 16A–19B show various specific embodiments of a broader circumferential ablation device assembly that utilizes an ultrasonic energy source to ablate tissue. The present circumferential ablation device has particular utility in connection with forming a circumferential lesion within or about a pulmonary vein ostium or within the vein itself in order to form a circumferential conductive block. This application of the present ablation device, however, is merely exemplifying of one preferred mode of use, and it is understood that those skilled in the art can readily adapt the present ablation device for applications in other body spaces.

As common to each of the following embodiments, a source of acoustic energy is provided for a delivery device that also includes an anchoring mechanism. In one mode, the anchoring mechanism comprises an expandable member that also positions the acoustic energy source within the body; however, other anchoring and positioning devices may also be used, such as, for example, a basket mechanism. In a more specific form, the acoustic energy source is located within the expandable member and the expandable member is adapted to engage a circumferential path of tissue either about or along a pulmonary vein in the region of its ostium along a left atrial wall. The acoustic energy source in turn is acoustically coupled to the wall of the expandable member and thus to the circumferential region of tissue engaged by the expandable member wall by emitting a circumferential and longitudinally collimated ultrasound signal when actuated by an acoustic energy driver. The use of acoustic energy, and particularly ultrasonic energy, offers the advantage of simultaneously applying a dose of energy sufficient to ablate a relatively large surface area within or near the heart to a desired heating depth without exposing the heart to a large amount of current. For example, a collimated ultrasonic transducer can form a lesion, which has about a 1.5 mm width, about a 2.5 mm diameter lumen, such as a pulmonary vein and of a sufficient depth to form an effective conductive block. It is believed that an effective conductive block can be formed by producing a lesion within the tissue that is transmural or substantially transmural. Depending upon the patient as well as the location within the pulmonary vein ostium, the lesion may have a depth of 1 millimeter to 10 millimeters. It has been observed that the collimated ultrasonic transducer can be powered to provide a lesion having these parameters so as to form an effective conductive block between the pulmonary vein and the posterior wall of the left atrium.

With specific reference now to the embodiment illustrated in FIGS. 16A through 16D, a circumferential ablation device assembly (800) includes an elongate body (802) with proximal and distal end portions (810,812), an expandable balloon (820) located along the distal end portion (812) of elongate body (802), and a circumferential ultrasound transducer (830) which forms a circumferential ablation member which is acoustically coupled to the expandable balloon (820). In more detail, FIGS. 16A–C variously show elongate body (802) to include guidewire lumen (804), inflation lumen (806), and electrical lead lumen (808). The ablation device, however, can be of a self steering type rather than an over-the-wire type device.

Each lumen extends between a proximal port (not shown) and a respective distal port, which distal ports are shown as distal guidewire port (805) for guidewire lumen (804), distal inflation port (807) for inflation lumen (806), and distal lead port (809) for electrical lead lumen (808). Although the guidewire, inflation and electrical lead lumens are generally arranged in a side-by-side relationship, the elongate body (802) can be constructed with one or more of these lumens arranged in a coaxial relationship, or in any of a wide variety of configurations that will be readily apparent to one of ordinary skill in the art.

In addition, the elongate body (802) is also shown in FIGS. 16A and 16C to include an inner member (803) which extends distally beyond distal inflation and lead ports (807, 809), through an interior chamber formed by the expandable balloon (820), and distally beyond expandable balloon (820) where the elongate body terminates in a distal tip. The inner member (803) forms the distal region for the guidewire lumen (804) beyond the inflation and lead ports, and also provides a support member for the cylindrical ultrasound transducer (830) and for the distal neck of the expansion balloon, as described in more detail below.

One more detailed construction for the components of the elongate body (802) which is believed to be suitable for use in transeptal left atrial ablation procedures is as follows. The elongate body (802) itself may have an outer diameter provided within the range of from about 5 French to about 10 French, and more preferable from about 7 French to about 9 French. The guidewire lumen preferably is adapted to slidably receive guidewires ranging from about 0.010 inch to about 0.038 inch in diameter, and preferably is adapted for use with guidewires ranging from about 0.018 inch to about 0.035 inch in diameter. Where a 0.035 inch guidewire is to be used, the guidewire lumen preferably has an inner diameter of 0.040 inch to about 0.042 inch. In addition, the inflation lumen preferably has an inner diameter of about 0.020 inch in order to allow for rapid deflation times, although may vary based upon the viscosity of inflation medium used, length of the lumen, and other dynamic factors relating to fluid flow and pressure.

In addition to providing the requisite lumens and support members for the ultrasound transducer assembly, the elongate body (802) of the present embodiment must also be adapted to be introduced into the left atrium such that the distal end portion with balloon and transducer may be placed within the pulmonary vein ostium in a percutaneous translumenal procedure, and even more preferably in a transeptal procedure as otherwise herein provided. Therefore, the distal end portion (812) is preferably flexible and adapted to track over and along a guidewire seated within the targeted pulmonary vein. In one further more detailed construction which is believed to be suitable, the proximal end portion is adapted to be at least 30% more stiff than the distal end portion. According to this relationship, the proximal end portion may be suitably adapted to provide push transmission to the distal end portion while the distal end portion is suitably adapted to track through bending anatomy during in vivo delivery of the distal end portion of the device into the desired ablation region.

Notwithstanding the specific device constructions just described, other delivery mechanisms for delivering the ultrasound ablation member to the desired ablation region are also contemplated. For example, while the FIG. 16A variation is shown as an "over-the-wire" catheter construction, other guidewire tracking designs may be suitable substitutes, such as, for example, catheter devices which are known as "rapid exchange" or "monorail" variations wherein the guidewire is only housed coaxially within a lumen of the catheter in the distal regions of the catheter. In another example, a deflectable tip design may also be a suitable substitute and which is adapted to independently select a desired pulmonary vein and direct the transducer assembly into the desired location for ablation. Further to this latter variation, the guidewire lumen and guidewire of the FIG. 16A variation may be replaced with a "pullwire" lumen and associated fixed pullwire which is adapted to deflect the catheter tip by applying tension along varied stiffness transitions along the catheter's length. Still further to this pullwire variation, acceptable pullwires may have a diameter within the range from about 0.008 inch to about 0.020 inch, and may further include a taper, such as, for example, a tapered outer diameter from about 0.020 inch to about 0.008 inch.

More specifically regarding expandable balloon (820) as shown in varied detail between FIGS. 16A and 16C, a central region (822) is generally coaxially disposed over the inner member (803) and is bordered at its end neck regions by proximal and distal adaptions (824,826). The proximal adaption (824) is sealed over elongate body (802) proximally of the distal inflation and the electrical lead ports (807,809), and the distal adaption (826) is sealed over inner member (803). According to this arrangement, a fluid tight interior chamber is formed within expandable balloon (820). This interior chamber is fluidly coupled to a pressurizeable fluid source (not shown) via inflation lumen (806). In addition to the inflation lumen (806), electrical lead lumen (808) also communicates with the interior chamber of expandable balloon (820) so that the ultrasound transducer (830), which is positioned within that chamber and over the inner member (803), may be electrically coupled to an ultrasound drive source or actuator, as will be provided in more detail below.

The expandable balloon (820) may be constructed from a variety of known materials, although the balloon (820) preferably is adapted to conform to the contour of a pulmonary vein ostium. For this purpose, the balloon material can be of the highly compliant variety, such that the material elongates upon application of pressure and takes on the shape of the body lumen or space when fully inflated. Suitable balloon materials include elastomers, such as, for example, but without limitation, Silicone, latex, or low durometer polyurethane (for example, a durometer of about 80 A).

In addition or in the alternative to constructing the balloon of highly compliant material, the balloon (820) can be formed to have a predefined fully inflated shape (i.e., be preshaped) to generally match the anatomic shape of the body lumen in which the balloon is inflated. For instance, as described below in greater detail, the balloon can have a distally tapering shape to generally match the shape of a pulmonary vein ostium, and/or can include a bulbous proximal end to generally match a transition region of the atrium posterior wall adjacent to the pulmonary vein ostium. In this manner, the desired seating within the irregular geometry of a pulmonary vein or vein ostium can be achieved with both compliant and non-compliant balloon variations.

Notwithstanding the alternatives which may be acceptable as just described, the balloon (820) is preferably constructed to exhibit at least 300% expansion at 3 atmospheres of pressure, and more preferably to exhibit at least 400% expansion at that pressure. The term "expansion" is herein intended to mean the balloon outer diameter after pressurization divided by the balloon inner diameter before pressurization, wherein the balloon inner diameter before pressurization is taken after the balloon is substantially filled with fluid in a taught configuration. In other words, "expansion" is herein intended to relate to change in diameter that is attributable to the material compliance in a stress strain relationship. In one more detailed construction which is believed to be suitable for use in most conduction block procedures in the region of the pulmonary veins, the balloon is adapted to expand under a normal range of pressure such that its outer diameter may be adjusted from a radially collapsed position of about 5 millimeters to a radially expanded position of about 2.5 centimeters (or approximately 500% expansion ratio).

The ablation member, which is illustrated in FIGS. 16A–D, takes the form of annular ultrasonic transducer (830). In the illustrated embodiment, the annular ultrasonic transducer (830) has a unitary cylindrical shape with a hollow interior (i.e., is tubular shaped); however, the transducer applicator (830) can have a generally annular shape and be formed of a plurality of segments. For instance, the transducer applicator (830) can be formed by a plurality of tube sectors that together form an annular shape. The tube sectors can also be of sufficient arc lengths so as when joined together, the sectors assembly forms a "clover-leaf" shape. This shape is believed to provide overlap in heated regions between adjacent elements. The generally annular shape can also be formed by a plurality of planar transducer segments which are arranged in a polygon shape (e.g., hexagon). In addition, although in the illustrated embodiment the ultrasonic transducer comprises a single transducer element, the transducer applicator can be formed of a multi-element array, as described in greater detail below.

As is shown in detail in FIG. 16D, cylindrical ultrasound transducer (830) includes a tubular wall (831) which includes three concentric tubular layers. The central layer (832) is a tubular shaped member of a piezoceramic or piezoelectric crystalline material. The transducer preferably is made of type PZT-4, PZT-5 or PZT-8, quartz or Lithium-Niobate type piezoceramic material to ensure high power output capabilities. These types of transducer materials are commercially available from Stavely Sensors, Inc. of East Hartford, Conn., or from Valpey-Fischer Corp. of Hopkinton, Mass.

The outer and inner tubular members (833,834) enclose central layer (832) within their coaxial space and are constructed of an electrically conductive material. In the illustrated embodiment, these transducer electrodes (833, 834) comprise a metallic coating, and more preferably a coating of nickel, copper, silver, gold, platinum, or alloys of these metals.

One more detailed construction for a cylindrical ultrasound transducer for use in the present application is as follows. The length of the transducer (830) or transducer assembly (e.g., multi-element array of transducer elements) desirably is selected for a given clinical application. In connection with forming circumferential condition blocks in cardiac or pulmonary vein wall tissue, the transducer length can fall within the range of approximately 2 mm up to greater than 10 mm, and preferably equals about 5 mm to 10 mm. A transducer accordingly sized is believed to form a lesion of a width sufficient to ensure the integrity of the formed conductive block without undue tissue ablation. For other applications, however, the length can be significantly longer.

Likewise, the transducer outer diameter desirably is selected to account for delivery through a particular access path (e.g., percutaneously and transeptally), for proper placement and location within a particular body space, and for achieving a desired ablation effect. In the given application within or proximate of the pulmonary vein ostium, the transducer (830) preferably has an outer diameter within the range of about 1.8 mm to greater than 2.5 mm. It has been observed that a transducer with an outer diameter of about 2 mm generates acoustic power levels approaching 20 Watts per centimeter radiator or greater within myocardial or vascular tissue, which is believed to be sufficient for ablation of tissue engaged by the outer balloon for up to about 2 cm outer diameter of the balloon. For applications in other body spaces, the transducer applicator (830) may have an outer diameter within the range of about 1 mm to greater than 3–4 mm (e.g., as large as 1 to 2 cm for applications in some body spaces).

The central layer (832) of the transducer (830) has a thickness selected to produce a desired operating frequency. The operating frequency will vary of course depending upon clinical needs, such as the tolerable outer diameter of the ablation and the depth of heating, as well as upon the size of the transducer as limited by the delivery path and the size of the target site. As described in greater detail below, the transducer (830) in the illustrated application preferably operates within the range of about 5 MHz to about 20 MHz, and more preferably within the range of about 7 MHz to about 10 MHz. Thus, for example, the transducer can have a thickness of approximately 0.3 mm for an operating frequency of about 7 MHz (i.e., a thickness generally equal to ½ the wavelength associated with the desired operating frequency).

The transducer (830) is vibrated across the wall thickness and to radiate collimated acoustic energy in the radial direction. For this purpose, as best seen in FIGS. 16A and 16D, the distal ends of electrical leads (836,837) are electrically coupled to outer and inner tubular members or electrodes (833,834), respectively, of the transducer (830), such as, for example, by soldering the leads to the metallic coatings or by resistance welding. In the illustrated embodiment, the electrical leads are 4–8 mil (0.004 to 0.008 inch diameter) silver wire or the like.

The proximal ends of these leads are adapted to couple to an ultrasonic driver or actuator (840), which is schematically illustrated in FIG. 16D. FIGS. 16A–D further show leads (836,837) as separate wires within electrical lead lumen (808), in which configuration the leads must be well insulated when in close contact. Other configurations for leads (836,837) are therefore contemplated. For example, a coaxial cable may provide one cable for both leads which is well insulated as to inductance interference. Or, the leads may be communicated toward the distal end portion (812) of the elongate body through different lumens which are separated by the catheter body.

The transducer also can be sectored by scoring or notching the outer transducer electrode (833) and part of the central layer (832) along lines parallel to the longitudinal axis L of the transducer (830), as illustrated in FIG. 16E. A separate electrical lead connects to each sector in order to couple the sector to a dedicated power control that individually excites the corresponding transducer sector. By controlling the driving power and operating frequency to each individual sector, the ultrasonic driver (840) can enhance the uniformity of the ultrasonic beam around the transducer (830), as well as can vary the degree of heating (i.e., lesion control) in the angular dimension.

The ultrasound transducer just described is combined with the overall device assembly according to the present embodiment as follows. In assembly, the transducer (830) desirably is "air-backed" to produce more energy and to enhance energy distribution uniformity, as known in the art. In other words, the inner member (803) does not contact an appreciable amount of the inner surface of transducer inner tubular member (834). This is because the piezoelectric crystal which forms central layer (832) of ultrasound transducer (830) is adapted to radially contract and expand (or radially "vibrate") when an alternating current is applied from a current source and across the outer and inner tubular electrodes (833,834) of the crystal via the electrical leads (836,837). This controlled vibration emits the ultrasonic energy which is adapted to ablate tissue and form a circumferential conduction block according to the present embodiment. Therefore, it is believed that appreciable levels of contact along the surface of the crystal may provide a dampening effect which would diminish the vibration of the crystal and thus limit the efficiency of ultrasound transmission.

For this purpose, the transducer (830) seats coaxial about the inner member (803) and is supported about the inner member (803) in a manner providing a gap between the inner member (803) and the transducer inner tubular member (834). That is, the inner tubular member (834) forms an interior bore (835) which loosely receives the inner member (803). Any of a variety of structures can be used to support the transducer (830) about the inner member (803). For instance, spacers or splines can be used to coaxially position the transducer (830) about the inner member (803) while leaving a generally annular space between these components. In the alternative, other conventional and known approaches to support the transducer can also be used. For instance, O-rings that circumscribe the inner member (803) and lie between the inner member (803) and the transducer (830) can support the transducer (830) in a manner similar to that illustrated in U.S. Pat. Nos. 5,606,974; 5,620,479.

In the illustrated embodiment, a stand-off (838) is provided in order to ensure that the transducer (830) has a radial separation from the inner member (803) to form a gap filled with air and/or other fluid. In one preferred mode shown in FIG. 16C, stand-off (838) is a tubular member with a plurality of circumferentially spaced outer splines (839) which hold the majority of the transducer inner surface away from the surface of the stand-off between the splines, thereby minimizing dampening affects from the coupling of the transducer to the catheter. The tubular member which forms a stand-off such as stand-off (838) in the FIG. 16D embodiment may also provide its inner bore as the guidewire lumen in the region of the ultrasound transducer, in the alternative to providing a separate stand-off coaxially over another tubular member which forms the inner member, such as according to the FIG. 16D embodiment.

In a further mode, the elongate body (802) can also include additional lumens which lie either side by side to or coaxial with the guidewire lumen (804) and which terminate at ports located within the space between the inner member (803) and the transducer (830). A cooling medium can circulate through space defined by the stand-off (838) between the inner member (803) and the transducer (830) via these additional lumens. By way of example, carbon dioxide gas, circulated at a rate of 5 liters per minute, can be used as a suitable cooling medium to maintain the transducer at a lower operating temperature. It is believed that such thermal cooling would allow more acoustic power to transmit to the targeted tissue without degradation of the transducer material.

The transducer (830) desirably is electrically and mechanically isolated from the interior of the balloon (820). Again, any of a variety of coatings, sheaths, sealants, tubings and the like may be suitable for this purpose, such as those described in U.S. Pat. Nos. 5,620,479 and 5,606,974. In the illustrated embodiment, as best illustrated in FIG. 16C, a conventional, flexible, acoustically compatible, and medical grade epoxy (842) is applied over the transducer (830). The epoxy (842) may be, for example, Epotek 301, Epotek 310, which is available commercially from Epoxy Technology, or Tracon FDA-8. In addition, a conventional sealant, such as, for example, General Electric Silicone II gasket glue and sealant, desirably is applied at the proximal and distal ends of the transducer (830) around the exposed portions of the inner member (803), wires (836, 837) and stand-off (838) to seal the space between the transducer (830) and the inner member (803) at these locations.

An ultra thin-walled polyester heat shrink tubing (844) or the like then seals the epoxy coated transducer. Alternatively, the epoxy covered transducer (830), inner member (803) and stand-off (838) can be instead inserted into a tight thin wall rubber or plastic tubing made from a material such as Teflon®, polyethylene, polyurethane, silastic or the like. The tubing desirably has a thickness of 0.0005 to 0.003 inches.

When assembling the ablation device assembly, additional epoxy is injected into the tubing after the tubing is placed over the epoxy coated transducer (830). As the tube shrinks, excess epoxy flows out and a thin layer of epoxy remains between the transducer and the heat shrink tubing (844). These layers (842, 844) protect the transducer surface, help acoustically match the transducer (830) to the load, makes the ablation device more robust, and ensures air-tight integrity of the air backing.

Although not illustrated in FIG. 16A in order to simplify the drawing, the tubing (844) extends beyond the ends of transducer (830) and surrounds a portion of the inner member (803) on either side of the transducer (830). A filler (not shown) can also be used to support the ends of the tubing (844). Suitable fillers include flexible materials such as, for example, but without limitation, epoxy, Teflon® tape and the like.

The ultrasonic actuator (840) generates alternating current to power the transducer (830). The ultrasonic actuator (840) drives the transducer (830) at frequencies within the range of about 5 to about 20 MHz, and preferably for the illustrated application within the range of about 7 MHz to about 10 MHz. In addition, the ultrasonic driver can modulate the driving frequencies and/or vary power in order to smooth or unify the produced collimated ultrasonic beam. For instance, the function generator of the ultrasonic actuator (840) can drive the transducer at frequencies within the range of 6.8 MHz and 7.2 MHz by continuously or discretely sweeping between these frequencies.

The ultrasound transducer (830) of the present embodiment sonically couples with the outer skin of the balloon (820) in a manner which forms a circumferential conduction block in a pulmonary vein as follows. Initially, the ultrasound transducer is believed to emit its energy in a circumferential pattern which is highly collimated along the transducer's length relative to its longitudinal axis L (see FIG. 16D). The circumferential band therefore maintains its width and circumferential pattern over an appreciable range of diameters away from the source at the transducer. Also, the balloon is preferably inflated with fluid which is relatively ultrasonically transparent, such as, for example, degassed water. Therefore, by actuating the transducer (830) while the balloon (820) is inflated, the circumferential band of energy is allowed to translate through the inflation fluid and ultimately sonically couple with a circumferential band of balloon skin which circumscribes the balloon (820). Moreover, the circumferential band of balloon skin material may also be further engaged along a circumferential path of tissue which circumscribes the balloon, such as, for example, if the balloon is inflated within and engages a pulmonary vein wall, ostium, or region of atrial wall. Accordingly, where the balloon is constructed of a relatively ultrasonically transparent material, the circumferential band of ultrasound energy is allowed to pass through the balloon skin and into the engaged circumferential path of tissue such that the circumferential path of tissue is ablated.

Further to the transducer-balloon relationship just described, the energy is coupled to the tissue largely via the inflation fluid and balloon skin. It is believed that, for in vivo uses, the efficiency of energy coupling to the tissue, and therefore ablation efficiency, may significantly diminish in circumstances where there is poor contact and conforming interface between the balloon skin and the tissue. Accordingly, it is contemplated that several different balloon types may be provided for ablating different tissue structures so that a particular shape may be chosen for a particular region of tissue to be ablated.

Figure 18A:
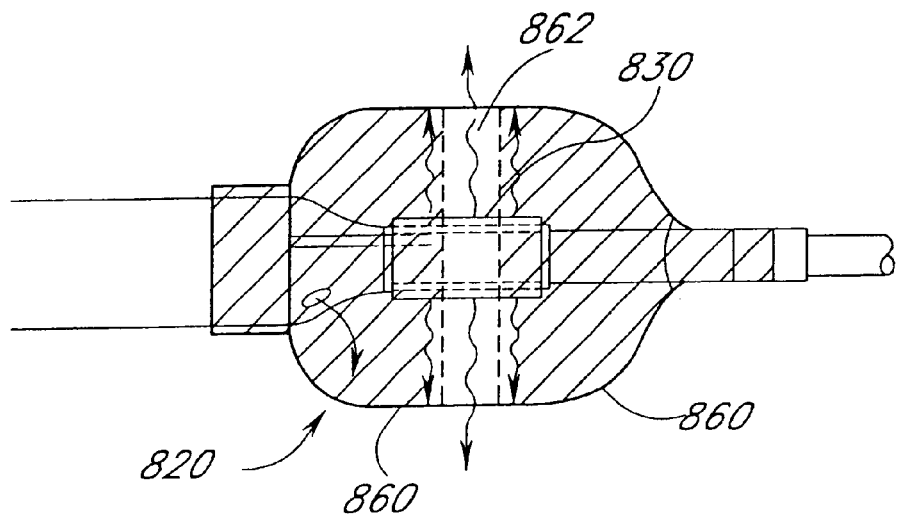
FIG. 18A shows a cross-sectional view of the distal end portion of another circumferential ablation catheter, wherein an outer shield or filter is provided along the balloon's outer surface in order to form a predetermined shape for the circumferential ablation element created by sonic transmissions from the inner ultrasound transducer.

In one particular balloon-transducer combination shown in FIG. 16A and also in FIG. 18A, the ultrasound transducer preferably has a length such that the ultrasonically coupled band of the balloon skin, having a similar length d according to the collimated ultrasound signal, is shorter than the working length D of the balloon. According to this aspect of the relationship, the transducer is adapted as a circumferential ablation member which is coupled to the balloon to form an ablation element along a circumferential band of the balloon, therefore forming a circumferential ablation element band which circumscribes the balloon. Preferably, the transducer has a length which is less than two-thirds the working length of the balloon, and more preferably is less than one-half the working length of the balloon. By sizing the ultrasonic transducer length d smaller than the working length D of the balloon (820)—and hence shorter than a longitudinal length of the engagement area between the balloon (820) and the wall of the body space (e.g., pulmonary vein ostium)—and by generally centering the transducer (830) within the balloon's working length D, the transducer (830) operates in a field isolated from the blood pool. A generally equatorial position of the transducer (830) relative to the ends of the balloon's working length also assists in the isolation of the transducer (830) from the blood pool. It is believed that the transducer placement according to this arrangement may be preventative of thrombus formation which might otherwise occur at a lesion sight, particularly in the left atrium.

The ultrasound transducer described in various levels of detail above has been observed to provide a suitable degree of radiopacity for locating the energy source at a desired location for ablating the conductive block. However, it is further contemplated that the elongate body (802) may include an additional radiopaque marker or markers (not shown) to identify the location of the ultrasonic transducer (830) in order to facilitate placement of the transducer at a selected ablation region of a pulmonary vein via X-ray visualization. The radiopaque marker is opaque under X-ray, and can be constructed, for example, of a radiopaque metal such as gold, platinum, or tungsten, or can comprise a radiopaque plastic (e.g., polymer) such as a metal loaded polymer. The radiopaque marker is positioned coaxially over an inner tubular member (803), in a manner similar to that described in connection with the embodiment of FIG. 13.

The present circumferential ablation device is introduced into a pulmonary vein of the left atrium in a manner similar to that described above. Once properly positioned within the pulmonary vein or vein ostium, the pressurized fluid source inflates the balloon (820) to engage the lumenal surface of the pulmonary vein ostium. Once properly positioned, the ultrasonic driver (840) is energized to drive the transducer (830). It is believed that by driving the ultrasonic transducer 830 at 20 acoustical watts at an operating frequency of 7 megahertz, that a sufficiently sized lesion can be formed circumferentially about the pulmonary vein ostium in a relatively short period of time (e.g., 1 to 2 minutes or less). It is also contemplated that the control level of energy can be delivered, then tested for lesion formation with a test stimulus in the pulmonary vein, either from an electrode provided at the tip area of the ultrasonic catheter or on a separate device such as a guidewire through the ultrasonic catheter. Therefore, the procedure may involve ablation at a first energy level in time, then check for the effective conductive block provided by the resulting lesion, and then subsequent ablations and testing until a complete conductive block is formed. In the alternative, the circumferential ablation device may also include feedback control, for example, if thermocouples are provided at the circumferential element formed along the balloon outer surface. Monitoring temperature at this location provides indicia for the progression of the lesion. This feedback feature may be used in addition to or in the alternative to the multi-step procedure described above.

Figure 17A:
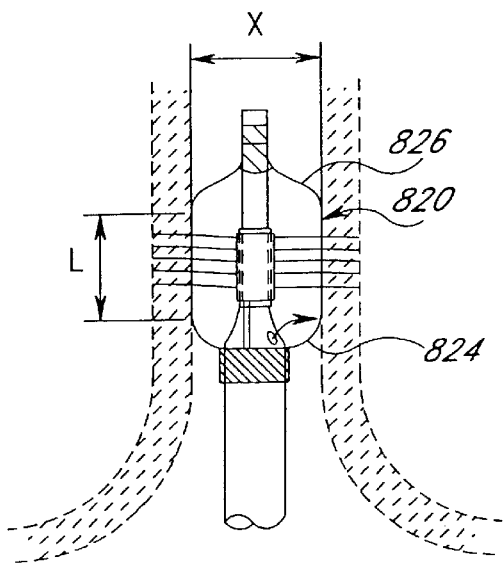
FIG. 17A shows a perspective view of a similar circumferential ablation catheter to the catheter shown in FIG. 16A, and shows the distal end portion of the circumferential ablation catheter during one mode of use in forming a circumferential conduction block in a pulmonary vein in the region of its ostium along a left atrial wall (shown in cross-section in shadow).
Figure 17B:
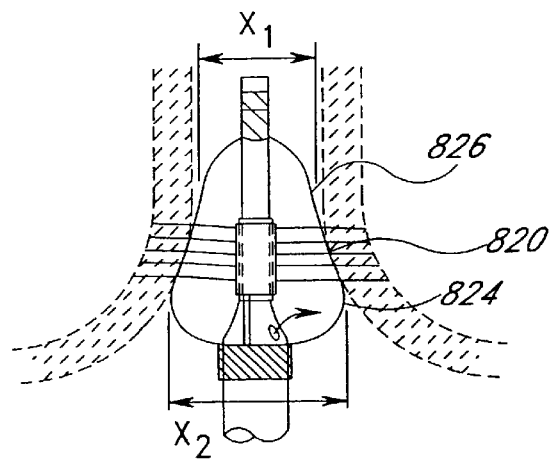
FIG. 17B shows a similar perspective and cross-section shadow view of a circumferential ablation catheter and pulmonary vein ostium as that shown in FIG. 17A, although shows another circumferential ablation catheter wherein the balloon has a tapered outer diameter.
Figure 17C:
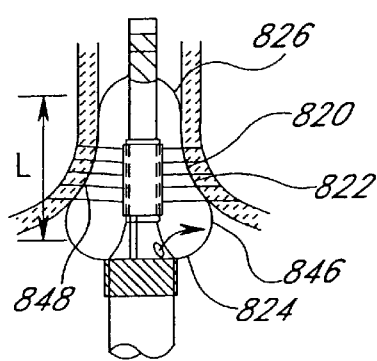
FIG. 17C shows a similar view to that shown in FIGS. 17A–B, although showing another circumferential ablation catheter wherein the balloon has a "pear"-shaped outer diameter with a contoured surface along a taper which is adapted to seat in the ostium of a pulmonary vein.
Figure 17D:
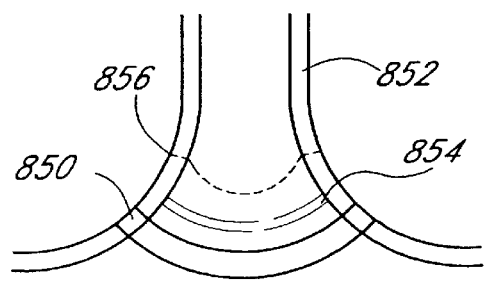
FIG. 17D shows a cross-sectional view of one circumferential conduction block which may be formed by use of a circumferential ablation catheter such as that shown in FIG. 17C.

FIGS. 17A–C show various alternative designs for the purpose of illustrating the relationship between the ultrasound transducer and balloon of the assemblies just described above. More specifically, FIG. 17A shows the balloon (820) having "straight" configuration with a working length L and a relatively constant diameter X between proximal and distal tapers (824, 826). As is shown in FIG. 17A, this variation is believed to be particularly well adapted for use in forming a circumferential conduction block along a circumferential path of tissue which circumscribes and transects a pulmonary vein wall. However, unless the balloon is constructed of a material having a high degree of compliance and conformability, this shape may provide for gaps in contact between the desired circumferential band of tissue and the circumferential band of the balloon skin along the working length of the balloon (820).

The balloon (820) in FIG. 17A is also concentrically positioned relative to the longitudinal axis of the elongate body (802). It is understood, however, that the balloon can be asymmetrically positioned on the elongate body, and that the ablation device can include more than one balloon.

FIG. 17B shows another circumferential ablation device assembly for pulmonary vein isolation, although this assembly includes a balloon (820) which has a tapered outer diameter from a proximal outer diameter $X_2$ to a smaller distal outer diameter $X_1$. (Like reference numerals have been used in each of these embodiments in order to identify generally common elements between the embodiments.) According to this mode, this tapered shape is believed to conform well to other tapering regions of space, and may also be particularly beneficial for use in engaging and ablating circumferential paths of tissue along a pulmonary vein ostium.

FIG. 17C further shows a similar shape for the balloon as that just illustrated by reference to FIG. 17B, except that the FIG. 17C embodiment further includes a balloon (820) and includes a bulbous proximal end (846). In the illustrated embodiment, the proximate bulbous end (846) of the central region (822) gives the balloon (820) a "pear"-shape. More specifically, a contoured surface (848) is positioned along the tapered working length L and between proximal shoulder (824) and the smaller distal shoulder (826) of balloon (820). As is suggested by view of FIG. 17C, this pear shaped embodiment is believed to be beneficial for forming the circumferential conduction block along a circumferential path of atrial wall tissue which surrounds and perhaps includes the pulmonary vein ostium. For example, the device shown in FIG. 17C is believed to be suited to form a similar lesion to that shown at circumferential lesion (850) in FIG. 17D. Circumferential lesion (850) electrically isolates the respective pulmonary vein (852) from a substantial portion of the left atrial wall. The device shown in FIG. 17C is also believed to be suited to form an elongate lesion which extends along a substantial portion of the pulmonary vein ostium (854), e.g., between the proximal edge of the illustrated lesion (850) and the dashed line (856) which schematically marks a distal edge of such an exemplifying elongate lesion (850).

As mentioned above, the transducer (830) can be formed of an array of multiple transducer elements that are arranged in series and coaxial. The transducer can also be formed to have a plurality of longitudinal sectors. These modes of the transducer have particular utility in connection with the tapering balloon designs illustrated in FIGS. 17B and 17C. In these cases, because of the differing distances along the length of the transducer between the transducer and the targeted tissue, it is believed that a non-uniform heating depth could occur if the transducer were driven at a constant power. In order to uniformly heat the targeted tissue along the length of the transducer assembly, more power may therefore be required at the proximal end than at the distal end because power falls off as 1/radius from a source (i.e., from the transducer) in water. Moreover, if the transducer (830) is operating in an attenuating fluid, then the desired power level may need to account for the attenuation caused by the fluid. The region of smaller balloon diameter near the distal end thus requires less transducer power output than the region of larger balloon diameter near the proximal end. Further to this premise, in a more specific embodiment transducer elements or sectors, which are individually powered, can be provided and produce a tapering ultrasound power deposition. That is, the proximal transducer element or sector can be driven at a higher power level than the distal transducer element or sector so as to enhance the uniformity of heating when the transducer lies skewed relative to the target site.

The circumferential ablation device (800) can also include additional mechanisms to control the depth of heating. For instance, the elongate body (802) can include an additional lumen which is arranged on the body so as to circulate the inflation fluid through a closed system. A heat exchanger can remove heat from the inflation fluid and the flow rate through the closed system can be controlled to regulate the temperature of the inflation fluid. The cooled inflation fluid within the balloon (820) can thus act as a heat sink to conduct away some of the heat from the targeted tissue and maintain the tissue below a desired temperature (e.g., 90 decrees C), and thereby increase the depth of heating. That is, by maintaining the temperature of the tissue at the balloon/tissue interface below a desired temperature, more power can be deposited in the tissue for greater penetration. Conversely, the fluid can be allowed to warm. This use of this feature and the temperature of the inflation fluid can be varied from procedure to procedure, as well as during a particular procedure, in order to tailor the degree of ablation to a given application or patient.

The depth of heating can also be controlled by selecting the inflation material to have certain absorption characteristics. For example, by selecting an inflation material with higher absorption than water, less energy will reach the balloon wall, thereby limiting thermal penetration into the tissue. It is believed that the following fluids may be suitable for this application: vegetable oil, silicone oil and the like.

Uniform heating can also be enhanced by rotating the transducer within the balloon. For this purpose, the transducer (830) may be mounted on a torquable member which is movably engaged within a lumen that is formed by the elongate body (802).

Another aspect of the balloon-transducer relationship of the present embodiment is also illustrated by reference to FIGS. 18A–B. In general as to the variations embodied by those figures, the circumferential ultrasound energy signal is modified at the balloon coupling level such that a third order of control is provided for the tissue lesion pattern (the first order of control is the transducer properties affecting signal emission, such as length, width, shape of the transducer crystal; the second order of control for tissue lesion pattern is the balloon shape, per above by reference to FIGS. 17A–C).

More particularly, FIG. 18A shows balloon (820) to include a filter (860) which has a predetermined pattern along the balloon surface and which is adapted to shield tissue from the ultrasound signal, for example, by either absorbing or reflecting the ultrasound signal. In the particular variation shown in FIG. 18A, the filter (860) is patterned so that the energy band which is passed through the balloon wall is substantially more narrow than the band which emits from the transducer (830) internally of the balloon (820). The filter (860) can be constructed, for example, by coating the balloon (820) with an ultrasonically reflective material, such as with a metal, or with an ultrasonically absorbent material, such as with a polyurethane elastomer. Or, the filter (860) can be formed by varying the balloon's wall thickness such that a circumferential band (862), which is narrow in the longitudinal direction as compared to the length of the balloon, is also thinner (in a radial direction) than the surrounding regions, thereby preferentially allowing signals to pass through the band (862). The thicker walls of the balloon (820) on either side of the band (862) inhibit propagation of the ultrasonic energy through the balloon skin at these locations.

Figure 19B:
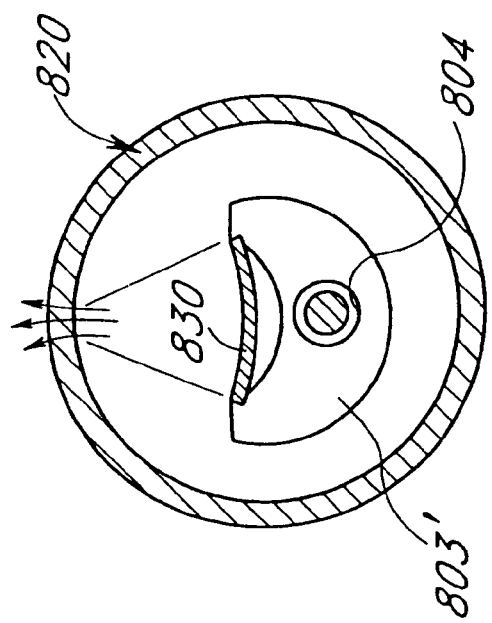
FIG. 19B shows a transverse cross-sectional view of an additional circumferential ablation catheter for pulmonary vein isolation, and shows the ablation element to include a single curvilinear section that is mounted so as to position its concave surface facing in a radially outward direction.
Figure 19A:
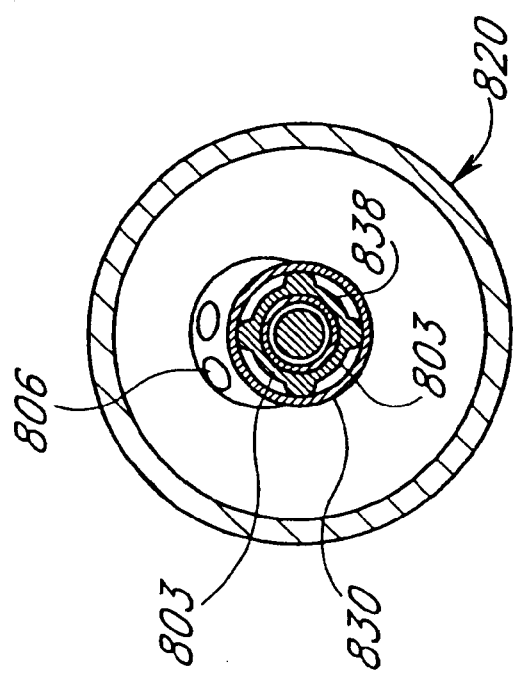
FIG. 19A shows a transverse cross-sectional view of an additional circumferential ablation catheter for pulmonary vein isolation, and shows the ablation element to include a single transducer sector segment which is positioned along an inner member within an expandable balloon which is further shown in a radially expanded condition.

For various reasons, the "narrow pass filter" embodiment of FIG. 19A may be particularly well suited for use in forming circumferential conduction blocks in left atrial wall and pulmonary vein tissues. It is believed that the efficiency of ultrasound transmission from a piezoelectric transducer is limited by the length of the transducer, which limitations are further believed to be a function of the wavelength of the emitted signal. Thus, for some applications a transducer (830) may be required to be longer than the length which is desired for the lesion to be formed. Many procedures intending to form conduction blocks in the left atrium or pulmonary veins, such as, for example, less-invasive "maze"-type procedures, require only enough lesion width to create a functional electrical block and to electrically isolate a tissue region. In addition, limiting the amount of damage formed along an atrial wall, even in a controlled ablation procedure, pervades as a general concern. However, a transducer that is necessary to form that block, or which may be desirable for other reasons, may require a length which is much longer and may create lesions which are much wider than is functionally required for the block. A "narrow pass" filter along the balloon provides one solution to such competing interests.

Figure 18B:
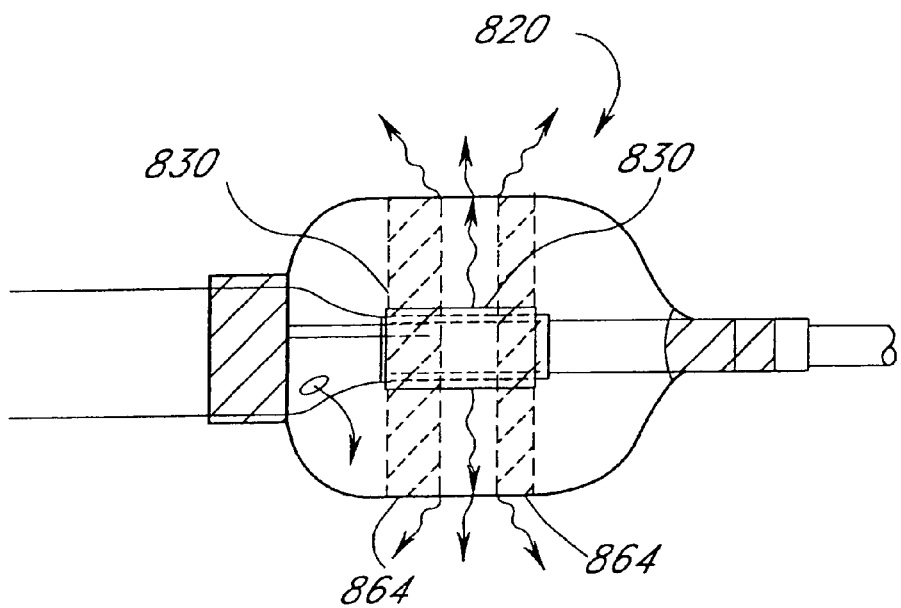
FIG. 18B shows a similar view as that shown in FIG. 18A, although showing the distal end portion of another circumferential ablation catheter which includes a heat sink as an equatorial band within the circumferential path of energy emission from an inner ultrasound transducer.

FIG. 18B shows another variation of the balloon-transducer relationship in an ultrasound ablation assembly. Unlike the variation shown in FIG. 19A, FIG. 18B shows placement of an ultrasonically absorbent band (864) along balloon (820) and directly in the central region of the emitted energy signal from transducer (830). According to this variation, the ultrasonically absorbent band (864) is adapted to heat to a significant temperature rise when sonically coupled to the transducer via the ultrasound signal. It is believed that some ablation methods may benefit from combining ultrasound/thermal conduction modes of ablation in a targeted circumferential band of tissue. In another aspect of this variation, ultrasonically absorbent band (864) may operate as an energy sink as an aid to control the extent of ablation to a less traumatic and invasive level than would be reached by allowing the raw ultrasound energy to couple directly to the tissue. In other words, by heating the absorbent band (864) the signal is diminished to a level that might have a more controlled depth of tissue ablation. Further to this aspect, absorbent band (864) may therefore also have a width which is more commensurate with the length of the transducer, as is shown in an alternative mode in shadow at absorbent band (864).

In each of the embodiments illustrated in FIGS. 16A through 18B, the ultrasonic transducer had an annular shape so as to emit ultrasonic energy around the entire circumference of the balloon. The present circumferential ablation device, however, can emit a collimated beam of ultrasonic energy in a specific angular exposure. For instance, as seen in FIG. 19A, the transducer can be configured to have only a single active sector (e.g., 180° exposure). The transducer can also have a planar shape. By rotating the elongate body (802), the transducer (830) can be swept through 360° in order to form a circumferential ablation. For this purpose, the transducer (830) may be mounted on a torquable member (803), in the manner described above.

FIG. 19B illustrates another type of ultrasonic transducer which can be mounted to a torquable member (803) within the balloon (820). The transducer (830) is formed by curvilinear section and is mounted on the inner member (803) with its concave surface facing in a radially outward direction. The inner member (803) desirably is formed with recess that substantially matches a portion of the concave surface of the transducer (830). The inner member (803) also includes longitudinal ridges on the edges of the recess that support the transducer above the inner member such that an air gap is formed between the transducer and the inner member. In this manner, the transducer is "air-backed." This spaced is sealed and closed in the manner described above in connection with the embodiment of FIGS. 16A–E.

The inverted transducer section produces a highly directional beam pattern. By sweeping the transducer through 360° of rotation, as described above, a circumferential lesion can be formed while using less power than would be required with a planar or tubular transducer.

Further catheter constructions and associated methods of manufacture are provided in accordance with the present disclosure for mounting an ultrasound transducer, as described in FIGS. 16A–E, onto a catheter shaft. Each of the following transducer mounting constructions can be used with overall catheter construction described above. Accordingly, the following descriptions of an isolated ultrasound transducer mounted on an inner section of a catheter shaft will be understood to be in the context of the catheter assembly, including an associated anchoring device (e.g., a balloon), as described above.

Support Structure for Ultrasonic Transducers

In order to minimize the transducer damping associated with the support structure, the mounting arrangements illustrated in FIGS. 20A through 25B support the transducer through attachment to the inner member at locations that are proximal and distal of the ultrasound transducer. These designs also capture air within the mounting structures to air back the transducer. That is, the disclosed modes of suspension illustrated in FIGS. 20A through 25B maintain an air gap. As discussed above, air backing of a cylindrical acoustic transducer is desirable because it provides excellent radial propagation of the ultrasound waves. Conversely, the transducer output is damped whenever it is in contact with any sort of mounting means between the back or inner side of the transducer and the catheter shaft, even highly elastomeric ones. Therefore, the disclosed designs illustrated in these figures are constructed to minimize such damping. To help achieve this efficiency, the air space between the transducer and the inner member is sealed to prevent infiltration by fluids, such as, for example, blood or other fluids. These features are common to the following construction variations.

In each of the variations disclosed below, the transducer is constructed for use in forming a circumferential lesion at a base of or in a pulmonary vein to treat atrial fibrillation as described above. In this application, the transducer preferably is driven in a range of about 6 to about 12 MHz. The transducer for this purpose preferably has a thickness in the range of about 0.009 (0.23 mm) to about 0.013 inches (0.33 mm). A preferred transducer in accordance with the suspended coaxial transducer embodiment may have an inner diameter of 0.070 inch (1.8 mm) and an outer diameter of 0.096 inch (2.4 mm); thus, having a thickness of 0.013 inch (0.3 mm).

While the disclosed catheter assemblies and associated methods of manufacture for constructing a suspended, generally coaxial ultrasonic transducer have applications in connection with forming circumferential lesions as described above, those skilled in the art will appreciate that the present constructions and methods of manufacture also have numerous other applications. For example, the present constructions and methods of manufacture can be used for constructing ultrasonic elements for the delivery into and the ablation of other body spaces in the treatment of other medical conditions, as well as in connection with other applications outside of the medical field.

In another application, the ultrasound ablation device described above and the variations thereof described below may also be used for joining adjacent linear lesions in a less-invasive "maze"-type procedure. In yet another application, the devices may be used within the coronary sinus to ablate the atrioventricular (AV) node to treat Wolff-Parkinson-White syndrome and any other accessory conductive pathway abnormality. In this latter application, it may be desirable to ablate only a portion of the circumference of the coronary sinus, and as such, the ultrasonic ablation devices illustrated in FIGS. 19A and 19B may find particular applicability.

In addition, these types of ablation devices can be mounted onto a pre-shaped catheter shaft that has a curvature that generally matches a natural curvature of the coronary sinus about the exterior of the heart. Such pre-shaped catheter may self-orient within the coronary sinus to position the active ultrasonic transducer toward the inner side of the coronary sinus (i.e., toward the interior of the heart) so as to direct transmission toward the AV node. A catheter constructed with the ultrasonic transducer mounting assemblies disclosed herein can also be designed without an anchoring balloon for use on an end of a flexible catheter for the treatment of ventricular tachycardia.

Figure 20A:
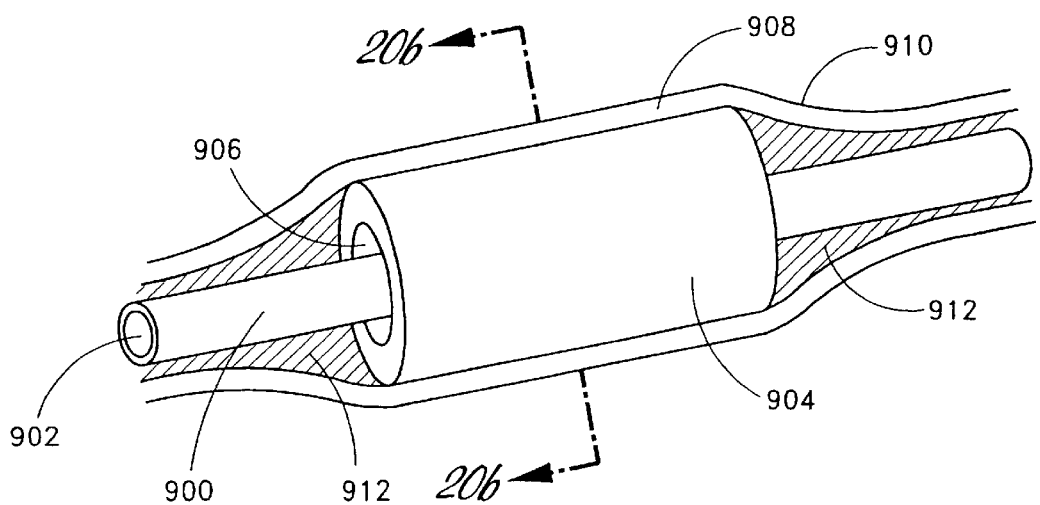
FIG. 20A is a perspective view of one embodiment of the suspended coaxial transducer.
Figure 20B:
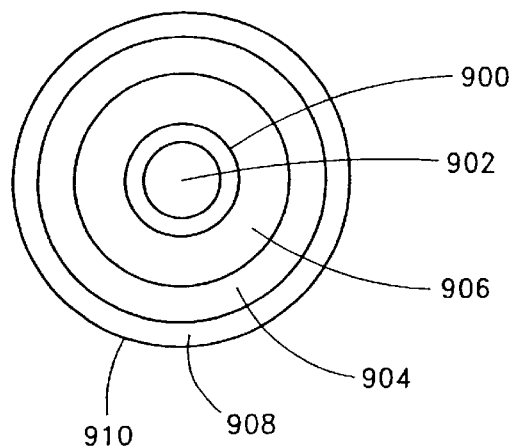
FIG. 20B is a cross-sectional view through the transducer (line B—B).

Referring now to FIGS. 20A and 20B, an external layer coupled to the transducer with a coupling adhesive is described below. By suspending the transducer from such an external protective layer, the problem of maintaining a minimally damped internal mounting scheme is resolved. As illustrated in FIGS. 20A and 20B, a guide member tracking member (900) has a central guide member lumen (902) for slidably engaging and tracking over a guide member (e.g., a guidewire or a steerable catheter). The transducer (904) is generally coaxially disposed over the tracking member (900); however, it is understood that the transducer (904) can be asymmetrically positioned relative to an axis of the guide member tracking member (900) provided an air gap exists between the transducer inner surface and the tracking member (900). An air space (906) exists between the transducer (904) and the tracking member (900), thereby providing an air-backing to maximize the outward radiation of the ultrasonic energy, as described above. It is understood that the transducer need not be mounted on a portion of the catheter that tracks over a guide member, but rather can be mounted on a distal end of a steerable catheter or can be arranged in a side-by-side relationship with such guide member.

The transducer (904) is held suspended over the tracking member (900) by the cooperative arrangement of an outer cover (910), for example, a shrink-wrap polymeric material (e.g., PET), and end plugs (912) bonded to a length of the tracking member (900) proximal and distal to the transducer (904). In the embodiment illustrated in FIGS. 20A and 20B, the end plugs (912) are formed of adhesive and lie under the cover (910), and a layer of adhesive (908) covers the transducer (904) and couples the transducer (904) to an inner surface of the outer cover (910).

The proper air gap may be ensured during setting of the adhesive end plugs (912) by inserting three or more beading mandrels between the tracking member and the transducer. These mandrels would preferably be evenly distributed radially about the tracking member (900) and would run axially along the length of the transducer (910). The beading mandrels can be sized so as to create a desired air gap (e.g., 0.005 inches (0.13 mm)). Since the mandrels must be removed, it is preferred that the beading mandrels be made out of a material to which the epoxy adhesive will not stick, such as for example, metal or silicone, and extend beyond one end of the transducer (904) during the assembly process. FIG. 20B is a cross-sectional view through the transducer along line B—B of FIG. 20A. The thickness of the adhesive layer can be in the range of about 0.0005 (0.013 mm) to about 0.001 inches (0.025 mm). The cover can have a thickness in the range of about 0.001 to about 0.003 inches.

Figure 21A:
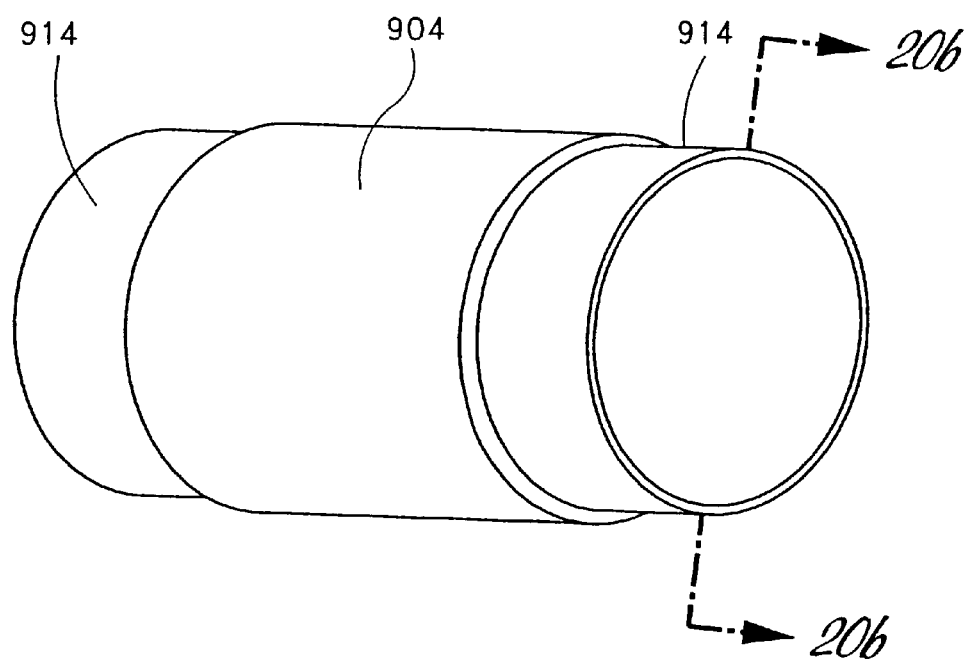
FIG. 21A is a perspective view showing another embodiment of the suspended coaxial transducer having a thin molded shell.
Figure 216:
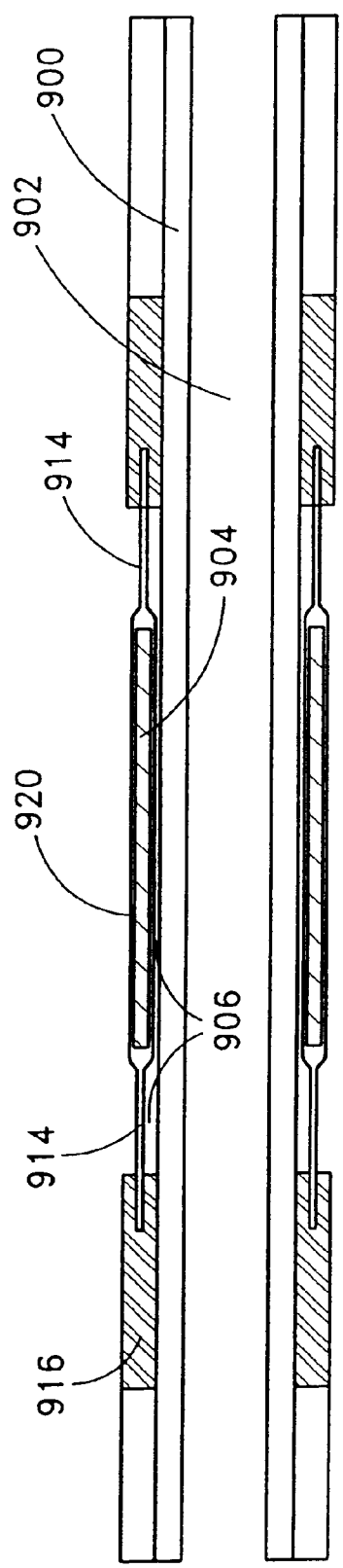

FIGS. 21A and 21B illustrate another embodiment of the suspended coaxial transducer of the present invention. With reference to FIG. 21A, the transducer (904) is shown in perspective view formed inside an enclosure such as a thin shell or housing, which has mounting flanges (914) extending proximally and distally from the transducer. FIG. 21B shows the transducer in transverse section. The transducer (904) is suspended over the tracking member (900) by the mounting flanges (914) which extend from either end of the transducer (904). An air space (906) exists between the inner surface of the housing (920) that encapsulates the transducer (904) and the tracking member (900). The air space (906) extends to and may be more pronounced in the regions between the mounting flanges (914) and the tracking member (900), depending on the configuration of the mounting flanges.

The mounting flanges (914) may be formed in a variety of configurations, as long as they extend axially from the transducer and are capable of mounting to the tracking member (900) so as to suspend the transducer over the tracking member (900). For example, the flanges (914) may be centrally disposed and of a smaller outer diameter than the coated transducer, as illustrated in FIGS. 21A and 21B. Alternatively, the flanges may be of the same diameters or may have a larger inner diameter than the coated transducer. The flanges may also be disposed asymmetrically, for instance, extending from the top or bottom surfaces of the transducer. With respect to the method of constructing such support assemblies as herein shown and described by reference to the specific embodiments, the shapes provided may be imparted onto a starting "plug" or workpiece of material, such as by grinding or heat processing, or the support may be molded, laminated, cast, or otherwise formed as a "composite" of sorts wherein each region of the support is a subassembly that is connected to the others to form the support structure.

The mounting flanges (914) may also be mounted in a variety of structures (916) attached to the delivery member (900) on the proximal and distal sides of the transducer. One variation in the mounting structure (916) can be an end cap with a groove sized to receive the mounting flange, as shown in FIG. 21B. Such end cap can be made of a suitable plastic or elastomer (e.g., silicone, PET, etc.). Another variation of the mounting design is illustrated in FIG. 22, which shows a support sleeve and shrink-wrap cover. In this variation, the transducer (904) with molded coating (920) and flanges (914) is suspended over the tracking member (900) by a support sleeve (928) upon which the flanges (914) rest. The support sleeve (928) may have a groove for engaging the flange as shown. The transducer (904) can be secured by heat shrinking a covering sleeve (926) (e.g., PET) over the flanges (914), thereby maintaining the air gap (906) between the transducer (904) and the tracking member (900)—such resulting construction also beneficially provides a seal to prevent fluid from infiltrating into the airspace under the transducer. The mechanical joints formed by compressing the ends of the mounting flanges between the support sleeve (928) and the covering sleeve (926) supports the ends of the mounting flanges (914) with the transducer suspended between the resulting proximal and distal joints.

Figure 23:
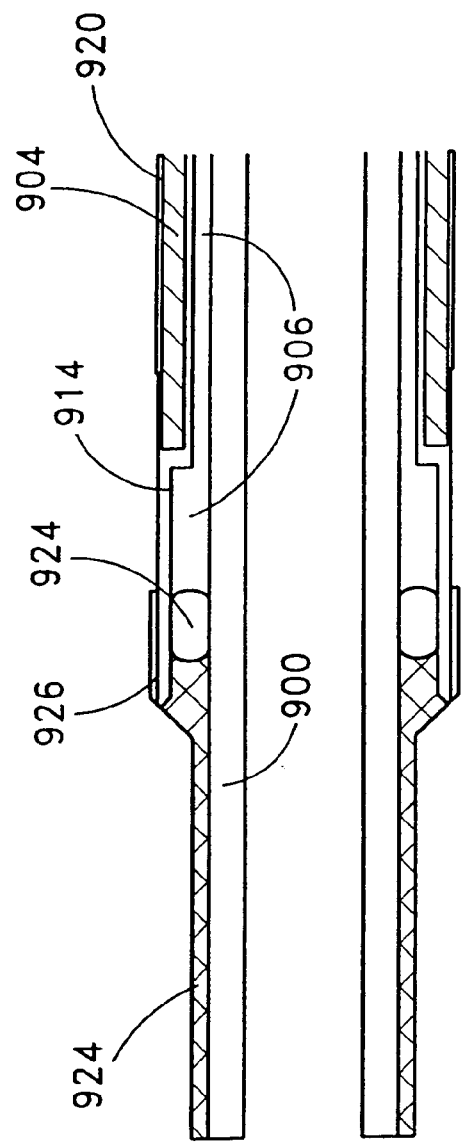
FIG. 23 shows another variation of the design for mounting the molded transducer having an O-ring and shrink-wrap cover.

In accordance with another variation, as illustrated in FIG. 23, the mounting structure can include O-rings (922), upon which the flanges (914) rest, thereby suspending the transducer (904) above the tracking member (900), wherein the proximal flange is bonded with adhesive (924), preferably a flexible adhesive, to the tracking member proximal to the proximal O-ring and the distal flange is bonded with adhesive to the tracking member distal to the distal O-ring. Moreover, the transducer/housing assembly and flanges thus mounted by adhesive may be further secured by heat shrinking a plastic (e.g., polymeric) covering sleeve (926) over the flange (914). The shrink-wrap cover could be fused to the elastomeric adhesive (924) by heat or chemical process. In a variation, the entire suspended coaxial transducer assembly, including the flanges (914) could be covered with the shrink-wrap material (926) that is also bound by the adhesive. The assembly can also be dipped coated to form the outer covering.

The O-ring mounting variation has the advantage of preventing adhesive from running into the air gap, for example, when the assembly is heated in applying the shrink-wrap. Also, the elastic properties of the O-ring tend to push the flange tightly against the shrink-wrap outer cover. The O-rings also support the transducer about the tracking member during the assembly process (e.g., when applying the epoxy and heat shrinking) to hold the transducer in a generally concentric position relative to an axis of the tracking member (900) before the assembly cures.

The thin molded shell (920) that coats the transducer (904) and forms the flanges (914) is preferably made of a high temperature resistant elastomer, an in any event a material that may withstand temperatures up to about 200° C. in the event the transducer is run at high power, such as at a power sufficient to ablate circumferential regions of tissue. The material may be a thermoset elastomer, such as urethane or silicone rubber. Alternatively, the material could be a thermoplastic polymer, such as polyurethane, PET, or any other polymeric thermoplastic known to those of skill in the art for manufacture of medical devices. The shell should have a Shore hardness of about 90 (scale A). However, the greater the unsupported distance along the flange between the mounting structure (e.g., the end cap, support sleeve or O-ring) and the transducer, the greater the flexibility of the flange. While high flexibility of the flanges is desirable for damping prevention, the stiffness of the flange material must nevertheless be sufficient to prevent the suspended transducer from bowing and contacting the tracking member. The stiffness can be increased by using a material of higher Shore hardness (e.g., a thermoplastic rather than silicone rubber) and/or by increasing the thickness of the flange.

Several methods of manufacturing the transducer with a thin coating of plastic or rubber (e.g., silicone or other elastomeric coatings) and axial flanges are disclosed herein. First, the housing could be injection molded about the transducer. The injection molding could be accomplished in at least two separate stages. Using silicone as an exemplifying material, a base layer of silicone is placed beneath the transducer and axially to form the flanges, while the transducer is mounted on a base sleeve of silicone on a mandrel. When cured, the mandrel is removed, leaving the transducer coated on its upper surface with the silicone support cover the inner surfaces of the transducer. The outer coating and the inner sleeve of silicone desirably are joined, either by a fusion of the materials during the injection process or by heat or chemical processes, or by other means well known in the art. If an inner support is not used, the bottom surfaces next can be injection molded in similar manner. The two half molds can then be joined by heat or chemical process to form the complete shell. Instead of injection molding the second surface of the transducer, the half-coated transducer could be formed by dipping in a liquid elastomer, one or several times. Since the flange would be difficult to form by dipping, it would be preferred that the flange be injection molded. Alternatively, it may be desirable to use a transducer coated only on one surface (e.g., the inner surface). Lastly, the transducer coated with a thin shell may be made by dipping the transducer one or several times to achieve the desired thickness. A mandrel may be used to hold the transducer during the dipping process.

Figure 24:
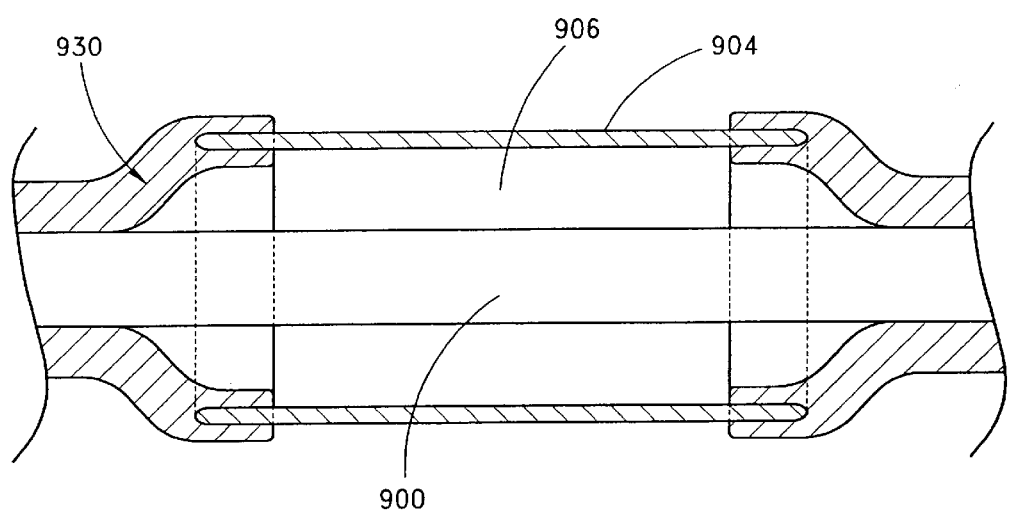
FIG. 24 shows another variation of the suspended coaxial transducer having preformed end mounts.

Another variation of the suspended coaxial transducer (904) is illustrated in FIG. 24 having injection molded end mounts (930). In this variation, the transducer is suspended over the tracking member (900) by fitting within grooves formed in injection molded end mounts (930). The grooves may be molded or formed during post-molding processing. The end mounts are molded to have an inside diameter of close to that of the outside diameter of the tracking member (900) so as to facilitate fastening to the tracking member (900) by adhesive or other means proximal and distal to the transducer. The end mounts also have an increased diameter in the mounting region, so as to engage the transducer within the mounting grooves at a fixed distance above the tracking member (900), thereby creating the desired air gap (906). The transducer may be secured within the end mount grooves by adhesive, fasteners, etc.

Figure 25A:
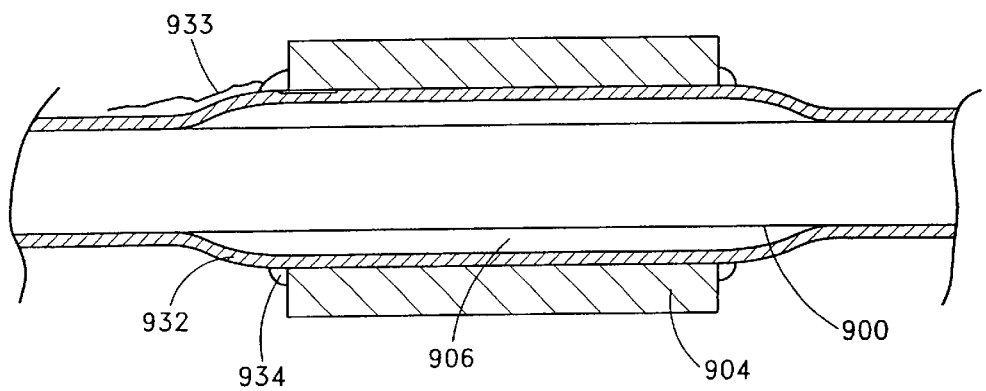
FIG. 25A shows a mounting balloon variation of the suspended coaxial transducer.

A mounting balloon variation of the suspended coaxial transducer is shown in FIG. 25A. In this variation, the transducer (904) is mounted on an expandable member or balloon (932) that creates a flexible mounting structure and an air gap (906) between the balloon (932) and the outer surface of the tracking member (900). The transducer (904) can be sealed to the balloon by elastomeric adhesive. In this variation, the electrical lead (933) to the inner conductive layer of the ultrasound transducer may be sealed using elastomeric adhesive between the balloon (932) and the inner layer of the transducer (904). In another variation, the adhesive can be conductive (e.g., contain silver) and a surface of the balloon can be coated with or formed by a conductive layer so as to provide an electrical path from a lead in contact with or embedded within the adhesive, through the conductive layer an to an inner electrode of the transducer to power the inner electrode.

Figure 25B:
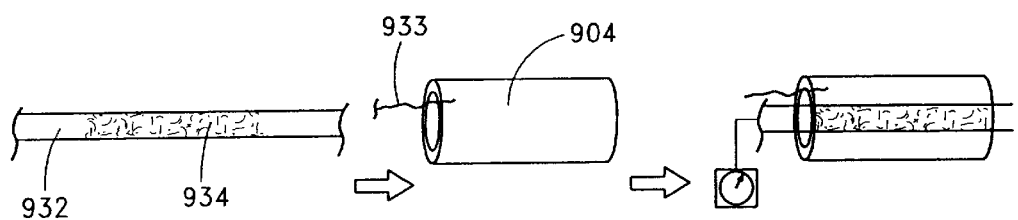
FIG. 25B is a perspective view of the sequence of making the balloon mounted transducer shown in FIG. 25A.

With reference to FIG. 25B, there is shown a perspective view of one possible sequence of making the balloon mounted transducer. On the left side, a tubular balloon stock (932) is shown before inflation, having a layer of adhesive (934) applied to the outer surface. In the center, the transducer (904) is shown with the inner lead (933) in place. Next, the transducer (904) is inserted over the balloon (932). The distal region of the balloon is then closed and pressurized air or fluid is applied at the proximal end causing the balloon to inflate and press radially outward against the inner surface of the transducer. During this process, the balloon may be "cold blown" without the presence of heat as known in the art, or can be heated. In this latter process, the balloon is inflated while heating the balloon material to a glass transition temperature within a "capture tube." The capture tube desirably has a diameter generally equal to an inner diameter of the transducer so that the formed balloon will have an outer diameter approximating the inner diameter of the transducer. In addition, the capture tube can be configured so as to produce a desired profile for neck sections of the balloon on either side of a central section on which the transducer will be mounted. In either a cold or heated process, the balloon is inflated to a size causing the adhesive to bond the interior surface of transducer against an exterior section of the balloon.

The adhesive bonds the outer surface of the balloon to the inner surface of the transducer; the bonding step may require heating. In heating process, the adhesive desirably can withstand the blowing temperatures, as one skilled in the art will readily appreciate. The inner lead is thereby fixed in contact with the inner surface of the transducer and exits through the adhesive seal between the balloon and the transducer.

The mounting construction illustrated in FIG. 25A can also be made by performing the balloon (either by a cold or heated blowing process) and subsequently placing the transducer over the inflated section of the balloon. Adhesive is placed between the balloon and the transducer, either by precoating the balloon and/or transducer with adhesive, or by injecting adhesive between the balloon and the transducer. The preformed balloon may dip coated with an elastomer (e.g., silicone).

When assembled, the transducer can be cover by an outer jacketing or cover, but need not be. Such coating or jacket can be formed in any of a variety of ways, including, for example, but without limitation, by a dipping process or by heat-shrinking a cover over the transducer and balloon assembly. The coating or jacket inhibits fluid within the anchoring balloon (822) (FIG. 16A) from seeping between the mounting balloon (932) and the transducer (904).

The mounting balloon (932) can have a fairly rigid structure and generally maintain its shape after the blowing process, or can collapse down after blowing. When assembled to the tracking member (900) (e.g., the catheter shaft) the collapse balloon is inflated and pressurized to assume its shape. A static air lock is formed by sealing the ends of the mounting balloon in a well known manner.

The mounting balloon, as apparent from the above description, can be formed of any of a variety of materials used to form catheter balloon, including those that are compliant and those that are non-compliant. For instance, a mounting balloon that holds its shape can be made of a relatively rigid plastic (e.g., a polymer) such as a polyethylene ("PE"; preferably linear low density or high density or blends thereof), polyolefin copolymer ("POC"), polyethylene terepthalate ("PET"), polyimide, PEBAX or a nylon material. A balloon assembled with a static air lock can be made of any of a variety of compliant and non-compliant materials, such as any of those identified herein.

While the above mounting constructions have been illustrated with reference to a cylindrical transducer, it is understood that these mounting constructions can be used with arcuate or flat transducer panels. Additionally, the transducer or transducer assembly (when formed by a plurality of transducer panels) need not extend entirely about the tracking member. In such a case, as noted above, the catheter may be rotated through an arc or completely rotated, depending upon the application, to create the desired lesion pattern.

FIG. 26 illustrates another mounting arrangement for the ultrasound transducer (904) on the tracking member (900). This variation, however, does not suspend the transducer (904) from supports that attached to the tracking member on proximal and distal sides of the transducer. Rather, the mounting arrangement includes an elastomeric support (940) that in interposed between the ends of the transducer (904) and the tracking member (900).

As seen in FIG. 26, as well as in FIGS. 27, 28A and 28B, the support (940) has a generally tubular configuration. The support (940) includes thick walled end portions (942) and a thin walled central portion (944). The inner diameter of the support (940) generally matches the outer diameter of the tracking member (900), and the outer diameter of the end portions (942) generally matches the inner diameter of the transducer (904). The outer diameter of the central portion (944) is smaller than the outer diameter of the end portions (942) thereby creating an air gap between the transducer (904) and the central portion (944). When assembled, the transducer is attached to the end portions (942) of the support (940) by a suitable adhesive or epoxy.

FIGS. 29A–29D illustrate a future design according to the invention wherein a cylindrical ultrasound transducer (1000) is mounted onto shaft (1052) of a delivery member (1050) via support member (1020). The support member (1020) has two end regions (1022,1024) and an intermediate region (1026) therebetween. The transducer (1000) coaxially surrounds and rests on the intermediate region (1026), whereas the end regions (1022,1024) function as flanges by mounting onto the underlying shaft (1052) without bridging across the radial separation area (1010) between the outer surface (1055) of the shaft (1052) and the inner surface (1006) of transducer (1000). In addition, each of the end regions (1022,1024) includes an outer lip (1023,1025), respectively, which border the ends (1002,1004) of the transducer (1000), also respectively, and provide in one regard for the longitudinal stability of the transducer position on the shaft (1052). In one further mode illustrated in FIG. 29D, outer jackets (1030,1040) can be secured over the end regions (1022,1024) and onto the shaft (1052) such as via adhesive fillets (1036,1046) and thereby effectively seal the radial separation area (1010) from fluid ingress without covering the transducer (1000). The end regions (1022,1024) of the support member (1020) also include inner lips (1023',1025') which rest on the outer surface (1055) of the shaft (1052) outside of the radial separation area (1010) and provide the "stand-offs" to ensure airbacking along radial separation area (1010).

As elsewhere disclosed herein, the support member (1020) preferably is constructed of an elastomeric or at least flexible material in order to decrease damping, and is also preferably relatively heat resistant and non-degradable at temperatures around about 200° C. In addition, dimensions for the various features of the support member (1020) include: outer diameter of surface (1055) of the shaft (1052) of around about 0.050 inches; inner diameter of the intermediate region (1026) of around about 0.060 inches; and inner diameter of the transducer (1000) of around about 0.070 inches.

Figure 30A:
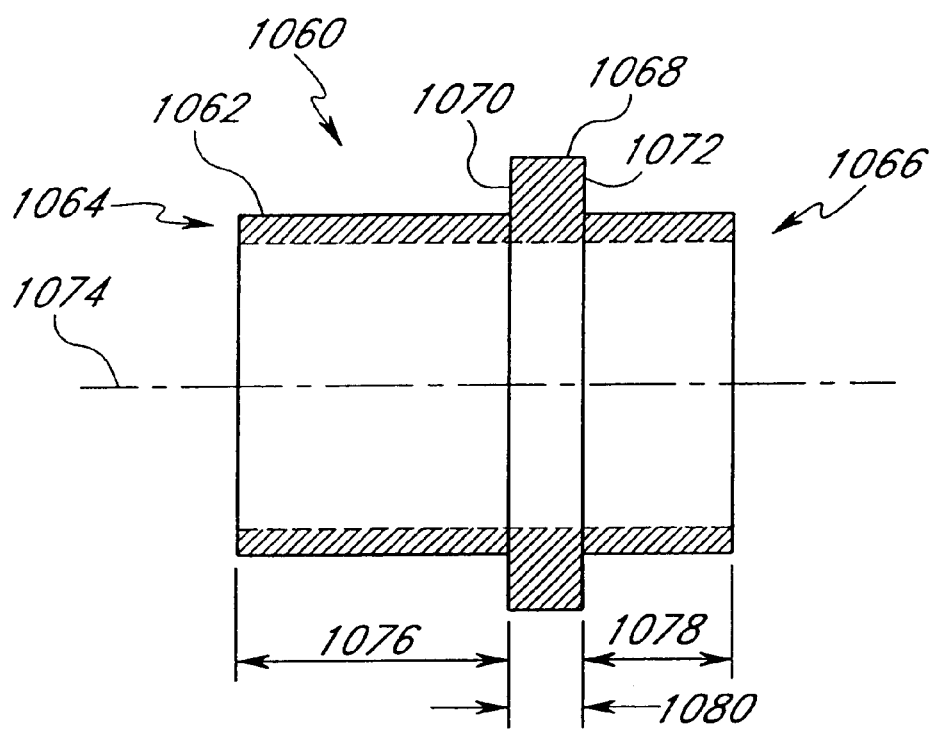
FIG. 30A is a longitudinal cross-sectional view of a modification of the support illustrated in FIG. 27.
Figure 30B:
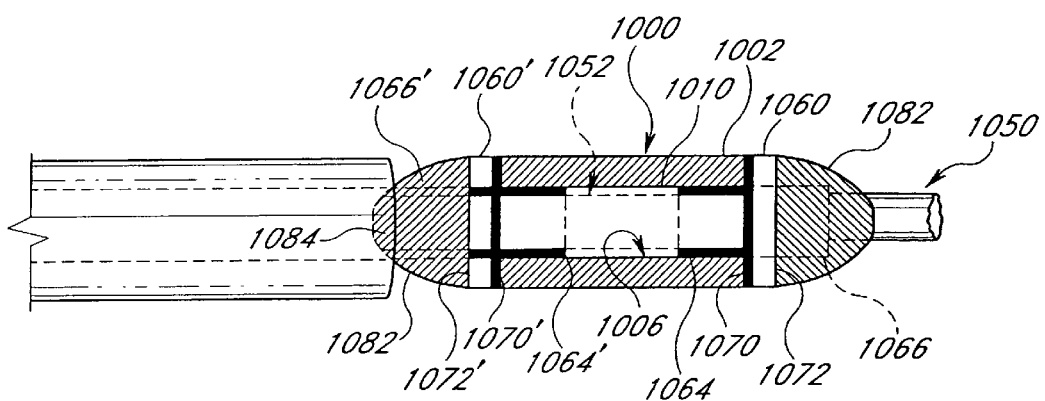
FIG. 30B is a longitudinal cross-sectional view of two of the support members illustrated in FIG. 30A supporting a transducer on a tracking member of a catheter assembly.

FIGS. 30A and 30B illustrate a modification wherein a support member (1060) is formed from a body (1062) having a first end (1064), a second end (1066), and a raised portion (1068) disposed between the first and second ends (1064,1066). As shown in FIG. 30A, the raised portion (1068) extends annularly around the body (1062) and forms a first end annular face (1070) and a second annular face (1072). The first and second annular faces (1070,1072) face towards the first end (1064) and the second end (1066), respectively. The body (1062) is preferably annular in shape and defines a longitudinal axis (1074). Also, preferably, the annular faces (1070,1072) extend approximately normally to the axis (1074). Preferably, the body (1062) is made from a rigid material such as polyimide. However, it is conceived that the body (1062) can be formed of any rigid material, including metals such as platinum, stainless steel, nitenol, or other rigid plastics.

Still referring to FIG. 30A, the body (1062) extends over a length (1076) between the raised portion (1068) and the first end (1064). Additionally, the body (1062) extends over a length (1078) between the raised portion (1068) and the second end (1066). The length (1078) is less than the distance (1076). Additionally, the raised portion (1068) has a thickness (1080).

With reference to FIG. 30B, the transducer (1000), constructed in accordance with the description of the transducer (1000) disclosed above with reference to FIGS. 29A–29D, is supported over the shaft (1052) of the delivery member (1050) by two support members (1060,1060'). The first ends (1064, 1064') of the support members (1060,1060'), respectively, are arranged so as to support the inner surface (1006) of the transducer (1000). As such, the portions of the body (1062) having the length (1067) are positioned within the transducer (1000) and the portions of the body (1062) having the shorter length (1078) extend away from the transducer (1000) and the annular faces (1072,1072'), respectively.

The support members (1060,1060') are preferably bonded to the transducer (1000) with EP42ET. The EP42ET adhesive is spread so as to form a bond between the first ends (1064,1064') and the annular faces (1070,1070'), and the transducer (1000). The second ends (1066,1066') are preferably bonded to the shaft (1052) with loctite 498 (1082). The loctite (1082) is applied in the form of a fillet to substantially cover the annular faces (1072,1072') and the ends (1066,1066') of the support members (1060,1060'), respectively. Additionally, the adhesive (1072) is preferably spread to form a fluid-tight seal between the second ends (1066,1066') and the shaft (1052).

In the illustrated embodiment, a notch (not shown) is formed in the support member (1060') and an electric lead wire (1084) extends through the notch and is connected to the inner surface (1006) of the transducer (1000). As noted above, the inner surface (1006) of the transducer (1000) defines one of the electrodes of the transducer (1000). Thus, the electric lead wire (1084) is connected to the inner surface (1006) for powering the transducer (1000). Similarly, a further electric lead wire (not shown) is attached to the outer surface (1002) of the transducer (1000) for powering the transducer (1000).

As shown in FIG. 30B, the inner ends (1064,1064') of the support members (1060,1060') are spaced from each other such that the radial separation area (1010) is maintained between the inner surface (1006) of the transistor (1000) and the shaft (1052). In the illustrated embodiment, the bond between the support members (1060,1060') and the transducer (1000) is maintained in a fluid-tight state by the EP42ET adhesive. Additionally, the loctite 498 (1082) maintains a fluid-tight seal between the support members (1060, 1060') and the shaft (1052).

Referring again to FIG. 30A, an illustrative example of the support members (1060,1060') is dimensioned as follows. An inner diameter of the body (1062) is 0.058"±0.001". An outer diameter of the body (1062) is 0.067"±0.001". The length (1080) of the raised portion (1068) is approximately 0.015"±0.001". The length (1078) of the body (1062) between the raised portion (1068) and the second end (1066) is preferably 0.030"±0.002".

The outer diameter of the raised portion (1068) is preferably 0.090"±0.002". The overall length of the support member (1060), i.e., the sum of the lengths (1076,1080, 1078) is preferably 0.095"±0.002". The above-noted dimensions for the support members (1060,1060') are sized for a shaft, such as such the shaft (1062) illustrated in FIG. 30B having an outer diameter of approximately 0.057".

It will be understood that the above-noted dimensions are merely exemplifying of one preferred form. The dimensions each depend upon one another, upon the density and shape of the support members, transducer, and the shaft, and the desired normal operating conditions. It is understood that one of skill in the art can vary the dimensions to adapt the catheter for a particular application through routine experimentation, in view of this disclosure herein.

With reference to FIG. 30B, the outer surface (1002) of the transducer (1000) is preferably left exposed. Thus, when the illustrated transducer (1000) is provided within an expandable balloon (not shown) and a fluid such as saline, or the like, as noted above, is supplied to the interior of the balloon so as to inflate the balloon for use in a tissue ablation procedure, the outer surface (1002) of the transducer (1000) is exposed to the fluid. As noted above, the transducer (1000) preferably is a piezoelectric ultrasonic transducer having one electrode on its inner surface (1006) and another electrode on its outer surface (1002).

It has been found that by leaving at least a portion of the outer surface (1002) exposed to the fluid, reflected ultrasonic energy is greatly lowered during the operation of the transducer (1000). Additionally, since there is less material applied to the outer surface (1002) of the transducer (1000), the delamination of such outer coating is attenuated, thus, enhancing the useful life of the catheter.

Figure 31A:
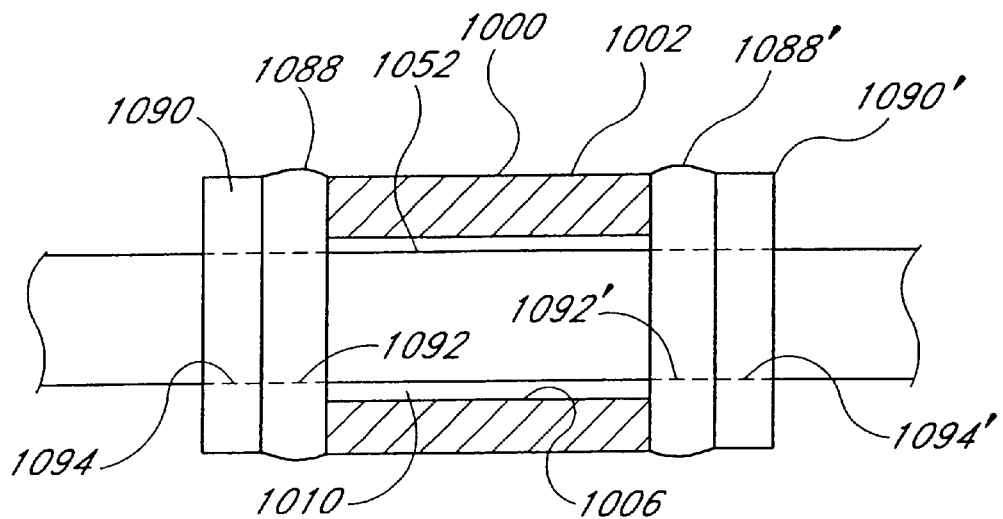
FIG. 31A is a partial longitudinal sectional view of a modification of the transducer and support shown in FIG. 30B.

FIG. 31A illustrates a further modification of the catheter illustrated in FIGS. 29A–29D. As shown in FIG. 31A, the transducer 1000 is sealed at its proximal and distal ends by elastic washers (1088, 1088'). Additionally, pressure washers (1090, 1090') are provided on the outer sides of the elastic washers (1088, 1088'), respectively.

As shown in FIG. 31A, the transducer (1000) includes an outer surface (1002) and an inner surface (1006). The transducer (1000) is suspended by the elastic washers (1088, 1088') so as to maintain the radial separation (1010) between the inner surface (1006) and the shaft (1052).

The elastic washers (1088, 1088') are preferably formed by annular members composed of any appropriate elastic material including, for example, silicone, rubber, or the like. As shown in FIG. 31A, the elastic washers (1088, 1088') include through holes (1092) defining an inner diameter which provides a close fit to the shaft (1052).

The pressure washers (1090, 1090') are preferably formed from a more rigid material, such as, for example, but without limitation, metals such as platinum, stainless steel, PET, and polyimide. Similarly to the elastic washers (1088, 1088'), the pressure washers (1090, 1090') include through holes (1094, 1094') which have an inner diameter sized to form a close fit with the shaft (1052). Preferably, during assembly, the pressure washers (1090, 1090') are pressed against the elastic washers (1088, 1088') so as to form a fluid-tight seal against the ends of the transducer (1000). With the pressure washers (1090, 1090') pressed against the elastic washers (1088, 1088'), the pressure washers (1090, 1090') are then secured to the shaft (1052) so as to maintain the elastic washers (1088, 1088') in fluid-tight contact with the transducer (1000).

Optionally, the elastic washers (1088, 1088') can also be bonded to the proximal and distal ends of the transducer (1000). The outer sides of the elastic washers (1088, 1088') are likewise bonded to the pressure washers (1090, 1090') with a suitable adhesive. Finally, an additional adhesive or sealant is provided at the interface between the through holes (1094, 1094'), and the shaft (1052). As such, the radial separation (1010) is maintained and is sealed to prevent fluid from infiltrating into the separation (1010). As noted above, with reference to FIG. 30, the outer surface (1002) of the transducer (1000) illustrated in FIG. 31A is preferably left exposed to a fluid used during an ablation process.

Figure 31B:
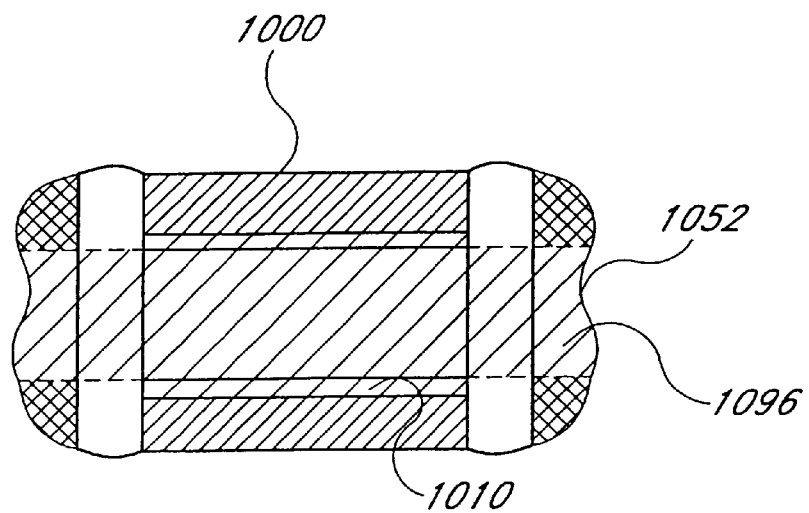
FIG. 31B is a longitudinal sectional view of a modification of the embodiment shown in FIG. 31A.

FIG. 31B illustrates a modification of the catheter shown in FIG. 31A. As shown in FIG. 31B, a splined support member (1096) supports the transducer (1000) relative to the shaft (1052) so as to maintain the air gap (1010) between the transducer (1000) and the shaft (1052). The splined support member (1096) can be constructed in accordance with the disclosure of the stand-off (838) set forth above with reference to FIGS. 16A–16D. Sealing washers (1098, 1098') are placed in sealing engagement with the ends of the transducer (1000). In the illustrated embodiment, adhesive (1099) replaces the pressure washers (1090, 1090') illustrated in FIG. 31A.

Figure 29A:
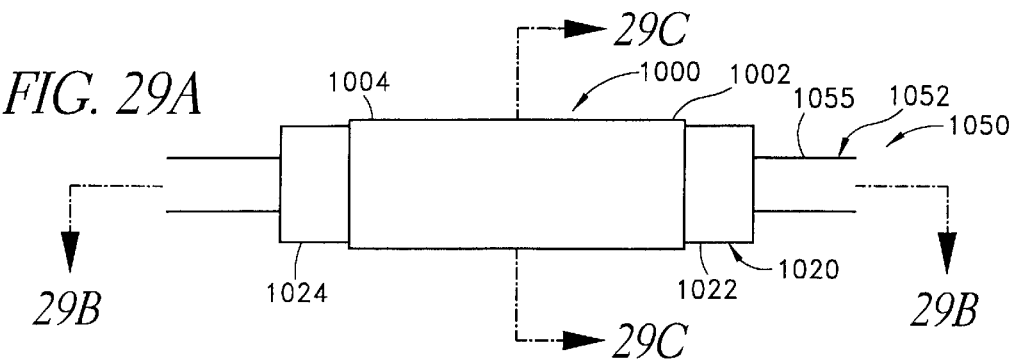
FIG. 29A shows a perspective view of another transducer mounted onto a tracking member of a catheter assembly according to the invention.
Figure 29D:
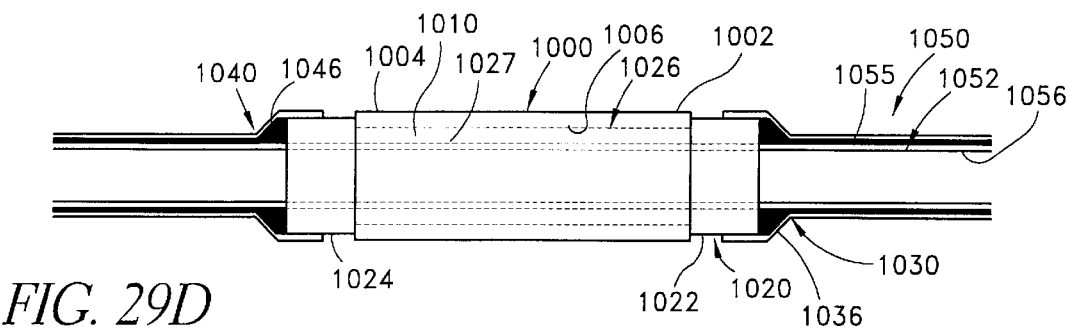
FIG. 29D shows a longitudinal cross-sectional view of a transducer mounted onto a tracking member of a catheter assembly according to an embodiment of the present invention.
Figure 29C:
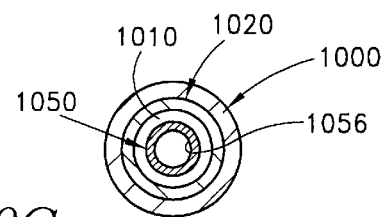
FIG. 29C shows a transverse cross-sectional view taken along lines 29C—29C in FIG. 29A.
Figure 29B:
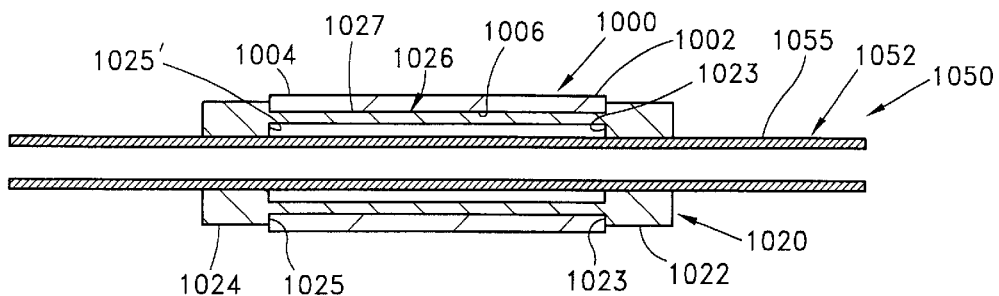
FIG. 29B shows a longitudinal cross-sectional view taken along lines 29B—29B in FIG. 29A.
Figure 32A:
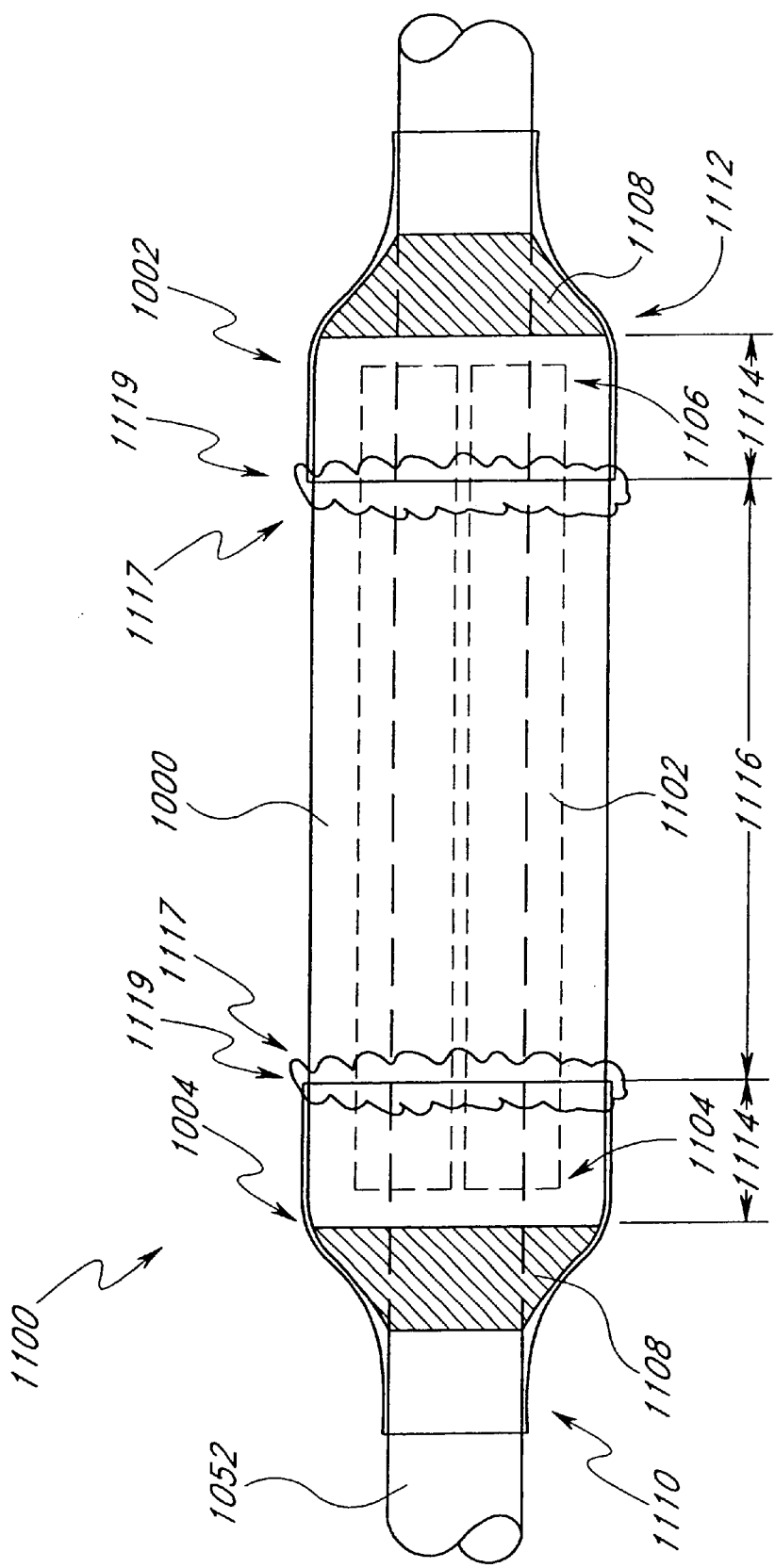
FIG. 32A is an elevational view of a modification of the ablation catheter illustrated in FIG. 16, having a splined support (shown in phantom) supporting a transducer relative to an inner member and having jackets covering the proximal and distal ends of the transducer.

FIG. 32A illustrates a further modification of the transducer assembly illustrated in FIGS. 29A–29B. As shown in FIG. 32A, the transducer assembly (1100) includes the transducer (1000) mounted onto the shaft (1052) via a splined support member (1102). The support member (1102) is preferably in the form of an elastic or an elastomeric material, such as silicone, and includes a plurality of splines extending longitudinally along the support member (1102). The construction of the splines included on the support (1102) can be in accordance with the construction of the splines (839) included on the standoff (838) illustrated in FIG. 16C. Thus, a further description of the splined support member (1102) is not necessary for one of ordinary skill in the art to practice the invention as disclosed herein.

Figure 32B:
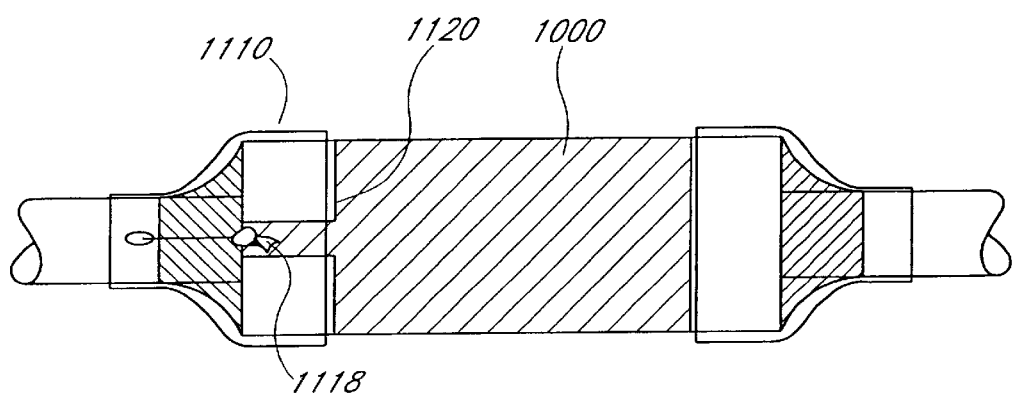
FIG. 32B is a partial longitudinal sectional view of the catheter shown in FIG. 32A.

As shown in FIG. 32B, support member (1102) is positioned such that the proximal and distal ends (1104, 1106) of the support (1102) terminate within the transducer (1000). The proximal and distal ends (1004, 1002) of the transducer (1000) are sealed to the shaft (1052) with a fillet of silicone or epoxy adhesive (1108). Additionally, jackets (1110, 1112) are formed over the fillets (1108).

As shown in FIG. 32A, the jackets (1110, 1112) extend completely over the fillets (1108) and overlap portions of the proximal and distal ends (1004, 1002) of the transducer (1000). In the illustrated embodiment, the jackets (1110, 1112) are formed from a rigid material such as PET. In the illustrated embodiment, the jackets (1110, 1112) overlap the proximal and distal ends (1004, 1002) of the transducer (1000) over a distance (1114) of approximately ½ to 1 mm. Additionally, the jackets (1110, 1112) are sized so as to leave at least a portion of the outer surface of the transducer (1000) exposed. In the illustrated embodiment, since the transducer (1000) is approximately 6 to 7 mm, the exposed portion of the transducer (1000) extends over a length (1116) of approximately 5 millimeters. Additionally, in the illustrated embodiment, the jackets (1110, 1112) are formed from a layer of PET having a thickness of approximately 0.001 inches to 0.0005 inches. As shown in FIG. 32A, epoxy fillets (1117) are preferably provided at the interface between the inner ends (1119) and the outer surface of the transducer (1000). As such, the fillets (1117) provide further anchoring effect of the jackets (1110, 1112) to the outer surface of the transducer (1000).

It will be understood that the above-noted dimensions are merely exemplifying of one preferred form. The dimensions each depend upon one another, as well as other characteristics. It is understood that one of ordinary skill in the art can readily vary the dimensions to adapt the catheter for a particular application through routine experimentation, in view of the disclosure herein.

With reference to FIG. 32B, an electric lead wire (1118) can be connected to the outer surface of the catheter (1000). As shown in FIG. 32B, a notch (1120) is formed in the jacket (1110) so as to allow the lead wire (1118) to be electrically connected to the outer surface of the transducer (1000).

Figure 33A:
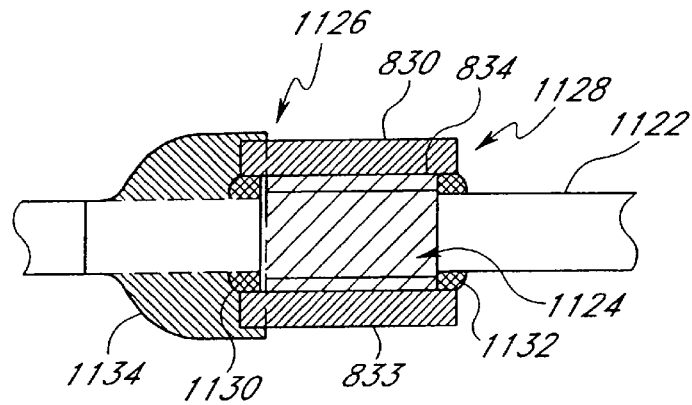
FIG. 33A is a partial longitudinal sectional view of a modification of the catheter shown in FIG. 32A having a splined support supporting a transducer relative to an inner member.

FIG. 33A illustrates a further modification of the circumferential ablation device assembly (800) illustrated in FIGS. 16A–16D. As shown in FIG. 33, the circumferential ultrasound transducer (830) is supported coaxially about an inner member (1122) and is supported about the inner member (1122) in a manner providing a gap between the inner member (1122) and the transducer inner tubular member (834). In the illustrated embodiment, a splined support member (1124) is disposed between the inner tubular member (834) and the inner member (1122) to maintain the air gap therebetween.

The splined support member (1124) can be constructed in accordance with the description of the standoff (838) having splines (839) set forth above with reference to FIG. 16C. Thus, a further description of the splined support member (1124) is not necessary for one of ordinary skill in the art to practice the invention as disclosed herein.

Similarly to the standoff (838) disclosed above with reference to FIG. 16C, the splined support member (1124) includes a plurality of circumferentially spaced outer splines so as to maintain a gap between the inner member (1122) and the inner tubular member (834). Additionally, in the illustrated embodiment, the proximal end (1126) and the distal end (1128) of the transducer (830) are sealed to the inner member (1122) with fillets of adhesive. Preferably, the fillets (1130, 1132) are formed of a silicone adhesive. However, it is apparent to one of ordinary skill in the art that the adhesive may be any of a variety of adhesives.

As shown in FIG. 33A, an outer jacket (1134) is secured over the proximal end (1126) and the sealing bead (1130) and onto the inner member (1122) thereby further sealing the space between the inner tube (834) and the inner member (1122) from the ingress of fluid. In the illustrated embodiment, the jacket (1134) is in the form of a shrink-wrapped layer of PET. However, it is apparent to one of ordinary skill in the art that the jacket (1134) can be constructed in accordance with any of the jackets disclosed above. A distal end jacket (1136) can similarly be provided on the distal end (1128) of the transducer (830) (FIG. 33B).

Figure 33B:
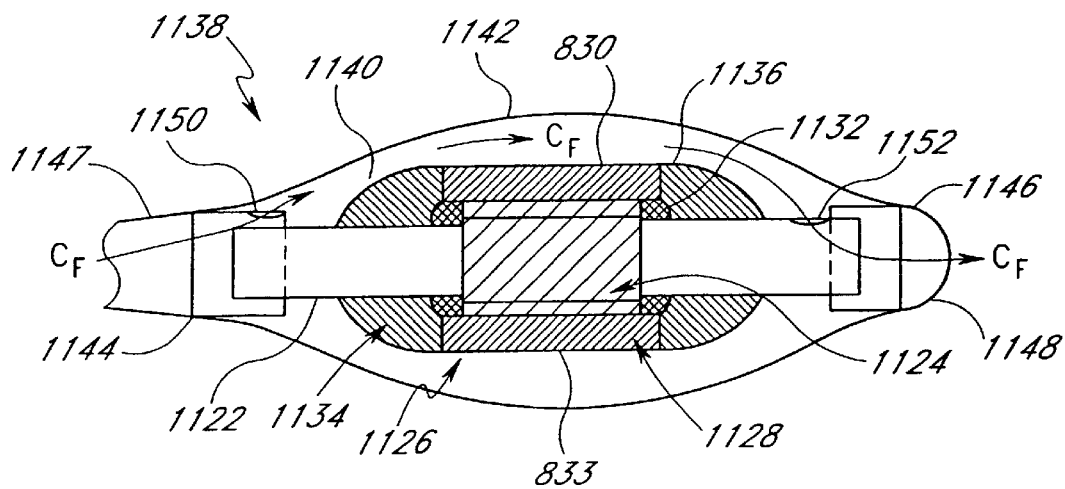
FIG. 33B is a partial longitudinal sectional view of the catheter shown in FIG. 33A illustrating a cooling assembly installed to the catheter shown in FIG. 33A.

With reference to FIG. 33B, a cooling system (1138) can be incorporated with the transducer assembly illustrated in FIG. 33A. As shown in FIG. 33B, the cooling system (1138) includes a cooling chamber (1140) defined by an outer wall (1142). In the illustrated embodiment, the outer wall (1142) is formed of a balloon or bag that extends over the distal and proximal ends (1126, 1128) of the transducer (830).

As shown in FIG. 33B, the wall (1142) includes a proximal neck portion (1144) and a distal neck portion (1146). Additionally, the inner member (1122) extends from an elongate body (1147). The elongate body (1147) can be constructed in accordance with the elongate body (802) illustrated in FIG. 16A. The proximal neck portion (1144) of the wall (1142) is sealed to the elongate body (1147). Additionally, the distal neck portion (1146) is sealed to a distal guidewire port (1148). The distal guidewire port (1148) can be constructed in accordance with the distal guidewire port (805) disclosed above with reference to FIG. 16A.

As shown in FIG. 33B, the elongate body (1147) includes a fluid discharge (1150) positioned distally from the proximate neck portion (1144). Additionally, the inner member (1122) includes a distal port (1152) arranged distally from the transducer (830), but proximally from the distal neck portion (1146).

In operation, when the transducer (830) is driven by a power source, such as the power source (840) disclosed above with reference to FIG. 16B, a coolant can be supplied through a coolant lumen extending through the elongate body (1147) so as to flow into the cooling chamber (1140) through the proximal coolant port (1150), around the transducer (830) and into the distal coolant port (1152). For example, as shown in FIG. 33B, coolant flows, indicated generally by the arrows CF can enter the cooling chamber (1140), contact the transducer (830) and flow out of the cooling chamber (1140), thereby cooling the transducer (830). In the illustrated embodiment, the outer electrode (833) is at least partially exposed to the coolant flows $C_F$. Thus, the thermal conduction of heat from the transducer (830) to the coolant flow $C_F$ is enhanced.

After the coolant flow $C_F$ enters the distal coolant port (1152), the coolant flow can be directed through the guidewire lumen (not shown) and into the patient's body. Alternatively, the coolant flow can be returned to the proximate end of the elongate body (1147) through a coolant return lumen (not shown).

Figure 33C:
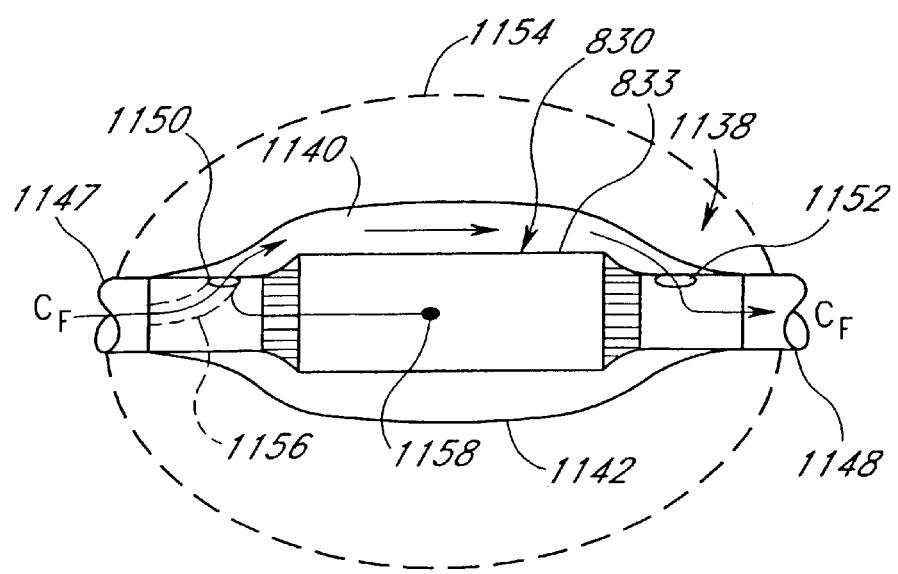
FIG. 33C is a schematic view of the catheter cooling assembly illustrated in FIG. 33B disposed within an expandable ablation balloon (shown in phantom).

With reference to FIG. 33C, the cooling assembly (1138) is illustrated as being provided within an expandable balloon (1154). The expandable balloon (1154) can be constructed in accordance with the disclosure of the expandable balloon (820) set forth above with reference to FIGS. 16A and 16C. Thus, a further description of the expandable balloon (1154) is not necessary for one of ordinary skill in the art to practice the invention as disclosed herein.

Although separate lumens can be provided for supplying coolant fluid to the coolant chamber (1140) and for returning coolant fluid to the proximal end of the elongate body (1147), in the illustrated example, coolant fluid is supplied to the coolant chamber (1140) via a thermocouple lumen (1156). As shown in FIG. 33C, a thermocouple (1158) is placed in operative contact with the outer surface (833) of the transducer (830) so as to provide temperature data for controlling the output of the transducer (830).

In the illustrated embodiment, the cooling chamber wall (1142) is formed of a PET bag having an inner diameter of 0.110 inches and a thickness of 0.0005 inches. However, it is apparent to one of ordinary skill in the art that these dimensions can be varied according to the desired characteristics of the cooling chamber (1140).

Figure 34A:
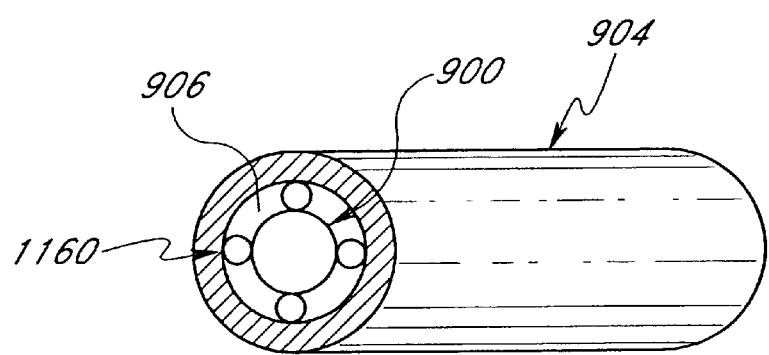
FIG. 34A is a modification of the catheter shown in FIG. 32A having a plurality of mandrels arranged between an inner member and a transducer of a catheter so as to maintain a gap between the inner surface of the transducer and an outer surface of the inner member.
Figure 34B:
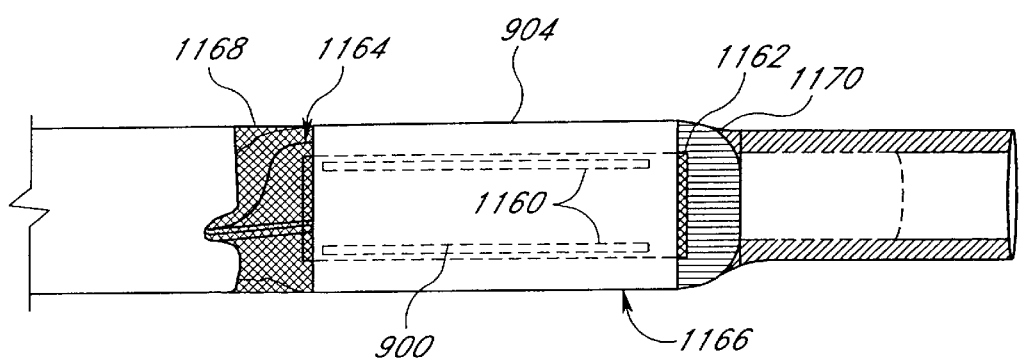
FIG. 34B is a partial longitudinal sectional view of the catheter shown in FIG. 34A with lead wires connected to the electrodes of the transducer.

FIGS. 34A and 34B illustrate a modification of the embodiment of FIGS. 20A and 20B. As noted above with respect to FIGS. 20A and 20B, a plurality of mandrels can be inserted between the transducer (904) and the tracking member (900). With the mandrels arranged around the tracking member (900), a desired air gap can be defined between the transducer (904) and the tracking member (900). The transducer (904) is then bonded to the tracking member (900) with an adhesive that will not stick to the material used to form the mandrels. After the transducer (904) has been bonded to the tracking guide member (900), the mandrels are removed and the transducer (904) is then sealed to the tracking member (900) with the cover (910).

In the modification illustrated in FIG. 34A, a plurality of mandrels (1160) are arranged between the tracking member (900) and in inner surface of the transducer (904). The mandrels (1160) are sized and spaced so as to generate a substantially uniform air space (906) between the transducer (904) and the tracking member (900).

As shown in FIG. 34B, the mandrels (1160) are preferably sized to be slightly shorter than the transducer (904). With the mandrels arranged between the transducer (904) and the tracking member (900), the air space is sealed with an adhesive such as loctite 498 (1162). In the illustrated embodiment, a silicone seal seals the proximal and distal ends (1164, 1166) of the transducer (904) against the tracking member (900). Additionally, a loctite fillet (1168, 1170) is formed over the silicone (1162, 1164).

In the illustrated embodiment, the tracking member (900) is formed of a polyimide tube having an outer diameter of approximately 0.048 inches and the mandrels (1160) are formed of polyimide rods or tubes having an outer diameter of approximately 0.008 inches. However, it is apparent to one of ordinary skill in the art that the above-noted dimensions can be varied according to the desired characteristics and overall dimensions of the catheter.

Figure 35:
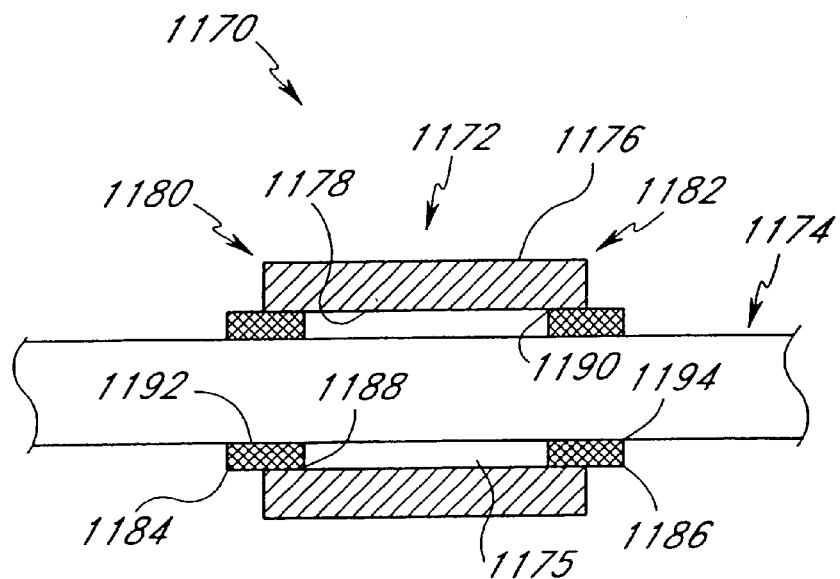
FIG. 35 is a longitudinal sectional view of another circumferential ablation catheter, and shows the ablation element to include a single cylindrical ultrasound transducer which is positioned along an inner member and is connected to the inner member via a pair of end mounts, one end mount being provided at each of the proximal and distal ends of the transducer.

FIG. 35 illustrates a further modification of the embodiment illustrated in FIG. 26. As shown in FIG. 35, a transducer assembly (1170) includes a transducer (1172) mounted to an inner member (1174). The construction of the transducer (1172) can be in accordance with the disclosure of the transducer (830) disclosed above with reference to FIGS. 16A–16B. Thus, a further description of the transducer (1172) is not believed to be necessary for one of ordinary skill in the art to practice the invention as disclosed herein.

In the illustrated embodiment, the transducer (1172) has an outer electrode (1176) and an inner electrode (1178). The transducer (1172) is supported relative to the inner member (1174) so as to maintain an air gap (1175) therebetween. Additionally, the transducer (1172) includes a proximal end (1180) and a distal end (1182). The construction of the inner member (1174) can be in accordance with the description of the construction of the inner member (803)—disclosed above with reference to FIGS. 16A–16E. Thus, a further description of the inner member (1174) is not believed to be necessary for one of ordinary skill in the art to practice the invention as disclosed herein.

As shown in FIG. 35, the transducer (1172) is supported relative to the inner member (1174) by first and second end mounts (1184, 1186). The end mounts (1184, 1186) include at least a first metal surface portion (1188, 1190), respectively. The metal surface portions (1188, 1190) are welded to the inner electrode (1178). Thus, a metal-to-metal connection is formed between the end mount (1184) and the proximal end (1180) of the transducer (1172) and between the distal end (1182) and the metal surface portion (1190) of the second end mount (1186). The metal-to-metal contact between the inner electrode (1178) and the metal surface portions (1188, 1190) can be formed through any conventional methods for welding, soldering, or the like.

The end mounts (1184, 1186) also include an inner surface (1192, 1194), respectively. The inner surfaces (1192, 1194) are preferably sized to provide a close fit with an outer surface of the inner member (1174). The inner surfaces (1192, 1194) are bonded to the inner member (1174) with any appropriate adhesive or sealing substances. For example, the inner surfaces (1192, 1194) can be bonded to the inner member (1174) with silicone, loctite, epoxy, or any of a variety of adhesives.

In the illustrated embodiment, the end mounts (1184, 1186) are in the form of metal bands. The bands can be formed out of any of a variety of metals including, but without limitation, stainless steel and platinum. However, as will be apparent from the description set forth below, the end mounts (1184, 1186) are not required to be solid metal. Rather, the end mounts (1184, 1186) may be formed from any material having a metalized surface portion.

By mounting the transducer (1172) to the inner member (1174) with a plurality of end mounts which have at least a metal surface portion, e.g., (1188, 1190), the present transducer assembly (1170) will benefit from the high strength and highly temperature resistant metal-to-metal bonds created between the metal surface portions (1188, 1190) and the inner electrode (1178). Additionally, because the seal between the end mounts (1184, 1186) and the inner member (1174) are separated from the transducer (1172), such seals are more protected from heat generated by the transducer (1172). Thus, the present transducer assembly (1170) provides for enhanced life span and reliability of the seals provided at the proximal and distal ends (1180, 1182) of the transducer (1172).

Figure 36:
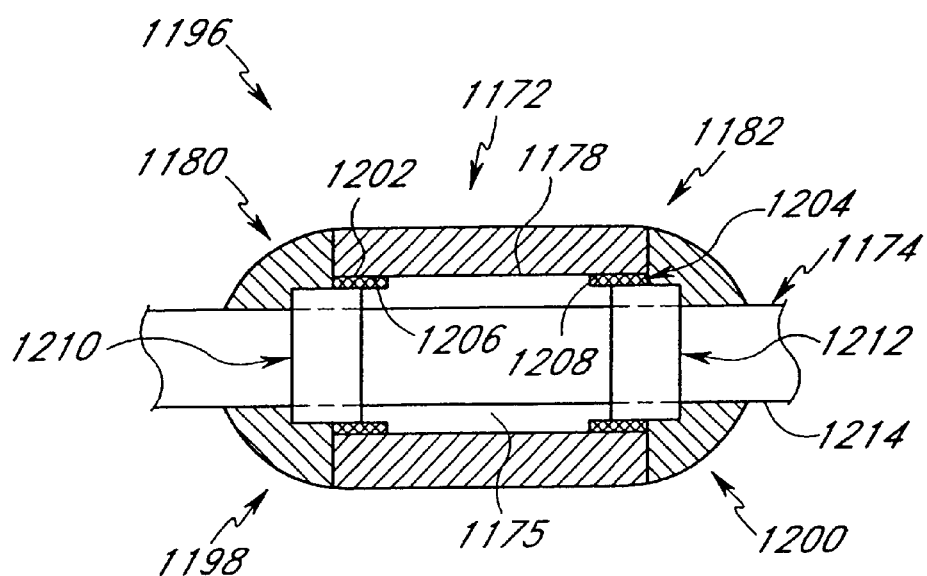
FIG. 36 is a longitudinal sectional view of a modification of the catheter illustrated in FIG. 35 showing the transducer being supported by a pair of end mounts which are, in turn, supported by a pair of raised portions of a flexible material bonded to the inner member.

FIG. 36 illustrates a modification of the transducer mounting assembly (1170) illustrated in FIG. 35. In accordance with the present modification, a transducer assembly (1196) includes the transducer (1172) supported relative to the inner member (1174) by first and second end mounts (1198,1200). In the illustrated embodiment, the end mounts (1198,1200) are formed of band members (1202,1204), each of which have a metal surface portion (1206,1208) connected to the inner electrode (1178). In the illustrated embodiment, the band members (1202,1204) are supported by raised portions (1210,1212) provided on the inner member (1174).

In the illustrated embodiment, the raised portions (1210, 1212) have an annular shape and are formed of a flexible material. Optionally, the raised portions (1210,1212) can be formed integrally with a layer of silicone (1214) formed around the inner member (1174). The proximal and distal ends (1180,1182) of the transducer (1172) and the outer ends of the band members (1202,1204) are sealed with the raised portion (1210,1212) with epoxy fillets.

As noted above with respect to the embodiment illustrated in FIG. 35, by welding or soldering, the inner electrode (1178) to the metal surface portions (1206,1208) of the band members (1202,1204), the present modification benefits from the metal-to-metal seal provided between the metal surface portions (1206,1208) and the inner electrode (1178). Additionally, since the seal between the band members (1202,1204) and the raised portions (1210,1212) are spaced from the transducer (1172), the seal therebetween is protected from heat generated by the transducer (1172) and thus suffers less deterioration caused by heat generated by the transducer (1172).

Figure 37A:
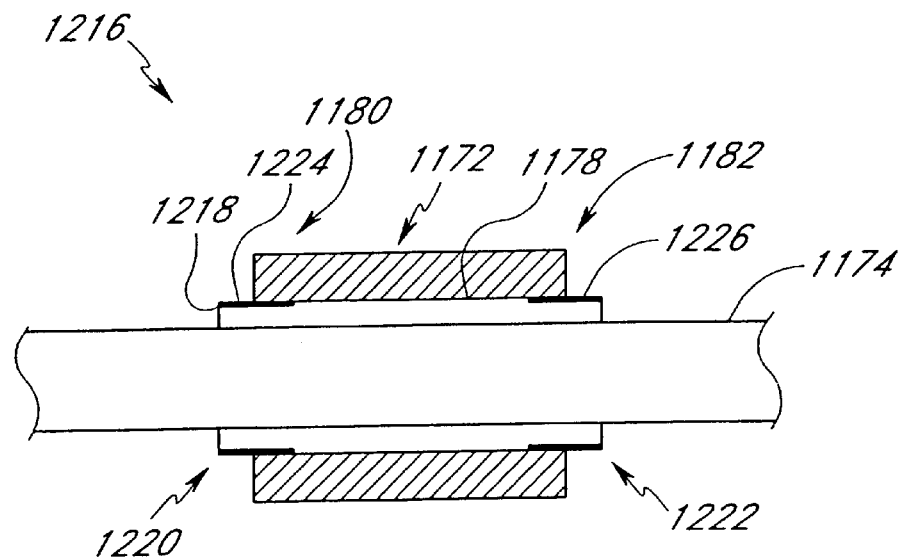
FIG. 37A is a partial longitudinal sectional view of a further circumferential ablation catheter, and shows the ablation element to include a single cylindrical ultrasound transducer which is positioned along an inner member and connected to the inner member via a support which includes metal surface portions in contact with the proximal and distal ends of the transducer.

FIG. 37A illustrates a further modification of the embodiment illustrated in FIG. 35. As shown in FIG. 37A, a transducer assembly (1216) includes the transducer (1172) mounted to the inner member (1174). An annular support member (1218) is provided between the inner electrode (1178) and the outer surface of the inner member (1174). In the present modification, the spacer member (1218) is a tubular-shaped member formed of a rigid material such as, for example, but without limitation, polyimide.

At proximal and distal ends (1220,1222) of the support member (1218), metal surface portions (1224,1226) are provided on an outer surface of the support member (1218). The metal surface portions (1224,1226) are welded or soldered to the inner electrode (1178). Additionally, loctite and/or silicone fillets can be provided over the proximal and distal ends (1180,1182) of the transducer (1172) as well as the proximal and distal end (1220,1222) of the support member (1218), although such fillets are not shown.

In the illustrated embodiment, the inner electrode (1178) is welded or soldered to the metal surface portions (1224, 1226) only at the proximal and distal ends (1180,1182) of the transducer (1172). The remaining outer surface portions of the support member (1218) and the inner electrode (1178) are not connected. Thus, although the support member (1218) has a substantially uniform thickness over its entire length, the transducer assembly (1216) remains substantially air backed.

As noted above with respect to the transducer assembly (1170) illustrated in FIG. 35, the seal between the support member (1218) and the inner member (1174) is spaced from the transducer (1172), and thus is protected from the damaging effects of heat generated by the transducer (1172).

Figure 37B:
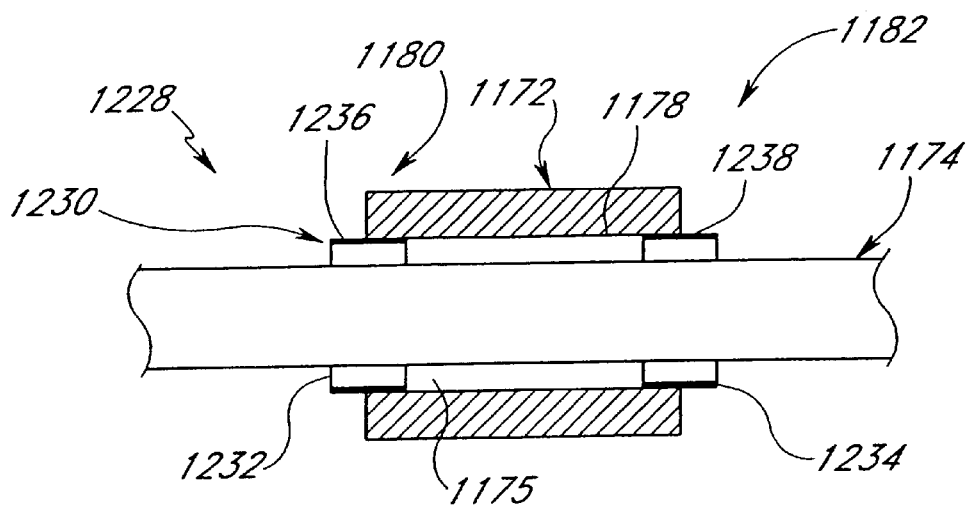
FIG. 37B is a modification of the catheter shown in FIG. 37A, the support being formed in two separate pieces.

FIG. 37B illustrates a further modification of the embodiment illustrated in FIG. 37A. As shown in FIG. 37B, a transducer assembly (1228) includes the transducer (1172) supported relative to the inner member (1174) by support assembly (1230). In the illustrated embodiment, the support assembly (1230) is comprised of a pair of individual bands similar to the construction of the end mounts (1184,1186) illustrated in FIG. 35.

In the present modification, the support assembly (1230) is formed of a pair of plastic bands (1232,1234) having an outer metal surface portion (1236,1238). In the illustrated embodiment, the plastic bands (1232,1234) are formed of polyimide. The outer metal surface portions (1236,1238) can be formed of any number of metals, for example, but without limitation, platinum, stainless steel, and nitenol. The inner electrode (1178) can be fixed to the metal surface portions (1236,1238) in accordance with the description set forth above with respect to FIG. 35. Additionally, the proximal and distal ends (1180,1182) of the transducer and bands (1232,1234) can be sealed with adhesives such as silicone, loctite, or other similar adhesives.

Figure 38A:
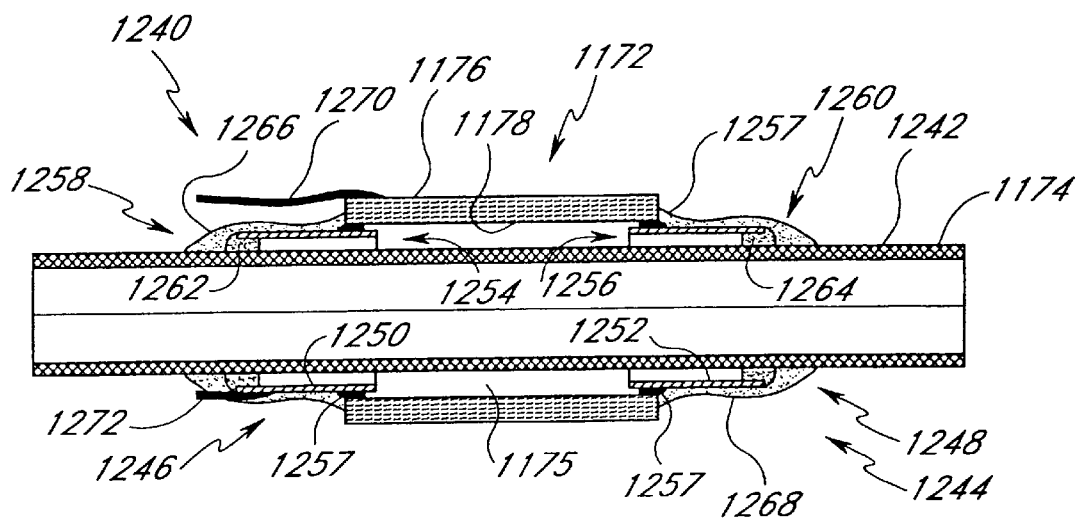
FIG. 38 is a longitudinal sectional view of a modification of the ablation catheter shown in FIG. 37A.
FIG. 38B is an enlarged, partial, longitudinal, cross-sectional view of a modification of the catheter shown in FIG. 38A illustrating an alternative structure for connecting the transducer to the metal surface portion.

FIG. 38A illustrates a further modification of the embodiment illustrated in FIG. 35. As shown in FIG. 38A, a transducer assembly (1240) includes the transducer (1172) supported relative to the inner member (1174) so as to maintain the air gap (1175) between the inner electrode (1178) and an outer surface (1242) of the inner member (1174), via a support assembly (1244). In the illustrated embodiment, the support assembly (1244) includes end mounts (1246,1248).

In the present modification, the end mounts (1246) are formed of metallic bands (1250,1252) which have inner ends (1254, 1256) and outer ends (1258,1260). The metal bands (1250,1252) are soldered or welded to the inner electrode (1178) at the inner ends (1254,1256), respectively.

The outer ends (1258,1260) of the metallic bands (1250, 1252) are sealed to the outer surface (1242) of the inner member (1174) with a sealant (1262,1264), respectively. In the illustrated embodiment, the sealant (1262,1264) can be any known adhesive, including, but without limitation, silicone and loctite.

As noted above with respect to FIG. 35, by providing a metal-to-metal connection between the inner electrode (1178) and the bands (1250,1252), the seal generated by the weld or solder is greatly enhanced due to the high strength and high temperature resistance of such a seal. Additionally, since the outer ends (1258,1260) of the bands (1250,1252) are sealed to the outer surface (1242) of the inner member (1174), the sealants (1262,1264) are spaced from and thus protected from heat generated by the transducer (1172). Thus, the air space (1175) is provided with an enhanced fluid-tight seal.

As shown in FIG. 38A, the weld (1257) between the inner electrode (1178) and the inner ends (1254,1256) are spaced longitudinally from the sealant (1262,1264) such that the welds (1257) do not overlap with the sealants (1262,1264). Thus, the sealants (1262,1264) are further spaced from and thus protected from heat generated by the transducer (1172).

Additionally, in the illustrated embodiment, insulative fillets (1266,1268) are provided over the welds (1257) and the bands (1250,1252). As such, the inner and outer electrodes (1178,1176) are prevented from shorting when an ablation fluid is moved into contact with the outer electrode (1176).

Additionally, as shown in FIG. 38A, an outer electrode lead (1270) is electrically connected to the outer electrode (1176) and an inner electrode lead (1272) is electrically coupled to the band (1250). Thus, by providing at least one band, e.g., band (1250) which is soldered, welded, or otherwise electrically connected with the inner electrode (1178), the inner electrode electric lead wire (1272) can be more easily connected to the inner electrode (1178) via conduction through the metal band (1250).

Figure 38B:
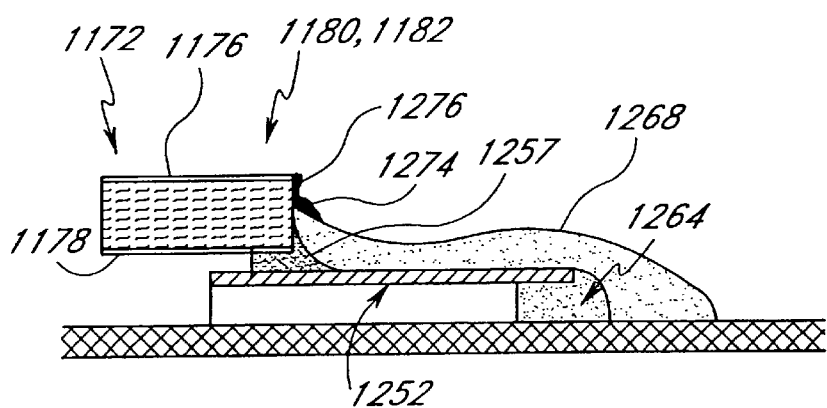

With reference to FIG. 38B, a modification of the connection between the inner electrode (1178) and the metallic band (1252) is illustrated therein. As shown in FIG. 38B, the inner electrode (1178) can include an extension (1274) which extends around the distal or proximal end (1180,1182) of the electrode (1172) and along an annular end face (1276) of the electrode (1172).

By including an extension such as extension (1274) along the outer annular face (1276) of the electrode (1172), the connection achieved by a fillet solder or weld (1257) is enhanced. In the present modification, an insulation material (1268) is distributed over the extension (1274), the weld (1257) and the metallic band (1252) so as to ensure that current cannot be conducted between the extension (1274) and the upper electrode (1176).

In a presently preferred embodiment, the extension (1274) extends only partially along the annular face (1276). However, it is conceived that the extension (1274) could extend completely over the annular face (1274), with a gap provided between an upper edge of the extension (1274) and the outer electrode (1176). It is also conceived that the inner electrode (1178) could be formed such that the extension (1274) extends onto the outer surface of the transducer (1172), and a gap is subsequently machined on the outer surface, so as to prevent the inner and outer electrodes (1176,1178) from shorting. In this mode, additional insulation may be required to prevent an ablation fluid from shorting the electrodes (1176,1178).

Figure 39A:
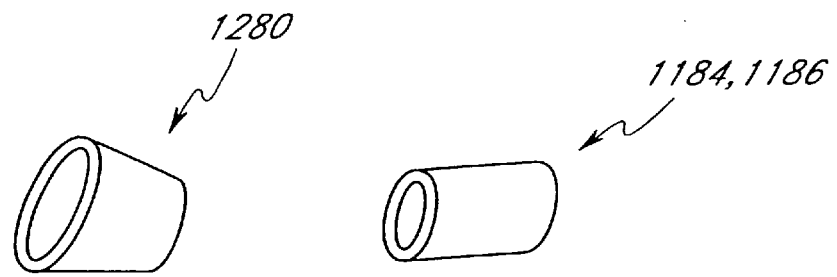
FIG. 39A is a side elevational view of two metallic bands that may be used in the catheter illustrated in FIGS. 38A and 38B.
Figure 39B:
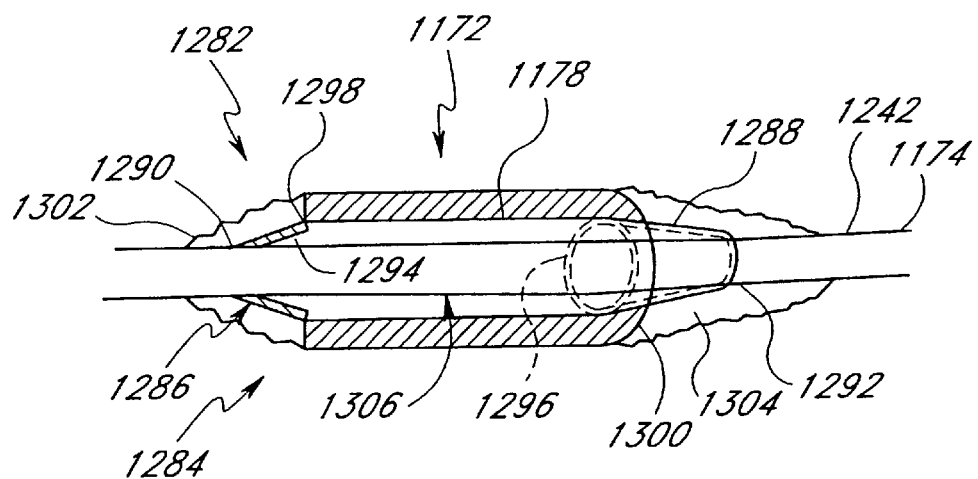
FIG. 39B is a partial longitudinal sectional view of a modification of the catheter shown in FIG. 37A utilizing the metallic bands illustrated in FIG. 39A.

FIGS. 39A and 39B illustrate further modification of the embodiment illustrated in FIG. 35. As shown in FIG. 39A, the band members (1184,1186) are generally in the form of right circular cylinders. However, in the present modification, band members (1184,1186) can be in the form of truncated conical bands (1280). For example, as shown in FIG. 39B, a transducer assembly (1282) includes the transducer (1172) supported relative to the inner member (1174) by support assembly (1284). In the present modification, the support assembly (1284) comprises a pair of conical band members (1286,1288). The band member (1286,1288) include an outer narrowed end (1290,1292) and an inner enlarged end (1294,1296), respectively. Similarly to the embodiment illustrated in FIG. 35, the band members (1286, 1288) each include at least a metal surface portion (1298, 1300) affixed to the inner electrode (1178) by welding, solder, or the like.

As shown in FIG. 39B, the outer narrowed ends (1290, 1292) are sized so as to form a close fit with the outer surface (1242) of the inner member (1174). The outer narrow ends (1290,1292) are also sealed to the outer surface (1242) with silicone fillets (1302,1304).

Optionally, the outer surface (1242) of the inner member (1174) can include a coating of silicone prior to the installation of the band members (1286,1288). Thus, after the band members (1286,1288) have been installed over the silicone layer provided over the outer surface (1242), further silicone fillets (1302,1304) are provided over the band members (1286,1288) and provide an enhanced seal between the outer narrow ends (1290,1292) and the inner member 1174.

As shown in FIG. 39B, the silicone layer 1306 may be applied to the entire outer surface (1242) of the inner member (1174). However, any portion of the silicone layer (1306) positioned within the transducer (1172) is optional.

As noted above with respect to FIGS. 35–38B, by providing a metal-to-metal bond between the inner electrode (1178) and the inner ends of the band members (1286,1288), the inner electrode is reliably connected to the band members (1286,1288) with a high strength and high temperature-resistant connection. Additionally, the seal between the narrowed ends (1290,1292) of the band members (1286, 1288) is further spaced from the transducer (1172) and thus protected from heat generated by the transducer (1172).

Figure 40:
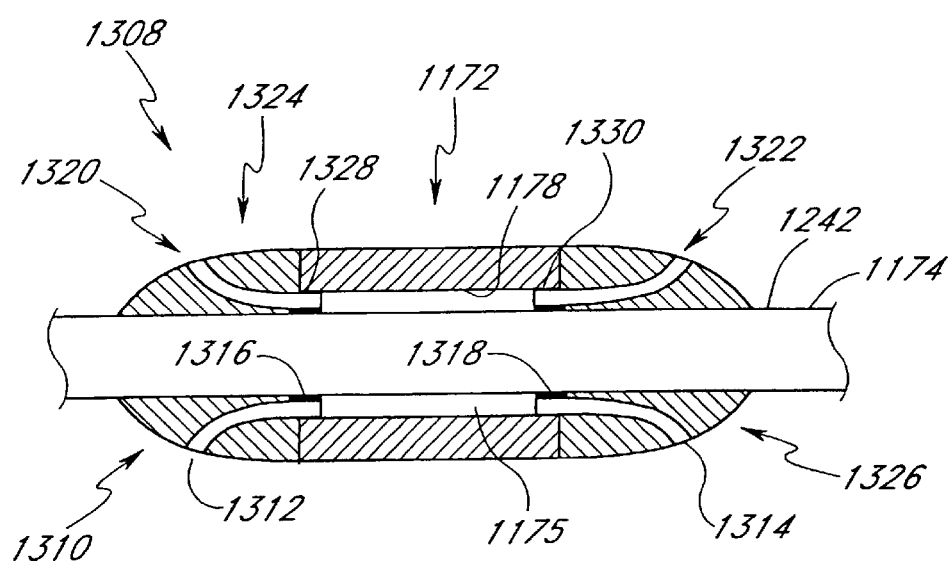
FIG. 40 shows a longitudinal sectional view of yet a further modification of the catheter shown in FIG. 37A including a single cylindrical ultrasound transducer positioned along an inner member and being supported by a pair of trumpet-shaped metallic bands.

FIG. 40 illustrates a further modification of the embodiment illustrated in FIG. 35. As shown in FIG. 40, a transducer assembly (1308) includes the transducer (1172) supported relative to the inner member (1174) so as to maintain the air gap (1175) between the inner electrode (1178) and the outer surface (1242) of the inner member (1174), via a support assembly (1310). In the illustrated embodiment, the support assembly (1310) comprised of a pair of trumpet-shaped members (1312,1314).

In contrast to the modification illustrated in FIG. 39, the trumpet-shaped members (1312,1314) include inner narrowed ends (1316,1318) and enlarged outer ends (1320, 1322). In the illustrated embodiment, the inner ends (1316, 1318) are bonded to the outer surface (1242) of the inner member (1174) with loctite. The remaining inner and outer surfaces of the trumpet-shaped members (1312,1314) are covered with epoxy fillets (1324,1326), respectively. Optionally, the trumpet-shaped members (1312,1314) may include metal surface portions (1328,1330) which are welded or soldered to the inner electrode (1178).

Figure 41:
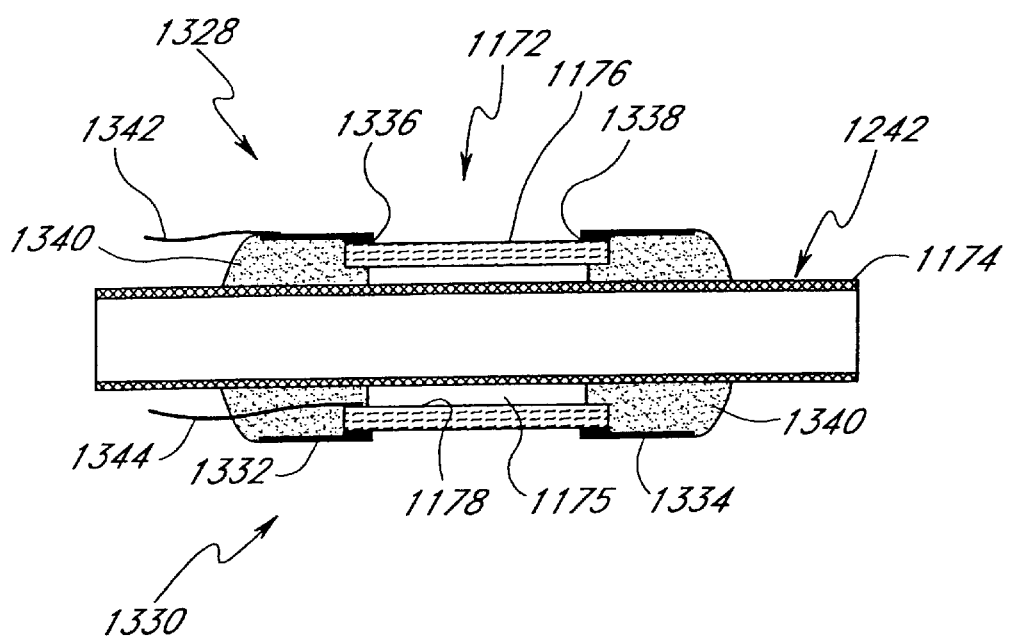
FIG. 41 shows a longitudinal cross-sectional view of a modification of the catheter illustrated in FIG. 38A having a pair of metallic bands bonded to an outer surface of the transducer.

FIG. 41 illustrates yet another modification of the embodiment illustrated in FIG. 35. As shown in FIG. 41, a transducer assembly (1328) includes the transducer (1172)

supported relative to the outer surface (1242) of the inner member (1174) by a support assembly (1330). In the illustrated embodiment, the support assembly (1330) includes a pair of band members (1332,1334). The band members (1332,1334) include at least a metal surface portion (1336, 1338) on the inner ends thereof, respectively.

The metal surface portions (1336,1338) are soldered, welded, or connected by any other method for producing a metal-to-metal or electrical coupling connection between the band members (1332,1334) and the outer electrode (1176) of the transducer (1172).

As shown in FIG. 41, the band members (1332, 1334) are adhered to the outer surface (1242) with an adhesive or insulating material (1340). The material (1340) can be any appropriate insulative or adhesive material such as, for example, but without limitation, silicone, epoxy, and/or loctite. The transducer (1172) is connected to a power supply, such as the power supply (840) illustrated in FIG. 16D by an outer electrode lead (1342) and an inner electrode lead (1344). As shown in FIG. 41, the outer electrode lead (1342) is connected to the metallic band member (1332). Additionally, the inner electrode lead (1334) is connected to the inner electrode (1178) directly.

In the illustrated embodiment, since the band members (1332,1334) are connected to the outer electrode (1176), there is no need to insulate the band members (1332,1334) from the outer electrode (1176). However, as noted above with respect to FIG. 35, the seal between the band members (1332,1334) and the outer surface (1242) of the inner member (1174) is protected by the spacing and separation from the transducer (1172). It is also conceived that the assembly (1328) can include additional band members (not shown) extending from the inner electrode (1178) and outwardly from the transducer (1172). In this mode, connection of the electrodes (1176,1178) with lead wires is easier.

Figure 42A:
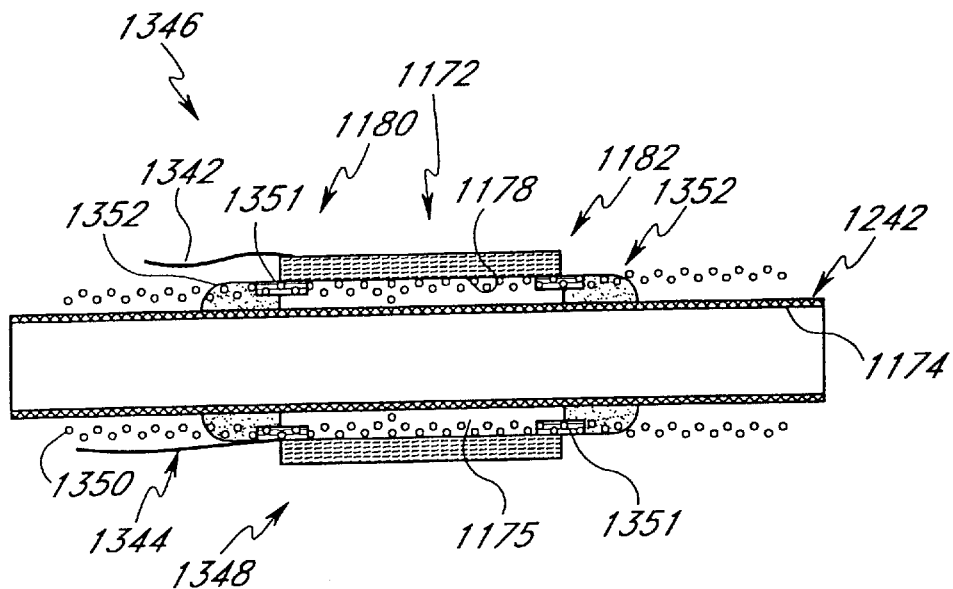
FIG. 42A is yet another modification of the catheter illustrated in FIG. 38A having a braided metal support being welded to an inner surface of the transducer.
Figure 42B:
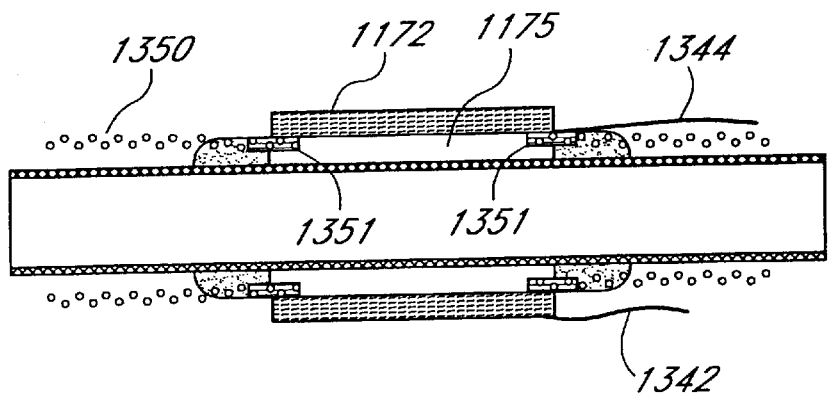
FIG. 42B is a modification of the catheter shown in FIG. 42A wherein the portion of the braided metal support that extends between the proximal and distal ends of the transducer is removed.

FIGS. 42A and 42B illustrate another modification of the embodiment illustrated in FIG. 35. As shown in FIG. 42A, a transducer assembly (1346) includes the transducer (1172) supported relative to the outer surface (1242) of the inner member (1174) via a mounting assembly (1348). In the illustrated embodiment, the mounting assembly (1348) is comprised of a braided metal tubular member (1350) (shown in section) arranged between the inner electrode (1178) and the outer surface (1242) of the inner member (1174).

The inner electrode (1178) is soldered or welded to the tubular braided member (1350) at the proximal and distal ends (1180,1182) of the transducer (1172). In the illustrated embodiment, the tubular, braided member (1350) extends continuously between the proximal and distal ends (1180, 1182) of the transducer (1172). Since the tubular member (1350) is formed of a braided metal, the air gap (1175) is maintained despite the presence of the braided tubular member (1350) in the air gap (1175).

As shown in FIG. 42, an insulative and/or adhesive material (1352) is disposed over the welded portions (1351) in the portion of the braided tubular member (1350) extending outwardly therefrom, thereby sealing the air space (1175). Although not shown, further insulation can be provided over any portion of the tubular braided member (1350) that may be exposed to fluid during a tissue ablation process.

FIG. 42B illustrates a modification of the modification illustrated in FIG. 42A. As shown in FIG. 42B, the portion of the tubular braided member (1350) extending within the transducer (1172) has been removed, thus enhancing the air backing provided by the air gap (1175).

Figure 43A:
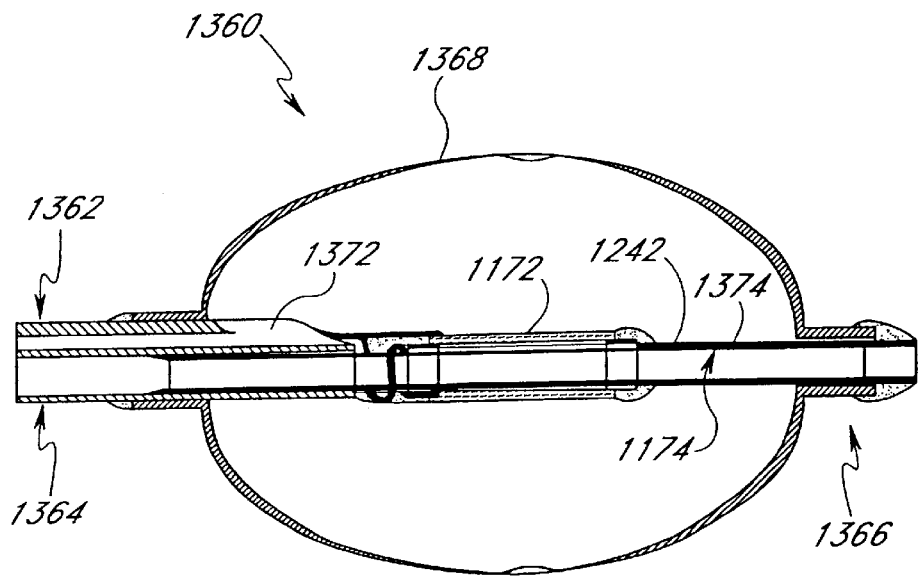
FIG. 43A shows a longitudinal, cross-sectional view of another modification of the catheter shown in FIG. 38A where a mounting assembly includes metallic bands sealed to the inner member with a flexible material and shows an expandable balloon which is illustrated in a radially expanded condition.
Figure 43B:
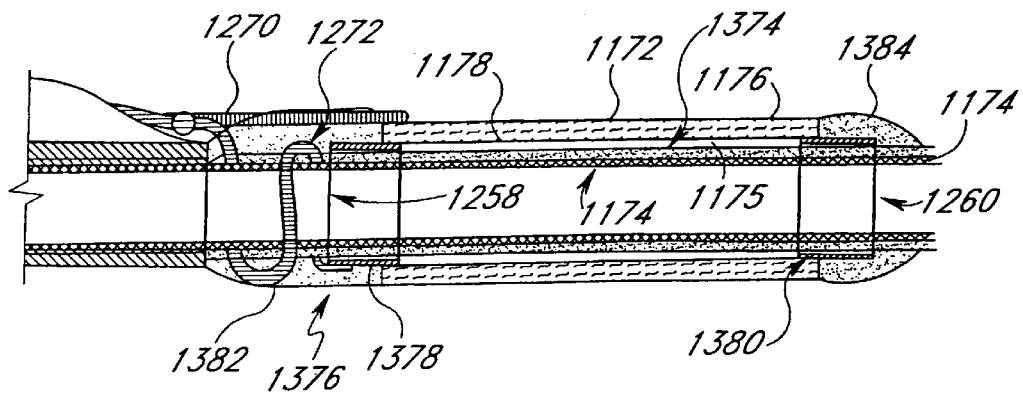
FIG. 43B is an enlarged view of a modification of the transducer mounting system illustrated in FIG. 43A.

FIGS. 43A and 43B illustrate yet another modification of the embodiment illustrated in FIG. 35. As shown in FIG. 43, a circumferential ablation device assembly (1360) includes an elongate body (1362) defining a multilumen catheter body. The elongate body (1362) includes a proximal end (1364) and a distal end (1366). The assembly (1360) also includes an expandable balloon (1368) located along the distal end portion (1366) of the elongate body (1362) and around the circumferential ultrasound transducer (1172).

As noted above, the transducer (1172) forms a circumferential ablation member which is acoustically coupled to the expandable balloon (1368). The multilumen shaft (1364) can include a variety of lumens including, for example, but without limitation, a guidewire lumen, an inflation lumen, an electrical lead lumen, and a cooling fluid lumen. However, FIG. 43 only illustrates the guidewire lumen (1370) and the inflation lumen (1372).

The construction of the expandable balloon (1368) can be in accordance with the description of the expandable balloon (820) disclosed above with reference to FIGS. 16A–16E. Thus, further description of the expandable balloon (1368) is not necessary for one of ordinary skill in the art to practice the invention as disclosed herein.

Similarly, the construction of the multilumen shaft (1364) can be made in accordance with the description of the elongate body (802) disclosed above with reference to FIGS. 16A–16D. Thus, for the description of the multi-lumen shaft (1364) is not necessary for one of ordinary skill in the art to practice the invention as disclosed herein.

As shown in FIG. 43A, the inner member (1174) extends from the guidewire lumen (1370) through the interior of the expandable balloon (1368). In the present modification, the assembly (1360) includes a silicone lamination (1374) extending over the outer surface (1242) of the inner member (1174).

An optional method for forming the lamination of silicone (1374) is to dip the inner member (1174) into a silicone dispersion using a process similar to that used to make the expandable balloon (1368) of silicone. Another method can include taking a silicone tube having an inner diameter smaller than the outer diameter of the inner member (1174), applying heptane to the silicone tube to cause it to swell, sliding the swollen silicone tube over the inner member (1174), then allowing the silicone tube to shrink onto the inner member (1174) as the heptane evaporates. A further alternative method for forming the silicone adhesive includes spreading a silicone adhesive over the length of the inner member (1174) and then allowing it to cure.

Optionally, a metal coil or braid could be incorporated into the silicone lamination to prevent the silicone layer (1374) from delaminating from the outer surface (1242). As noted above with respect to FIGS. 42A and 42B, such use of a metal coil or braid can further provide peaks and valleys which aid in ensuring sufficient air backing for the transducer (1172).

As shown in FIG. 43B, the transducer (1172) is supported relative to the inner member (1174) by a support assembly (1376). In the illustrated embodiment, the support assembly (1376) includes two metallic bands (1378, 1380) which can be constructed in accordance with the metallic bands (1250, 1252) illustrated in FIG. 38A. Additionally, the bands (1378, 1380) can be connected to the inner electrode (1178) in accordance with the disclosure set forth above with respect to the welds (1257) set forth above with reference to FIG. 38A. Additionally, the inner and outer electrodes (1178, 1176) can be attached to the inner electrode lead (1272) and the outer electrode lead (1270) as disclosed above with reference to FIG. 38.

In the illustrated embodiment, the outer ends (1258, 1260) of the bands (1378, 1380) are sealed to the silicone lamination (1374) with additional fillets of silicone (1382, 1384). By mounting the band members (1378, 1380) to the silicone lamination (1374) as such, assembling the assembly (1360) is made easier. By having the silicone lamination present completely under the transducer and extending for a substantial length from either side of the transducer, the potential for fluid ingress under the transducer is virtually eliminated. Any fluid that seeps between the silicone and the inner member is more likely to stay under the silicone material and be prevented from seeping into the air space (1175) under the transducer (1172).

As noted above with respect to FIG. 35, the soldered or welded connections between the bands (1378, 1380) and the inner electrode (1178) provide a high strength and highly temperature resistant seal for preventing fluid from seeping into the air space (1175) from the interior of the expandable balloon (1168).

Figure 44:
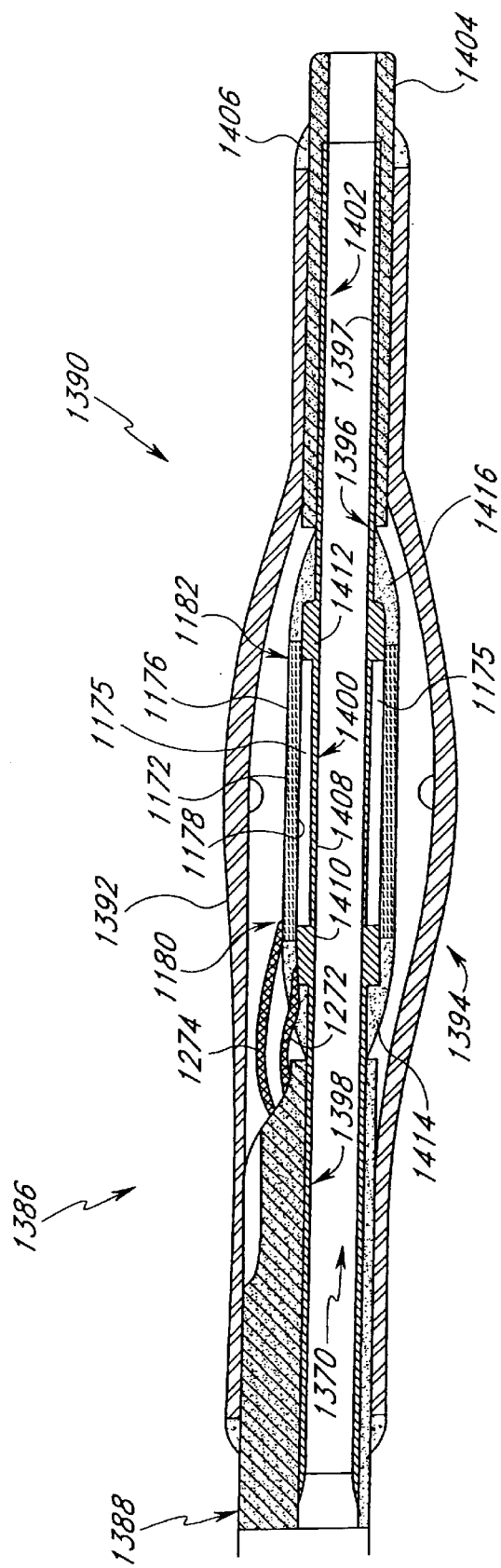
FIG. 44 is a longitudinal sectional view of a further circumferential ablation catheter, and shows the ablation element to include a single cylindrical ultrasound transducer which is positioned along an inner member assembly having raised portions connected to the proximal and distal ends of an ultrasound transducer.

FIG. 44 illustrates a modification of the assembly (1360) illustrated in FIG. 43A. As shown in FIG. 44, a circumferential ablation device assembly (1386) includes an elongate body (1388) including a proximal end (not shown) and a distal end (1390). The assembly (1386) also includes an expandable balloon (1392) and an ablation element assembly (1394). The construction of the elongate body (1388) can be in accordance with the description of the elongate body (802) set forth above with reference to FIGS. 16A–16D. The construction of the expandable balloon (1392) can be made in accordance with the description of the expandable balloon (820) set forth above with reference to FIGS. 16A–16D. Thus, a further description of the elongate body (1388) and the expandable balloon (1392) is not necessary for one of ordinary skill in the art to practice the invention as disclosed herein.

As shown in FIG. 44, the ablation element assembly (1394) includes the circumferential ultrasound transducer (1172) having a proximal end (1180) and a distal end (1182). Additionally, the transducer (1172) includes an outer electrode (1176) and an inner electrode (1178).

The ablation element assembly (1394) also includes an inner member assembly (1396) having an inner surface (1397) and extending from the elongate member (1388) and along the guidewire lumen (1370). As shown in FIG. 44, the inner member assembly (1394) includes a proximal mounting end (1398), a transducer support portion (1400) and a distal end (1402). The proximal mounting portion (1398) is sized to provide a tight fit with an inner diameter of the guidewire lumen (1370), thereby fixing the inner member assembly (1396) to the elongate body (1388). The distal portion (1402) of the inner member assembly (1396) extends distally from the transducer support portion (1400) and provides a mounting area for the distal end of the expandable balloon (1392).

In the illustrated embodiment, the elongate body (1388) is preferably made from a PEBAX material. The distal end (1402) of the inner member assembly (1396) includes a tubular extension (1404) which is also preferably made from a PEBAX material. The PEBAX material used in the tubular extension (1404) should be softer than the PEBAX material used to construct the elongate member (1388) such that the inner member provides a soft tip. Further, a silicone fillet portion (1406) is provided on the extreme distal end of the expandable balloon (1392) to ensure smooth insertion of the distal end of the assembly (1386) into a body structure.

The transducer support portion (1400) includes a main body portion (1408) extending between the proximal and distal ends (1180, 1182) of the transducer (1172). At the proximal and distal ends (1180, 1182), the body portion includes raised portions (1410, 1412) which define an air gap (1175) between the transducer (1172) and the main body portion (1408). The entire inner member assembly (1396) is preferably formed from a metal, such as, for example, but without limitation, stainless steel, platinum, nitinol, and the like. In the illustrated embodiment, the inner electrode (1178) is soldered or welded to the raised portions (1410, 1412). Thus, the inner electrode lead (1272) can be connected directly to the inner member (1396).

In order to insulate the outer surface of the metallic inner member assembly (1396), insulative fillets (1414, 1416) are provided over the ends of the transducer support portion (1400) which would otherwise be exposed to the interior of the expandable balloon (1392).

Optionally, the main body (1408) of the inner member assembly (1396) can be formed from a hypodermic-sized metal tube, with the raised portions (1410, 1412) machined onto the outer surface. Alternatively, the raised portions (1410, 1412) can be constructed of separate annular pieces bonded to the outer surface of the body (1408). Preferably, the inner surface (1397) of the inner member assembly is coated with an insulating material, such as, for example, but without limitation, Teflon, polyimide, or the like.

By forming the inner member assembly (1396) from a metal material, the entire distal end portion (1390) of the assembly (1386) is provided with additional rigidity. The additional rigidity is useful in preventing the damaging effects of bending around the proximal and distal ends (1180, 1182) of the transducer (1172) which can damage the seals between the transducer and the inner member (1396).

Common to a number of modes described above, an outer cover or layer has been removed from the transducer and an improved seal has been provided between the transducer and the supporting structure of the delivery member (e.g., the catheter shaft). It has been observed that with no cover layer, with the particular transducer described above, and with the transducer driven at the power levels described herein, the ultrasound transducer can be used to form sufficient tissue ablation at a location where a pulmonary vein extends from an atrium so as to form an effective conduction block. This result is achieved even though the transducer is supported on the delivery member by a non-elastomeric structure (e.g., by a rigid structure such as those described above in connection with FIGS. 30A–44).

While particular detailed description has been herein provided for particular embodiments and variations according to the present invention, it is further understood that various modifications and improvements may be made by one of ordinary skill according to this disclosure and without departing from the broad scope of the invention.

It is further contemplated that the embodiments shown and described herein may be combined, assembled together, or where appropriate substituted for the various features and embodiments which are disclosed in the following co-pending provisional and non-provisional U.S. patent applications: the co-pending non-provisional U.S. patent application for "FEEDBACK APPARATUS AND METHOD FOR ABLATION AT PULMONARY VEIN OSTIUM", filed on the same day as this Application, and claiming priority to Provisional U.S. Patent Application No. 60/122,571, filed on Mar. 2, 1999; the co-pending non-provisional U.S. patent application Ser. No. 09/435,283, filed on Nov. 5, 1999, for "CIRCUMFERENTIAL ABLATION DEVICE ASSEMBLY AND METHODS OF USE AND MANUFACTURE PROVIDING AN ABLATIVE CIRCUMFERENTIAL BAND ALONG AN EXPANDABLE MEMBER", which claims priority to Provisional U.S. Application No. 60/125,509, filed Mar. 19, 1999 and Provisional U.S. Application Number 60/125,928 filed Mar. 23, 1999; the co-pending non-provisional U.S. patent application Ser. No. 09/569,735, filed on May 11, 2000, which claims priority to Provisional U.S. Patent Application No. 60/133,610 for "BALLOON ANCHOR WIRE", filed May 11, 1999; the co-pending non-provisional U.S. patent application for "TISSUE ABLATION DEVICE ASSEMBLY AND METHOD FOR ELECTRICALLY ISOLATING A PULMONARY VEIN OSTIUM FROM A POSTERIOR LEFT ATRIAL WALL", filed on the same day as this Application, and which claims priority to Provisional U.S. Patent Application No. 60/133,677, filed May 11, 1999; and the co-pending non-provisional U.S. patent application Ser. No. 09/569,734, filed on May 11, 2000, which claims priority to Provisional U.S. Patent Application Ser. No. 60/133,807 for "CATHETER POSITIONING SYSTEM", filed May 11, 1999. The disclosures of these references are herein incorporated in their entirety by reference thereto.

In addition, a circumferential ablation device assembly constructed with a mounted ultrasound ablation element according to the present invention may be used in combination with other linear ablation assemblies and methods, and various related components or steps of such assemblies or methods, respectively, in order to form a circumferential conduction block adjunctively to the formation of long linear lesions, such as in a less-invasive "maze"-type procedure. Examples of such assemblies and methods related to linear lesion formation and which are contemplated in combination with the presently disclosed embodiments are shown and described in the following additional co-pending U.S. patent applications: U.S. Ser. No. 08/853,861 entitled "TISSUE ABLATION DEVICE AND METHOD OF USE" filed by Michael Lesh, M.D. on May 9, 1997, now U.S. Pat. No. 5,971,983, issued Oct. 26, 1999; U.S. Ser. No. 09/260,316 for "TISSUE ABLATION SYSTEM AND METHOD FOR FORMING LONG LINEAR LESION" to Langberg et al., filed May 1, 1999; and U.S. Ser. No. 09/073,907 for "TISSUE ABLATION DEVICE WITH FLUID IRRIGATED ELECTRODE", to Alan Schaer et al., filed May 6, 1998. The disclosures of these references are herein incorporated in their entirety by reference thereto.

In addition, one of ordinary skill may make other obvious or insubstantial modifications or improvements to the specific embodiments herein shown and described based upon this disclosure without departing from the scope of the invention as defined by the claims which follow.

What is claimed is:

1. An ultrasound ablation apparatus comprising:
   an elongate catheter body having proximal and distal end portions, an outer wall and an outer diameter;
   a cylindrical ultrasound transducer coaxially disposed over said catheter body, said ultrasound transducer having proximal and distal end portions, an inner wall and an inner diameter which is greater than the outer diameter of said catheter body, such that an air gap is provided in a radial separation between the inner wall of said ultrasound transducer and said catheter body; and
   a support structure for suspending said ultrasound transducer in a substantially fixed coaxial position relative to said catheter body, wherein said support structure contacts the outer wall of said catheter body at locations proximal and distal to the proximal and distal end portions of said ultrasound transducer, respectively, and wherein said support structure holds said ultrasound transducer without contacting the inner wall of said ultrasound transducer, thereby maintaining said radial separation while reducing acoustic damping caused by said support structure.

2. The ultrasound ablation apparatus of claim 1, wherein said ultrasound transducer is shaped to ablate a circumferential region of tissue.

3. The ultrasound ablation apparatus of claim 1, wherein said ultrasound transducer comprises at least one transmissive panel.

4. The ultrasound ablation apparatus of claim 1, wherein at least a substantial portion of said radial separation is sealed by said support structure to prevent external fluids from entering said radial separation.

5. The ultrasound ablation apparatus of claim 4, wherein a gas is sealed within said radial separation.

6. The ultrasound ablation apparatus of claim 4, wherein a liquid is sealed within said radial separation.

7. The ultrasound ablation apparatus of claim 1, further comprising first and second flanges extending axially from the proximal and distal end portions of said ultrasound transducer, respectively, said support structure being coupled to said first and second flanges.

8. The ultrasound ablation apparatus of claim 7, wherein said support structure further comprises first and second elastomeric O-rings disposed on said catheter body such that said first and second O-rings engage said first and second flanges.

9. The ultrasound ablation apparatus of claim 7, wherein said support structure further comprises first and second sleeves disposed on said catheter body and fitted over said first and second flanges, to secure said ultrasound transducer relative to said catheter body.

10. The ultrasound ablation apparatus of claim 7, wherein said support structure further comprises first and second splines disposed on said catheter body such that said first and second splines engage said first and second flanges.

11. The ultrasound ablation apparatus of claim 7, wherein said support structure further comprises first and second annular members disposed along said catheter body such that said first and second annular members engage said first and second flanges.

12. The ultrasound ablation apparatus of claim 1, wherein said support structure further comprises first and second annular members disposed on said catheter body, said first and second annular members frictionally engaging the proximal and distal end portions of said ultrasound transducer.

13. The ultrasound ablation apparatus of claim 1, wherein said support structure further comprises a shrink-wrap cover layer disposed around said ultrasound transducer.

14. The ultrasound ablation apparatus of claim 1, further comprising an expandable member adapted to engage a circumferential region of tissue, said ultrasound transducer being located inside said expandable member and acoustically coupled to said expandable member.

15. The ultrasound ablation apparatus of claim 14, wherein said expandable member is an inflatable balloon.

16. The ultrasound ablation apparatus of claim 14, wherein a cooling chamber is provided between said ultrasound transducer and said expandable member, said cooling chamber being adapted to allow a cooling fluid to flow over said ultrasound transducer.

17. The ultrasound ablation apparatus of claim 16, further comprising a source of pressurized cooling fluid and a cooling fluid lumen in said catheter body, said lumen having a distal port opening into said cooling chamber.

18. The ultrasound ablation apparatus of claim 14, further comprising a thermocouple for monitoring temperature along at least a portion of said circumferential region of tissue engaged by said expandable member.

19. The ultrasound ablation apparatus of claim 1, further comprising at least one electrical lead coupled to said ultrasound transducer.

20. The ultrasound ablation apparatus of claim 1, further comprising fillets located proximal and distal to the proximal and distal end portions of said ultrasound transducer for sealing said radial separation from entry of external fluids and providing a smooth surface for insertion of said ultrasound ablation apparatus into a body structure.

21. The ultrasound ablation apparatus of claim 1 further comprising a guidewire lumen extending through at least a portion of said catheter body for slidably engaging a guidewire.

22. An ultrasound ablation apparatus, comprising:
an elongate catheter body;
a cylindrical ultrasound transducer having first and second ends and inner and outer surfaces, said ultrasound transducer being mounted coaxially on said catheter body such that a radial separation is provided between said ultrasound transducer and said catheter body for mechanically isolating said ultrasound transducer from said catheter body; and
a support structure coupled to said ultrasound transducer and said catheter body to maintain at least a region of said radial separation for reducing acoustic damping caused by said support structure, wherein said support structure further comprises a substantially tubular member disposed over said catheter body, said tubular member having proximal and distal end regions and an intermediate region, said proximal and distal end regions being formed with a larger diameter than said intermediate region, said ultrasound transducer being disposed over said intermediate region such that it is axially contained by said proximal arid distal end regions.

23. An ultrasound ablation apparatus, comprising:
an elongate catheter body;
a cylindrical ultrasound transducer having first and second ends and inner and outer surfaces, said ultrasound transducer being mounted coaxially on said catheter body such that a radial separation is provided between said ultrasound transducer and said catheter body for mechanically isolating said ultrasound transducer from said catheter body; and
a support structure coupled to said ultrasound transducer and said catheter body to maintain at least a region of said radial separation for reducing acoustic damping caused by said support structure, wherein said support structure further comprises a braided metal tubular member disposed around said catheter body such that said radial separation is maintained therebetween, said ultrasound transducer being mounted coaxially over said braided tubular member.

24. An ultrasound ablation apparatus, comprising:
an elongate catheter body;
a cylindrical ultrasound transducer having first and second ends and inner and outer surfaces, said ultrasound transducer being mounted coaxially on said catheter body such that a radial separation is provided between said ultrasound transducer and said catheter body for mechanically isolating said ultrasound transducer from said catheter body; and
a support structure coupled to said ultrasound transducer and said catheter body to maintain at least a region of said radial separation for reducing acoustic damping caused by said support structure, wherein said support structure further comprises two braided metal tubular members disposed around said catheter body with an axial gap between said braided metal tubular members, said first and second ends of said ultrasound transducer being mounted to said braided tubular members thereby bridging said axial gap.

25. An ultrasound ablation apparatus, comprising:
an elongate catheter body;
a cylindrical ultrasound transducer having first and second ends and inner and outer surfaces, said ultrasound transducer being mounted coaxially on said catheter body such that a radial separation is provided between said ultrasound transducer and said catheter body for mechanically isolating said ultrasound transducer from said catheter body; and
a support structure coupled to said ultrasound transducer and said catheter body to maintain at least a region of said radial separation for reducing acoustic damping caused by said support structure, wherein said support structure further comprises two truncated conical members each having a first end with a large diameter and a second end with a small diameter, said conical members being disposed over said catheter body such that said first ends face inward and said second ends face outward, said inner surface of said ultrasound transducer being engaged by said first ends of said conical member.

26. An ultrasound ablation apparatus, comprising:
an elongate catheter body;
a cylindrical ultrasound transducer having first and second ends and inner and outer surfaces, said ultrasound transducer being mounted coaxially on said catheter body such that a radial separation is provided between said ultrasound transducer and said catheter body for mechanically isolating said ultrasound transducer from said catheter body; and
a support structure coupled to said ultrasound transducer and said catheter body to maintain at least a region of said radial separation for reducing acoustic damping caused by said support structure, wherein said support structure comprises an expandable member disposed over said catheter body and having an outer surface, wherein the inner surface of said ultrasound transducer is coaxially engaged by the outer surface of said expandable member.

* * * * *